(12) United States Patent
Quinlan et al.

(10) Patent No.: US 7,396,646 B2
(45) Date of Patent: Jul. 8, 2008

(54) ALIEN SEQUENCES

(75) Inventors: Sean Quinlan, Melrose, MA (US);
Temple Smith, Marblehead, MA (US);
Prashanth Vishwanath, Brighton, MA (US)

(73) Assignees: Modular Genetics, Inc., Cambridge, MA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 11/224,573

(22) Filed: Sep. 12, 2005

(65) Prior Publication Data

US 2006/0134660 A1 Jun. 22, 2006

(51) Int. Cl.
*C07H 21/04* (2006.01)
*C12Q 1/68* (2006.01)
(52) U.S. Cl. .................. 435/6; 435/91.1; 435/287.2; 702/19; 702/20; 707/6
(58) Field of Classification Search ............... None
See application file for complete search history.

(56) References Cited

U.S. PATENT DOCUMENTS

| 5,580,723 | A | 12/1996 | Wells et al. ............ 435/6 |
| 5,834,250 | A | 11/1998 | Wells et al. ............ 435/7.1 |
| 6,013,478 | A | 1/2000 | Wells et al. ............ 435/69.1 |
| 6,251,601 | B1 * | 6/2001 | Bao et al. .............. 435/6 |
| 6,395,470 | B2 * | 5/2002 | WalkerPeach et al. ...... 435/5 |
| 6,916,621 | B2 * | 7/2005 | Shah ................... 435/6 |
| 7,029,843 | B1 * | 4/2006 | Locatelli et al. ......... 435/6 |
| 2002/0137039 | A1 * | 9/2002 | Gessner ................ 435/6 |
| 2003/0186310 | A1 * | 10/2003 | Kincaid ................ 435/6 |
| 2006/0046252 | A1 | 3/2006 | Ghosh et al. |

FOREIGN PATENT DOCUMENTS

| EP | 01528067 | 5/2005 |
| WO | WO 06/010022 | 1/2006 |
| WO | WO 06/026550 | 3/2006 |

OTHER PUBLICATIONS

Schena et al. (PNAS, vol. 93, pp. 10614-10619, Oct. 1996).*
Kim et al. "Low Power Viterbi Search Architecture using Inverse Hidden Markov Model" IEEE, 2000.*
Azuaje, F., "Clustering-Based Approaches To Discovering And Visualising Microarray Data Patterns." *Brief Bioinform* 4(1): p. 31-42, 2003.
Badiee, A., et al., "Evaluation Of Five Different cDNA Labeling Methods For Microarrays Using Spike Controls." *BMC Biotechnol*, 3: p. 23, 2003.
Ball, C., et al., "An Open Letter On Microarray Data" *MGED Society. Microbiology* 150(Pt 11): p. 3522-4, 2004.
Brazma, A., et al., "Minimum Information About A Microarray Experiment (MIAME)-Toward Standards For Microarray Data" *Nat Genet*, 29(4): p. 365-71, 2001.
Causton, H.C. and L. Game, "MGED Comes Of Age". *Genome Biol*, 4(12): p. 351, 2003.
Churchill, G.A., "Fundamentals Of Experimental Design For cDNA Microarrays" *Nat Genet*. p. 490-5, 2002.
Cronin, M., et al., "Universal RNA Reference Materials For Gene Expression." *Clin Chem*, 50(8): p. 1464-71, 2004.
Dudley, A.M., et al., "Measuring Absolute Expression With Microarrays With A Calibrated Reference Sample And An Extended Signal Intensity Range." *Proc Natl Acad Sci USA*, 99(11): p. 7554-9, 2002.
Eickhoff, B., et al., "Normalization Of Array Hybridization Experiments In Differential Gene Expression Analysis." *Nucleic Acids Res*, 27(22): p. e33, 1999.
Kane, M.D., et al., "Assessment Of The Sensitivity And Specificity Of Oligonucleotide (50mer) Microarrays". *Nucleic Acids Res*, 28(22): p. 4552-7, 2000.
Lee, P.D., et al., "Control Genes And Variability: Absence Of Ubiquitous Reference Transcripts In Diverse Mammalian Expression Studies." *Genome Res*, 12(2): p. 292-7, 2002.
Lockhart, D.J., et al., "Expression Monitoring By Hybridization To High-Density Oligonucleotide Arrays." *Nat Biotechnol* 14(13): p. 1675-80, 1996.
Ross, D.T., et al., "Systematic Variation In Gene Expression Patterns In Human Cancer Cell Lines." *Nat Genet*, 24(3): p. 227-35, 2000.
Schena, M., et al., "Quantitative Monitoring Of Gene Expression Patterns With A Complementary DNA Microarray." *Science* 270(5235): p. 467-70, 1995.
Sterrenburg, E., et al., "A Common Reference For cDNA Microarray Hybridizations." *Nucleic Acids Res*, 30(21): p. e116, 2002.
Tsai, M.H., et al., "Evaluation Of Hybridization Conditions For Spotted Oligonucleotide-Based DNA Microarrays." *Mol Biotechnol*, 29(3): p. 221-4, 2005.
van de Peppel, J., et al., "Monitoring Global Messenger RNA Changes In Externally Controlled Microarray Experiments." *EMBO Rep*, 4(4): p. 387-93, 2003.
van Hal, N.L., et al., The Application Of DNA Microarrays In Gene Expression Analysi *J Biotechnol*. p. 271-80, 2000.
Woo, Y., et al., "A Comparison Of cDNA, Oligonucleotide, And Affymetrix GeneChip Gene Expression Microarray Platforms" *J Biomol Tech*. p. 276-84, 2004.
Yang, Y.H. and T. Speed, "Design Issues For cDNA Microarray Experiments." *Nat Rev Genet*, 3(8): p. 579-88, 2002.
U.S. Appl. No. 10/825,893, filed Apr. 16, 2004, Yakhini et al.
Dobbin, K.K., et al., "Characterizing Dye Bias In Microarray Experiments.", *Bioinformatics* 21(10): 2430-2437, 2005.
Khojasteh, M., et al., "A Stepwise Framework For The Normalization Of Array CGH Data.", *BMC Bioinformatics* 6: 274-288, 2005.

(Continued)

*Primary Examiner*—Jeanine A. Goldberg
(74) *Attorney, Agent, or Firm*—Brenda Herschbach Jarrell; Margo H. Furman; Choate, Hall & Stewart, LLP

(57) ABSTRACT

The present invention provides sequences and reagents for preparing microarrays with internal controls. Specifically, the present invention defines and provides sequences that are not present in the hybridizing mRNA or cDNA, and therefore can be used both as hybridization controls and for inter-spot normalization.

19 Claims, 22 Drawing Sheets

OTHER PUBLICATIONS

Simon, R.M., et al., "DNA Microarray Investigations: Chapter 6—Array Normalization.", *Statistics For Biology And Health* 6: 53-64, 2003.

Zhao, Y., et al., "An Adaptive Method For cDNA Microarray Normalization.", *BMC Bioinformatics* 6: 28-37, 2005.

Baird, et al., "Normalization Of Microarray Data Using A Spatial Mixed Model Analysis Which Includes Splines," *Bioinformatics*, 20(17): 3196-3205, 2004.

Harr and Schlotterer, "Comparison Of Algorithms For The Analysis Of Affymetrix Microarray Data As Evaluated By Co-expression Of Genes In Known Operons," *Nucl. Acids Res.*, 34(2): 1-8, 2006.

Khojasteh, et al., "A Stepwise Framework For The Normalization Of Array CGH Data," *BMC Bioinformatics*, 6: 274, 2005.

Kulesz-Martin, et al., "Melanocyte And Keratinocyte Carcinogenesis: p53 Family Protein Activities And Intersecting mRNA Expression Profiles," *J. Investing Dermatol Symp Proc.*, 10(2): 142-152, 2005.

Vaquerizas, et al., "DNMAD: Web-based Diagnosis And Normalization For Microarray Data," *Bioinformatics*, 20(18): 3656-3658, 2004.

Do et al., "Normalization of microarray data: Single-labeled and dual-labeled arrays", *Molecules and Cells*, 22:3, pp. 254-261, 2006.

Bengtsson et al., "Methodological study of affine transformations of gene expression data with proposed robust non-parametric multi-dimensional normalization method", *BMC Bioinformatics*, 7: 100, 2006.

Jaeger et al., "Selecting normalization genes for small diagnostic microarrays", *BMC Bioinformatics*, 7: 388, 2006.

Lemoine et al., "Goulphar: rapid access and expertise for standard two-color microarray normalization methods", *BMC Bioinformatics*, 7: 467, 2006.

Neuvial et al., "Spatial normalization of array-CGH data", *BMC Bioinformatics*, 7: 264, 2006.

Jaeger, et al., *BMC Bioinformatics*, 7, 2006.

\* cited by examiner

Figure 1

```
>seq1 [SEQ ID NO: 1]
ATGGTTGGGGACTGCCTCTCCCCAGTCGGATGGTCCACCTCTGCGTACACCCCACCTGATCCGGATGAGGCCAGATACA
CCTGTAAGGCTCCTGACCAATTCAAAAAGACACGCACCTGTTTGCGATCCCCAAAGCCTTGCCTGTCGATAAGTGCAGA
GGAACTCTTAATGTGA
>seq2 [SEQ ID NO: 2]
ATGGCCTGCACCCTGGTGGTAGAGGCCCCCTTGTCAAAAACTCCCGACTTGACTGGTGACTTCAATAGCTCCTTGTCCT
GGTCTTGCCTCGACAATAACCCGGTTTTGGGATTAGTGCAGCTCAAGGTGGCCTCCTCCTCTAGCTATAAGTCGGAGGA
ACTTGATCTGGAGCTTCCCAAGCGAGCCAAGATTCTGGATTCGATCAGTGGCACTTGGAAACTCCATCTTCGCAAGGAG
TTCCGCCTCATTGTGTGTATGTCGCATGCCTGGAACCGGCGGCATGCAGCTGATTTGAACCGGTGCAAATGGAAGGGCA
AGAGGGCAGGCTGGAGAGGGGCCCCCGTGCTTTTTGCTCCCATGCAGGTGACGCGCAAGTGTGCACCAGACCCCACAGA
GCAGTCAGGCCTCTTCGATAACTCTTTCCTGGATCACTACCAGAGTCTGGCCTGCATTTACCTAGGCTCCCTTGCCCGA
AAGGGCTCTTCTCTGACCAAGGATGGAAAGGTGGATTTTCAGGGCCCTTGCCTTCGTGGTGGCCAGAATTATTCGAACT
TTTCTCAGAGCTCAGCGTGTTGGAAACCGCTGGACGACCAGGAACAGATCGCCCGTCCCCTCAGTGTCTCGTTGTACTA
TGCAGCCTTAGTGGGCTGA
>seq3 [SEQ ID NO: 3]
ATGCCAAAGTTGTTAAACCTGATTCGGGCAGTCGGCTGCTGTGAGAAACAGACCCTCCTGGCTGCCGAGAGCCTCAATG
ACCGGGAGGAAATCTCCTGTTTGTTCCGGCGAAACCTCCTCCAGGGAATGCTTCTGGGAGACAGAGCAGATGACAATAC
CAGTGACCACACGATAGTCTGCTACACCTTCATGATCCCCTCCCACGCCAGGATGCCTGGAAGTAGGTAG
>seq4 [SEQ ID NO: 4]
ATGGAAGCAGAGCTCTGTTCACGAGGCGTCAACAGACGTGACAATACTAAACTTCCACTTTCGTCTTTGCCTTCAGCTT
CTCCTCATGATTCCAAGAGATGTCCGCGCTCTAAGATCGCTCACGTCTGGGACACCAGGGCCGACGGTGAGATCGATTC
GCGAATCTTGTACTGA
>seq5 [SEQ ID NO: 5]
ATGAACTCTCTGTCTGAATACGAGACCTTAAGGCGGACCATGCTGCAGAGCTCTAACAAGTGTAACTCTCTGTGCCAAA
TTGTACAAACTTGGGTTGAGGGTGGCAAGGCCAAGGCCAATATGAATGGCTACCAGAAGCATTTGGTTCCACTTCGCGT
TCAAATGTGGGAGATGGCAATGCGACTTAATGGAACCCAGCCAAATGAATTCCACCCGGCAGTCCAGCAGTGCATCCTG
GCTCCTTACCTAAAGACTTTCCTCAGTATGCGTCCTGATTCGCAAACTTACCCGGCCAAGCTGAGCTGA
>seq6 [SEQ ID NO: 6]
ATGCCTCGAGGGCGTACTCTGGTATCTCGTCAAGCATGGCGAACAGTGACCGGTAAGGCGGGATGCTCTGGGCGGTATC
CAAGAGAGAGCGGGACCTTGAGTCTATCGCATTTTTCCCTGGGGATTATGTCTAAGCGGAGCCAGGAGGAGCTCTGA
>seq7 [SEQ ID NO: 7]
ATGATGCAGCCTTGCTCCAAACAAGAAAGAATATGCGGACCTCCTGACTCCAGCATCGAGTCCGCGTACCGCTCAGCCT
CTCTCACTTCTAGCCCTGCCACGCTTGCTCCGGCCTTCTCTGCCTGCCCCTGCTAA
>seq8 [SEQ ID NO: 8]
ATGAGGCGAGCCCTGGTAGTGTGCCCCTTGGCGGGACCCTGGAAGAACCAGCGGTCCATTGCCCTGGTGAAAGATCTTC
CCATGAACGCCAGCGTTGCCTCATACTTTATAGAAAGGGGGAGCATCAGCTGGCATTTCTCATGA
>seq9 [SEQ ID NO: 9]
ATGGGGTGGGTCAAGGCCCTGCAGAGTGAAAGCGGCTGGTGGTTTGTATTTCTCAGGGTCGAGTGAGCCTGAAACCCG
AGCCGGGCCTAGCGCTGGTTGTACACCAGGGCTTTGACCAAACAGTCACAGAATGTCTAAGCTTCACAGGAAAGCCCAT
GTATTAG
>seq10 [SEQ ID NO: 10]
ATGATGAGCTTCGAACATTCCGACTTCTCCAATGTCGAGGACCGCAAGCTCTTAACGGAAGCGATGTCCACAGGCTTCG
AAGTAATCGAGTCGCCGTGCAAGATCTGCATGCCAAGCTTTGGAGGTAAAACAACTGCGGATGGCAAACTCACTTCCGT
GACTCAGGGCATGAAACACTGGTCTCTCACCAGAGCTAGTCCCCCGGACCAGTCGCAAAAGGGCCGACCCTACAGGAGC
ACGGTGCAAGGGGAGATTGAAGCGGGACAGCCCCCACATGAAATCTCCTCCGACTGGTACCCCATGTTCAAGATGGAAA
CAGACAGCCCGATTAAGAATGTTCCCCAGGCACACATGGGGGAGTTCGGGCACTGCGACAATCTCCCCAATGGCAACAC
AGTGAGCAACCCGGAGCCTAGGGAGAATGGGAATGTGGCGCCGGGAGTGGGCTTAGACGGACAGGAAGAAATGGGCTGG
CTTTGGCCGGTTCGTCCTTCTTGTATGAACTATTTCTTTAAAGCATCCACTCTCTCCTTTTGGATGGGCTTTCTTGAGC
GCCGCTAG
>seq11 [SEQ ID NO: 11]
ATGGGAAAATCTCGCTTTGAGTATGCAGTGACGCCCCTTCAAGCCCAAGCCCGCAGTTTGGGCAGATCCCTGAATAAAA
GCCCGGTGTTCTTGTTTTACTCTGAGACTACATCCCTGCCAGCCAAGGATCTCCGTGTGAGTCAGGACTTGCTGTGAG
AGACCTGAGCAACAGCAACAGAACAGTCTAGCTATGTTTTTGGCTTCACGGGGGATCAAAGACCCTGAAATGAAGATG
AATTATTCCATCTATTTGGGGCAACCCTTGCAAGAAGGTCTGTCCCCCGTGCAGGAGAACTTTTCTCAATGGGAACTCC
CACTCGTGGCTTACATGAGCTTTTTCTGTCCCTTCCGTGCGGGCGACCGGGGTTCGATCCATAATCATCTCTCCACGGT
CAGAGCGAAGATTGACTACTGTGGTCAGCGGTGCAGTGCCTCAGATCCAAGGAGGGGCCCTCAGGACTATTCTCAAATG
CTCTGA
>seq12 [SEQ ID NO: 12]
ATGCGGGAAGAGTCCAAGACTATCTCGATCAATGGTGTGAAATGGCTCATTGATTTGCCAGCTGAAAAAATCTTCACGA
```

```
GGAACTATGGTGTTGCCGACTGCAGGAGAAGCTTCTACATCCTGGGCCTGTTTGGTTGCCACCTGGTGACTGGAGGGTA
CCGAACATTCATGATCTACATCGGGTCCATTTCTTCTTTCATCATGTATGTGGGGGTCCGGATCATTCGTTGA
>seq13 [SEQ ID NO: 13]
ATGGTGCCCCAAGTGTGCGAGCAGTGGAGCCTGTGTTGGTCCTCGGGCGGGTTCCCAAATCCTGCAGGCTCTTATTTAG
AGCCGTGGTCAAGCGACTTGTCCAGGGAGCTTCAGTGCCCCGGCTACAGCGGCTTCTTAAGTGGCCCCACGGATTTTCT
CTCTATGGGAGTGTCATGTCACCTAGCACAGGAATCATTTCGGTTCCCACTGCAGGATGATTGCCTCCTGACCAAGATG
CACAGGTTGAAAGATTTCTGGGACTCCACCAGCAGGTTTAAGCAGCTGGGCGAATCTGAGGCCCCTCAGCAGATTCGCA
AGAAAAAATCATCGTTTAGTTTCTGGGGCTCATCGGAGAACTCTGCGCCCGCAACCGAAAATACCAGCAAGAAGTCCCA
GGATTCCTTCTTTGATGCCATCCTCAAGTGA
>seq14 [SEQ ID NO: 14]
ATGGGTGTGTCGATGGCCAGCTTCATGCTCTCTTCTGGCCTCCTGGATGCAGAGGGAGAAAGCTTCATGTCTTGGCATC
TCAGCAGCCCTGGAACAGCCGTGGACCGAACGGCCCAAATGTTTATTCACTTCAGAATGATGGGGTCAATCTTCAGTGT
TACCCTGACGCTTGAAGTCATGCGGTCTCTGTGA
>seq15 [SEQ ID NO: 15]
ATGACAATGGAAACAGGGAGGCACCCGGTCATGAAGGACCAAGCCCTTGACGAATGCGAACGGTCGATGTGGCCGGTCC
CTTCTTGGGCCTGGGAGAGTTCTTGTTCTCATCGTGTCGATGAGGGAGATGTATCGGTACTGCTGGAACAGTTTCGGCA
CCAGACTGAACAGCTCCCGCCCATGAGCTACTTTTTGGACAAGCCAAAGCTGTCTTCGTTCCAGGAAGAGCCACGGCTG
TGGGTGACTTTATGCCAGGAGACATTGCCATTTCCCTGGGTAATTCTGGGTATGATGAGCAGGAAGAGGAGGGCCTGT
GTCTGGTCTGTCCGTTGCCCAGACTTCAGACATGA
>seq16 [SEQ ID NO: 16]
ATGGGTAAAATCAATCACACCACATCGACACCTACCTTGAGCACTTTAAAAATCCCCACATTTGAGGCCTTACGCCCGC
TACTATGCCCTAGACTGGATCCCCCCACCTCGTCTGTCCGCCTGGCATTTGAAGGCCAGTCTCAGAAATTGTAG
>seq17 [SEQ ID NO: 17]
ATGGTTCGCAAGGTTGCTCACAATGTTCTGTATGAGACCATGGGTCAGAAAGCTGACTCAAAGTGGGGAACCAGAAAGA
AGCAGCCACAAGGGACCCGCCTGAGCAAACCTTGCACCACGGTGGTGGAGTGGCTGTCTGCCTTCATGTACCGATCCCG
CAAGAAACTGACGAGCCGCTTCTATCTGAAACCTAACATGTCTTCCGGTTCTATCCGCTACGGAGAGCGGCAACCACTC
TTTTTGGACAGCCTGCTTTGGTCCGACAGTGGAAAGGGAGCCTTTGCCTCCTGCAAATGCTCTTATGCTAAATCATTTT
TTGACTGA
>seq18 [SEQ ID NO: 18]
ATGAGCAACTACCTCCACATTCGTTCCCCGGAGTCGGTCCATAACACCTTTCCTTTGTGGGTCCATATTGCTCAAGCAA
AGTTCGGTCACCTACAAGCCTTGTTAAAGCGCGAGAGTGGGTTTGAAGCCAACACCGCGAATGCTGGGCCGCTAGGCCC
CCGCATCAGCGATGACACTCGCAATATCCTTTTGACTGGATTGTTCCTCTCCCTGACCAAGAAGTGTGGATGTGTCCAG
TTACAGTGTGGCCGACAGAGTAGCCTCGATGCCAAAATGCCATGTGACCAGCACTATAGAAAGGTGCAGTCTGCCCTCA
GCCAGGGTCTGCAGATGGGTGGTGCGTGGGTGAAGCAGAAAGCAAGCCAGGAGATTGCCGGGTGGCTCCACAGCAGCAG
CCTTCAAGAGCAGGCCTTGGATGGATCATCCAACTTCGCCACTCTGTCCGTTTAA
>seq19 [SEQ ID NO: 19]
ATGCGGAGAATTAAGTTTGAGTTCAAGAAAATACCTTCTGTTCGTTTGTACCGGTTCTTCTTCGGTTCTTGGGCTAAGA
TTTCTACCCTGGCATTTGTGGAGGACACCTATACCTATGCCTTCTGGATGGAAGGAGCAGGCTTCACTCTTGTCTCAGC
TGACTGCATTACTTCCCGGACCTTTAGGAGTCCACTTGCCAAGGACCCGCTGGCTTGGCGGCTCCTGGATCTTGTGCGG
GCAAAAACTCAAGAAGCGCGGACGAACTCAGCTTTGTCCTTGAAGTGCTCCCTGCCTGATTTTGGTCCACTCGGGGAGA
TCAACAGAGCCCAGGCCTCTGAAGGCCAGCAGACCTTTGGCTCCTTTGAGAAGCCGTCAGAGCATGTCCTAACAGCAAA
GAATCAGCTCCAGGTGATCATAAGTTATCCCTTCTGCTATCTGCTCATCATACCGGAACGTCCATTCGACAGTAGCAAT
ATGTCCTTGTTCAGTAAGCCAAGGGTGCCGGCCTTGGAAGTGATTGGAGTACGCCTCAAGACCCAGATGCTAGTCACGC
CTTTCAGTGAGTTCCAGCTATATTCCCGTGCATTTCTCAGAGAATCAGATTTGTCTGAGAGCTCCCTCTGGGTGACGAT
CTCTTTTGACACGGCGAATCTGTCTTATGTCCAAGCGGCTGAGGAAGAGTGTTCATTGAAGTTCCCTGGCTTACACG
TGGTCTTGA
>seq20 [SEQ ID NO: 20]
ATGGGGATGATGCTCAACTTTTGTCTGAGAATCTACTCCAGCAGAAAGGGAGACGCCATCATGTCTGGCCCTTCTGGGT
CTTTCCTTAGAAAAAAGAGTGTGCCCTACCAAACCTGGCGAGCGGAGCAGTCTCGTAAGGTAAGCGTGTGCTCCTCGCA
GTTTTACTCCCAGACCATCTTGCGTTGGCGGCCCCAGGATGCCGAAACAGAGAGACAGAGGAGAAGCGGCTTCAAGCTG
GCCATGATGGCAGCGGGCAAGTGCCAGCCTGTGAACGACCCCACCTCTTGCTCTTATGAAGCTTACCTAAGGCCCATCT
GGAATGGTATGAGCTTTCTTGATTGGCTGATCTTTGTCCCATGAACCTTGGTGGACACAGACACAGCACCTCCCTGAG
CGCGAACAAGGTCACGTCCATTTACAAGGAATATGCAGGCTATTCCACCTGCTCGTCTACCAGAGGCTGA
>seq21 [SEQ ID NO: 21]
ATGCAGTACTGCGCAGCTGCCGCTTCCAAGCTGTTCCCAGCCTTGCCGTTAAGGGCCCAAACCCTCAGACACTACCTAA
ATGTGGCCCTACACAAGTCTGCCCTCCTGGGAGATCTGGCCTGGCGGCGGAACTCGGCAGGGGGCCAGGGCTTTATGAC
TCTAGGGCCAAAAGAGATTCTGCCAGCTCAGGTGGCCCCAGGTGGAGAGTTTGGATGA
>seq22 [SEQ ID NO: 22]
ATGTATGCCTGTGCTGCTCTCAGTTCATTCCTTGCCTTCCCAAAGTACGGACTGACTGCCAAGAGATACCCAACCCTGA
GAACCTATTGCCTCTGCTTATTGTGGAAGTGTGAGAAGCATATTTTGTGGCAGGGGATCAATCTAACGATGCGACAGGT
GAGTGCCAATGGGACGCCCATGGTGAACTGGGGGGTGCTGAAGCCCACCACTCACCAGATTCTCAATGGTGACACAGAC
TGTCTGTGCCGCCCGAGGTCATTTGGTTTGAAGGCCAATCAGGCCCGCCGACCGAAGAAGTACCAAGGCTGCCTCTCAC
```

```
GGAGGTGCTCTGCTGACTTCCTCTGTTCCCATGGGGCTGTTGTAAGAGATCAGTGCTCGATGATTCAAGTGTCTTTGAG
CACCCGGCTGCCGTTCTCTAATCCATGGATTCAGGTCGCTGTCATGAAGTTCTTTTGTTACAGAACCAAGGCCTGCGCA
TGTAATGGGGGGGGTAAAAAAGCCCTATCTGTGAGTTGGCAAAAATTCCAGAACTTGTACGTGACACGGAAAGCAATCC
TAGTTTTCAGCATAGCTAACAAGGGTTCCCTGACTAAGATAAACATCCAGCGGAAGAAGCTCAGTAACAGGGACTCAGT
GACAGAGTGCGTCTTCGGACTAACCTATAGGAGCTTTCTAGGTAAACGCCATGTATTCGAAGGAGCCTCACTCTTGACG
AACGGACCCAACCCAGGGAGGAGCAAGTGGCCCTGTGAAACAATAAGCGATCAGTATTACTGTTTCAACAGGAAGTTGT
CTGAGAGCGGCATGTGCTTCATGTTGTGTAGTACCTGCAGAGGGTACCTGCCGCCGGACTACCTGTTTGCAGCTCTGCT
CAAGACAGTCAGCCGGCACATCGTTAAAGTCCGCCAGGTGTTGCTTTTTTTAGAACTTTACCCTGGCTCGAAGGCTAGA
TCAAGCGATGAAATTCCCCACGAGCACAATAAGACGCCTGAGCTGGAGGAACTTCCGCCTATCAACAGCTGTACCCAGA
TTGCCATGCTCCTTTGCAGCCGCTCCTCAGTGAAAACCAAGGACAGTACGACGGCACCTGTTCTGTGTTCTTTTTTCCT
TAGACTGTTTGCTGAGGAAATCCGGCTGCGCTCTTTTGAACGGGAGTACCGCAAAGATTCTTACAAGTACCTGCGGGTG
TGA
>seq23 [SEQ ID NO: 23]
ATGGATCTCGATCTGCGGTTCATTCTGTTATGGAAACAGGAGGAGCTGGGGCTGTGTCGGTACCTGAAAATGAGAAAAT
TTAGTCTGCAGTATGGGAAGACAAAAAAATGTTCCTCACCGGCCTGA
>seq24 [SEQ ID NO: 24]
ATGGGCAGTCGCGCCCCATCGTCTGGTGATGAAACTCAAATCCACGAACTCTCACTCACCCCCCGGGATCCCACCTTAA
AGGAGGGGACCAAGAAGGGCCAGCTAAGGGCATCCCCGTACTTCCTTCGTGCAATGCCGTCCTTCCTTTCAGTCAACAC
ACCCCACCAGCAGTTCTACCACCGTCAGCGGGCCAGCTTTCAGGACTACGCGGGAGATATGGCCTACATCGAACTTTTC
AGTCAGATCAGTCCTACTGCGCAAAGAGCACTACAGATGCCAATCAACCCTGCGAACGCGGGCGCGGTATCCATGGGAA
ATCTTTCCCCTTCTCCATGCTTTTGCCTCGCAACTCCGTGTTACCCCCAACCAAGCGCCCGTTCCAAAGACTTTCCAT
TCCGCAATCTCTGACCAGCAAGGGCCACTACCTGAGCCTGTATCTGCTGGAAGGAGAAATCTTAGCAGGAACCATCTCC
ACCGTAGCGGTGGTGACCAAATGGACATCTCAGTTCTACATGTGTGTGCTGGCTGTCCTTTACGGTCAACACGCACCTT
CCTTCAGTCAGAGGGCTGTTGAGGTTGACCGGAAGTCCCAATCCAAGGCCCCAAAGGTTCAGGAAATGTGGCGAGACGG
GATTAAATTCACGTCTGGTAAACTCCTCTCCTGTTGTGAGGGGCACCGCATCGCCTTTGACTGGTCCTTCCCAACCAGG
TTCATACAGATTGGACGTCCGGGGGAGTACATTGCAGAATGCTTCCAGCGGTCCCGGAGAAAGGCTAACTTCCTGAACG
TTGACATAAACAGCTGTCTGCGCAAGAGCATTGAAACTTTTTTTGGGAGAAACTATATGCACCCGCCGCGCGACCCGCT
CTTTTTCAGGGTGAGTATCCCTTGCTGCTATTGGGCACTAGAGGGACCCTTCTGTGAATACCCCAAATTCCTTCACGCT
TAA
>seq25 [SEQ ID NO: 25]
ATGGAACCAATCGCGCTTAACATCAACTACCAGCGGATGCTGCTATCGGGGCATAGCTCAAACCAGATGATTCATATTG
TGAACAAAATTGATCTTGCGAGGACCCCCTCTTCTGTAACCAGATCCCGGCTCAATGACTGTAGAGGCCCTTTATGCAG
AAAGGACCAAAAGGCTGAGCGCGACAGCCAGCTTGGCAAGCGGGTGCACTATGCATTGATCCTTCGGTTCAATCGGCCA
AATGCGCCTGACAGCCAGGACTATTCGCTAACTTGA
>seq26 [SEQ ID NO: 26]
ATGCGGAAGTCGCTTTCGCGCAAACTGCGGATGGCCTGCTCCAAGGGCCTCTCCGGGGTTCCTGTCTCCTCTTGTCACA
TGCACTACTTCGACGGGTCCCTGGTGGTGCGGCTGACCTGTAAGAGGAGACATGGCTTGTGCAAAGAACAGCAGGGTAT
CGCGGGCACCATCAGACAGAACGGCACCATCCTAAGTTAG
>seq27 [SEQ ID NO: 27]
ATGTATTATCCAGATATTACGTATCCCAAGCCCAGCAGAATTATTGAGAACTTAGATGAAATTGTTTCTCAGTCAGGAT
CGATTGAAAATCACTCCCGACCGATGATTGGTCTGCGTGTCAACTCTAAGTGGATGCCACTTGGAGGGGGCCCCTACAA
GATGATGCGAAGCAGTAGAAAAAAGGTGAGTCAGTGCCTTCTGAATGACATGTAA
>seq28 [SEQ ID NO: 28]
ATGGGTGATGTGGTCATGACGGAGGAAAAGCTGCAGCGCCTTGGTGTTTGAAACATCTGCAATGTCTGGGTTTTACAAGA
CATGGACACCCCGGTTCTACGGAGTGCAGGGGCATCGTGTCTCGGACCTCGCTGCTGTTCAACAGCCGGCGCGGTGA
GTTTCGAAGGCACCCTTCACCCTCTCAACGACTGTGGGCACTCCTGGGTGCATGGTGGCGTGGATCTGGCATCCTGGAC
TCCGGGGCCCTGCGTGAAATGGAGCTGGGCATCCAGGGTACCATACGATTCTGGCTACCTACTGCGCGCTCGCGGAGTT
GCTTGCTCTGCCGATGCCTGGGGGCTGAGATCCAGGCTCTCAAGGGCAACAACCAGAACTCATTCTATCGTCAGCTCTT
CCGCCAAGCTTCGTACCGTTATCTGAGATGTAGTTTGGCGTACCCATCGATGGGTGACTTCTTGCCATTGCAGCGCGGC
AAGTGGGTTCTCCTGGGCAGAGGGAAGCCTCCAGGGCAAGCTCGAGCTCTGAAGCGCACAGGGGATGGCAAGGGGCAGG
CTCGATTAAGAACAAGTCAACTTGTTCATTCCCTGGGAGAGTATGTGCAGGTTTTCCCTTTCTATCCAGAGGACCTAAT
GCTGAGTAAAGACCAGGAAGACAGCCAACAGAGAGTGAACTAG
>seq29 [SEQ ID NO: 29]
ATGTCAAGTGAAACTTCACCCCGCCTGATCCCTAAGTCCTGGAGTAGAGGGCGCAGCGAAATTTCAATCCCTTCCATCA
TTGCCCTGGGTGAGCTGCTTGCCCGTTGGAGGCTAGTTTCTCTCTCCATTGGCAAACGTCTTATGCATCCTCTGCGCCA
GACATACATGCGAATTTTTCCACGAACCTTTATTGTCAGTAAGATCCCTGATGGCATGGAGATCATGCTAAGCAAGTGG
TATGTGGCTAATGGAACTCCCGAGCCCAAGAGGTTCTGCCTGACAACCAGTCAATGGCTGAGCCTTTACATGATTTCCC
CATGCACATCATACTGCAGACTCCGCGCATCAGCAATGCCGCGAGGCAGGCGGCTTGAAGCCTGGCACGGACTGAGCAA
GGCTGCCAAGGAGATCACTGCATCTCGGATGTATGCGGAGATCCTCTTGTCCGAGTTAATGCCGGTGGAGACTTATATC
TGTTACTTCCCGAACCTCGAAGCCAGATGTCCACGAAAATCCCCGTTTTCGCGTGATGAATGGAGCATGATAAGCGTAC
CTTTGATCAACAGTGTGTTCCGCTTGCGCTTCTCCTGGCTTGCCTCTGGGCCTTGA
>seq30 [SEQ ID NO: 30]
```

```
ATGTTCACATTCACCAGAGTTGGGTGGCCTCGGTCCCATTGGAGATCCGCCGTGGGGAACAGTGAACGACCCCTCTTCA
TATGGGCAGCCGGTGCCCTGCGGCCCAAGGAACCTCTTCTGTTTCGGTTGGAAAAAGGCCGGGGTGTGGCCGAGCTGCG
GAGAAGGCTGAGATTTTTACAGTGTGAAGCTATGTATTCGAAATTTCTGGGGATCCCTGAAATGATGGAAAACTCCAAG
GCCGTGATCGTCAATTTTTGCACCAAAATCGGACGCAGGGAATGGGAGTCGCAAGCGTCAATGCTCCCACAGCTGTCAA
ATTTCATGACACCGCCCAGTGAAAGCACGCTAAGCAGCTCAGCCACTTTGAGGATGAGCCTCCTGTACTTCGCTTCTGC
ACCCACTAACAAGACAAAAATTAAGGGTGTGAATTTCTACTCGCCTCCCAACCACATGCCCCTTAAGCTGCTAGAGTGC
TTGAGACATGTGAACCGCGAGTGCTTCACCAACCTGGGATACCTTCTGGCTTATATGAATTGCAGCATGGACATCCTTA
AGGGCAAGATTTCTGACGTGATGGGACCGCGTGCCTCAGAAGTCAACTCAACAGACAGTACTATGTGGGTCCTGTCAAC
AGGAGCCACCCCCACCGTGGTTCTCATGGAAACAACATGTGCCCCCCTGTCTTGGAGCTACCTGCCTGCTCTGTATGAT
GCACCGCGCTTCACATCCGAAACCTACATCTCCCTTGCTGAAGCCTGTTATCGAAGCCAGGCCTTTCAGCAAATGTAA
>seq31 [SEQ ID NO: 31]
ATGTACCTCATGGCACTGAATATAGAGCCTGAAGATCTGGCGGGATTCAGCAAACTCACTATGGACCTGTATTTTGATG
AATATGCAGATTCCATGTTGGACAAGAGTCCCGGCCTGATCGAATTTCTGACCGTTGGGACTCCGAAGTGTCTTCTGGG
GCCTCGGCTGAGTGGTAGCGATGCCCATCGGGCCAGTATCGCTCGGGACTATCGCCCATGATCCAACAGGTGGGTCTG
GGTGTCAACTTGGTCACATAG
>seq32 [SEQ ID NO: 32]
ATGATTTCCCACACAATCTCCGAGATCCTCACCGAAGTTCAGCGGCAGTTCTTCTTTCTGGCCTGCAGGGGCTTCTTCT
ATCCGCCTCTCATGGGTGGCCGTGAAGCTTCTGAAACTCAGGGAATGGAATACGGCAAGGGGTGGAACACCCATGTCCA
GTGTCGTAAGTGCAATGATTGTGTGTGTCTGTTGGGGGAGGTTTATGAGAAAGGCATAAGATACAGTTGCAGTGTGAGT
TACAGATCCCTGGCCTACCTGCAATGA
>seq33 [SEQ ID NO: 33]
ATGGAACCTATGTCTGCATTACCACTCGAGAGCGCATTGAATGACAAAAAGTTCAGTACCAAGACGGGGTTGCCAAGCG
GACTTAAATTTGGAGAGGTTGCTCCAGCCCGAGCCCCCAATGGCTTGTCTAGGAAAGCTTCCACCAGGTTCCAACAGAC
GGACGTTCGTGGCAACCAGCAGCATGGTCTTATCATGATGCAGATTTGTTGA
>seq34 [SEQ ID NO: 34]
ATGCACGGCATCCACTACTCGCTCCCCACCCAGACTGCTGACAAAGCCTTAGGTGTGGGCATTTCCTCCCAAGGCCAGA
TTCCTCAGGCAAATGCTGGCAACCTCCCCTTCGCCGATGAGCCGGGATGGCAGATGCTCAGGATGGGTGGTGGAGAAGA
CCAGTCCCGGTTCACAACATTTGTCTTGATTCGATTCTGTGTAATCTTCGTCGGCAGGTGCCAGGATATGTACCTGCTC
AAAACAACGCCACCTGAACTGCGCCAGAATCTCATGTGCCTGAAGATGGAGTGCACTAGCGCTCTCAAGCTTAAGGATG
CGCAGGTGCAGCTTGACCTCACGCTTCCCTTTTGCTACGCCGCCACGGTGTCGGCCTAA
>seq35 [SEQ ID NO: 35]
ATGTCAAGCTTCAACTCACAGTACTTCTTCTTCGCACTGGAACCCACGTGGTGGTTCTCTATGGGACCTGAGGACATTG
TGATGCACCAGCTCCTCTTTTTTCAGGCTGTGTGGAGCTGCCAGTTACCGGTGA
>seq36 [SEQ ID NO: 36]
ATGTGCCAGAGGGAGAGACGATTCACATACCCGCAGATTAGCCACTGCAGGGAATTCTGCAGAGGCTTCACCCAAAGTA
AAGAACCTGGAGGACATGACACAGCTGAGTACAAGGATCTGGCTGAAGCCCTGCCAATGAAGAACTTCAGCTGTCCGGT
GCTGGAGGAGAGTTTCCTTTACGCAAGCGAAATGAGAGCTTTTCTCAAGCAGCAATTCGATAGTTGGAGGTAG
>seq37 [SEQ ID NO: 37]
ATGTCCTGGGTGCTCAAACAGTTTAAGGTAATGCGAGCCAGACCTCAATTCCTGATGGCAACTTCAACACAGGGGAAT
GCACCAAGAACTGGAATGTGAGGTGGAAAATATGGGATCTCTCAATGCTGCTTGACTCTCATAACACCTCTTACTTTTA
CATTTGCGATCCGGTAGTTTAG
>seq38 [SEQ ID NO: 38]
ATGCATTGGTCCCAGGTGAAACTGTTGGAGCGCTTCAGTAATAGCAAAGAGACGGGTGCTGAAGATGTGCTAGAAAATG
CCATGCCTTCTGAAATGGCCTCTACCCTTGGAGAAAGCCCCTAG
>seq39 [SEQ ID NO: 39]
ATGGATTCGCCCACGACATTCACAAAGTTCACAAACTGGATTTTCCTTTATTCTGTGAGGGACGACCACGTGTGGCTGG
TATCTCCATTCCAGCAGTTCTGCTTCCCCTTATCCTCTGCCGCACCTGGGCCGCTGGCATGCAATTAA
>seq40 [SEQ ID NO: 40]
ATGAGAAAGGATTTGGAGTGCCTCCTGTCCAAAGGCACATCGAATATGCTGAAGAGTTTTCTGATCTGCTGGGGGAAGG
CTACCCTCCGCTTCTGCGAAGAAATGCCTCTCACCCTTGAGATGGTTCACCTCTACATGGACATCCCTGATGAACGCTG
GCCTCCCTCTAACCAGCCATTCTTTGGAAAGTTCTACTCGACTTTCTTCAGCCGCCACAGCCCTGGGCCCAAGCTCCAC
CGCCCTCAGGGTGCAGGAAGGACACAGCTGTCAGAGGTCGTGGGCAACTTGCGGTGGGATCAATACTGTTGGGGCAATC
CTCAAACGCGCAGGCCCAGTTGA
>seq41 [SEQ ID NO: 41]
ATGCCCTGCCTGGGCCGACAGGAACTCGCCCGCGCGGGAGGTGTGCCAGGAAGTGCGGATCGGAGGAAGAAAGCGTTCA
GGTTGGAAGAAGCCAGATATCCCCTGTACATGGAGGGTCTTGGATCTGAGACGCAAGGGGCAGCAAAGGATCAGGCCCC
CTCGTTCCGGAGCCCGAGAATGGCCCTGCCCTACCTAAGACTCCGGCCCATCAAGAGAGTCCCCATCATCTGGCGGATA
GTTTTTCAGAGCCTCCACCCTGGCGAGAAGCCCAGGGAGACGTATGGAAACGCATACCGGGGAGAAGCGGCCAGGGCAG
AGTTCACCCAAGAGTCTGCAAGCCAAAGCTTCACTTGA
>seq42 [SEQ ID NO: 42]
ATGACCTTCATGAACGTATGTATAGCCGGGCAAGATGCAACGCAGCCATATTATAGGGCCAGTTACAATAGCCACAGTA
AAGTTCACACCTTGGAATGTCGAGTTGAGCTCAAACTCACAGAATTAATGCGCTGTGCGCATAGAGGAAAGGGCACCCG
```

```
TACCACGCGCTGTCTTATCACTGCCGCCTTAATTCTGTGTCCCCCCACCTCCAAAGAATTCGCGTACAACAACTTGCTC
ATTGCTTCCCACACTTGGGGCAATGATTAG
>seq43 [SEQ ID NO: 43]
ATGGCACCGGACAGGTCCACATTCTCTTACCTGTGGGATCCTCAGGATCACCATCAGGACGCCTCCCCTAGTTCTCCAA
TTGCCAGGGTGTCATCACCTGCCTTCCGGGGTTATGACTCAGAGGACCTCGCATGCAGCCCCCCCTTTCAGAATGCCCA
GCTTTGGTGCAATTCGAGAAACTCAACTGTAATGCTGTACCTCACACTGTAG
>seq44 [SEQ ID NO: 44]
ATGAGCGTGAGGGAACGTGAGGCTTCAGACAAATCTTTCTTTTTGGTCTTTGCATTTTTTTTACGAAGCAGTTTCATTG
GGTTCATGAGACAGTCTTTGCATAGCTGTGCGAAAGCACGCTGCGCGACGTTCAAGCCCCAGGAACGAATGTGTAACCA
GCGGACCATGGTTGCCAACGCTCCGGAACCCAGGCTGATGACACTGGTTGTCCGCTTGGTCGGCCATGGCGGTTGCACA
ATAGTCACTTCTGACCCCCGATCCCCCCAGGGTGAGAAGGCCCAGGATCGCTACAACCTCATTCGGGTGCCCCTGTACC
CGGCTGCCTACATCCCCTGTTACTACATGAATGTGCTATCCATCTCAAGGGAACTTGAGCTGCTATTGAGCTCAATCCA
GGTTGAAATGAGACACCCAGTGAGCAACCCGGGACAGTTATACTATATCTCTGGTCAGGTGGATCCCGGCTGTGACAGG
AGAATTGCCAAGTCGCCTCGGGATGACCAGTCGGGATCTCCCCGGCAGAGAGATGCACCCAGCTACAAGGTTTCCACGT
TTTACCGGGCTAGCAGAGCTAAGAGTAGACTAAAACGGACAGACCCCAAGAGGACCTCATCCAGTCATTCCACGTTGAT
TTTGTTTATGCTAATCTTGGACACTTCGAAGTTCATGGTGAAGTCCAGCCGGACTTTCACTCTCCTTCTTCAGGACTTC
CATTCAGTGACACGGAATCAGAGCTCCAGATTTCAGTTCAGGCGGAATCAGGAAACAGCGAGATCTCCTGGAGTGGCCA
CTAAGGAGACGGGAGCGTTGACACAGATGTCACCCCTTTCTCCGCAGTACCGCAGAGTGACTGAGTCGTTTTCTTAGT
GCACGGTTCTCTCTCTCCACGTCGGTGCCTGGAGCCCTACCCTTTAGCCCAACTGGAGGAAATCCAGAAGTGA
>seq45 [SEQ ID NO: 45]
ATGACCTACCTGTGGATGAAGGCGATCAGCAGTCATGCCAAGCTGCCGGCAAACTTCACGATACAGTCATTCTCCCAGT
GCATTCAGGAAACAACCGCAAGTCCTGATAGAGAACTCCTGACGATGCTGAAGCCCACAAGATCTCAAGAAGAGACGGA
CCTACTGAATAGACTGTGGCCGGATAACCTCTCTTCTCTGACGGAGATGCCAATCTCCCGTTGTCTGTGCAGAAGCATC
CGCCCTTACACCTCTTCAGCGGACTCCGTGTCTAAAGAGATGTGCCAGTTTTGGCAGGTGGCCTTTGGCGAGGCTGGCA
AGCGTGAGGACTGTCCTCTTTACCCCAGGTCAATCCTGTAA
>seq46 [SEQ ID NO: 46]
ATGAAATCCTGCGTGGATGAAGAATCAAGTCATTGCTATGGGTCCGCGCGGTGGGAAGCGCTTAAGCAGAGCACGGGTT
TTTTCGCCACTCGTGAGCGAGAGAGCGGCTTCAAGCAGGATGGGTCCTGA
>seq47 [SEQ ID NO: 47]
ATGCTGCTGATGCCAGAGTTGTTAGAAACAAAGGACTCAATGGAAGCCGAATCCAAATTGAAGAGCATCAGCATGCAGA
AGGCTGAGTTCAAAGAGGGGGGCATTTCTTTAGGAAAACGGCTCACATCGTACCCGAAGGTCCCTCTGGAATCTTGA
>seq48 [SEQ ID NO: 48]
ATGTTCGCCTTCTTAGATCTGACTAGTTTCATTCTCGCGGGCCGGGCTTGGTACACTACCTCACCCTCTCCTGACACCG
AAATCTGGCATTTACCGCCTTCTGGTGCTGAGCTGTGCAAAGCTTGCCTCTTGCGAACCCGCAATGCGACAACAGACTC
TGAGTACCACACTATTTCCCGGAAGTACTTAATTGACCCCATCTCACAGCTTTCGCTGTTTACCTTAATGCACCTGCTC
TGA
>seq49 [SEQ ID NO: 49]
ATGATGAGCAAGCATCACACCCCAACCACGGTACTCTGCTGCCAAAATGAAGACCTGCAGGGAACCCCGAGGCTGCGAG
TGCTGAACCCAAATCAAAATACCTGGGGCATCATCAACTTGGCCTACAGAAGCATGTGA
>seq50 [SEQ ID NO: 50]
ATGAACGACATGCCATGCGCTCTTTGCGACCAAAACACGTATCACCGAGAGGGGAAATAAGTTCTTCTCCCAGCCCTCGA
CCAACTGGAACACGTTCCAGGCAGAGGAGCACTGTCAGTCCCTCAGAGCGCCACTCCGTACCAGCGGTATGTATGGCCC
CTCATGCTCAGCGTACCTCTTTGATATACTTCTGATCTCGTGA
>seq51 [SEQ ID NO: 51]
ATGATGACGCTTGGTTTTGTGGAGGCCCAAATCCACTCTTTACCTCTGACTCTGAGCGTCCTCTGCTGTTTGAAAATGG
ATCAGATGGGATCCATTGAGCCTGACAGAAAGAAAACCCCAGAGCTCGAGCTGATGCCCGCACTCTTGGCCCCGAGTCG
TCAGCCAAAGTTCCTGCCAGCGGCGGATCTTCTCCCAGAGGGTGCTCAGACGTCTACCCTCCTCCTGGGTCAGGCAGGT
TGA
>seq52 [SEQ ID NO: 52]
ATGGAAGAGAATGGCCTGGCACATTCCTACACTGGGGTGAAGTTACGGGCCAATGACACTGGCTCCCTGGCGCTGCGTA
AGCAGTCAGATGTCTGTGTTGAGTCCCAGACAGCAAGTGCGTGA
>seq53 [SEQ ID NO: 53]
ATGACCTTGTTCCTTTCCGGCCTGTACCCCAAGTGGGCCGTGAGCCAGAGCCACTATCAATCCTGGGAGGGACCCGACA
TCGCTGAAGGGACCATCGAGGATCACCTGGAGCGCCTCAAACCGGTCATGAGAGCCTTGATTAATGGTGGGACGTAA
>seq54 [SEQ ID NO: 54]
ATGACACAGTACTGGAGGATTTTGATCGTGCTGCGAATTGATCTGCCGGTCTCCTTCCTACAGTTCTATGGAGAGAGCC
CCCCTCAGTGGTTTTGCCGCCCCAAACGCTGCTTAAAAAGGTCTCGGTCGAACGGACTAAAGGCACGATGCAATTGGCC
CCCTGTTAGCTCTCGCACCTACATCAAGTTCAAGACAATGTCCTATGCTCTGAAGTGGACACCCTGA
>seq55 [SEQ ID NO: 55]
ATGATTGTGTTGAAGTACATCCTCTTGCTGTGTATTTACATAAACCTCCTGGGGTGCAGAAATGCAAAGACTAGCTGTG
AGTGTCCCAGGCCGACCATTAGGAAGTATGTCAGGCAGCCTTCAATCTCTTGTTACATGCACTGGTGCTGCCATCGGAA
CACAGGTGAGCAGACTGACAGTGGTCTTACACCCAGGCATGATCGGCGTAGCCCTGACATGGCTAAGGGTCAGCAATGG
```

```
GTTGTCCCGGCAATGGGCAGTTCCGGGGGCCATGAGCCGAACTCATCTGCATACTTATGCTCCAGAGGAATATACTTCA
GAGACCGGAATGAATGTGCCGAGGGCCTGCTCCACACTTGGCCCCTGGTGTATGACTTCGTGATAGAACTAACACAACG
GTTCCCTTACAACTCCTCGGGTCACGGCATTGAAGACATAGAATCCTTCAAAAATTGGAACTTGTACCGGACTTTCGTC
ATCTCGGAGGGCTATAAACTACTGAACATCAAGAGATCACCAAAGTCTGAGTTATGCTCAGGACGTATGGCTTTTTCTT
TCCTCCGGCTGTTTCTGTTCCACAAGAGACAGCCCCGTGGTAAAATGGCAATGCGCTATGAGGGCAAGTGGATCTTTCG
TGGGGAAGGCACAGAGAGTGGCGTTGTCCCTCTCAGGGTCGGACTTTCCAAGAGCGCAGGCAAAGATAGGATGTGTCAG
ACCCCCATGACCTTAGCAACCAAGGGTCGAAATACCCGAGGCCTGCAGGGCTACCGCCTCATCAAGCTGAAGTGTGCTC
ACCTGTGCCGGATGGATGATCAGGAGAGGGCGGTCCGGGCCATGGCCATCCCATTCAATGGCAAGGGTGGGGTGACACT
GTCTATGCTGTAA
>seq56 [SEQ ID NO: 56]
ATGAAGCTTTGTCCTATGAGGTGGCTAGGCCCGAACAAGCCAAACAACCTCCACCTGTATTTGCCGCCTATGGTCCCAT
ACCGCCACGGATTGAGGTGCACATTTTTCAAGGCCGACTTCTGCAGGGACCCCTGTTGGACAAATATGTGGCCAATCCT
CAGGCGAAATCTGATTGCGCAGGCAGGGCTGTACTGTCCGTTTCAGGTCCCACTCCTGGAGATGTCTGATTTCTCCGCT
AACCGAGAAGAAATCTGGGCTGCCTGA
>seq57 [SEQ ID NO: 57]
ATGCCGGTTGCGCGGTATCCCAGTGACAGTCTCAAACTGTCTCTGAAATCCAAGGCCTGGGTGTTCCATCAAAACCCTA
CTGGGCCCTTCACGACAACCCGGCCCGTCGGCCGCCTGCAGGGGCGGCAGCAGCCCCCCCTTGGAGGTCAGAAGAAGTT
GGCCGAGGAGCATCCTAGACGCTCCCTGGCCAAACTGAAATCGGCTGGGGCGAGCACTGGGGGACTTAATATTGGGGAT
GATCGGACCTTCCCGCTGTGCACGTCGGCCTCGCTCAGCAGACCCCTCAACCCTAAGAGTAAACAGAGCAACATTATTT
GCATCTCCTGA
>seq58 [SEQ ID NO: 58]
ATGACAGGTATCTTTTGCTCTTATGCCACTAAAGCTGGAACTGCAATGTCCTTGAGATTGCCCCCTGTAAAGGCCAGCA
ATGCCTGTGACCTGAGCCCTGGAACATGTCCTCAGGACCTAGATAGTGAAATGATCAATCACCAGTATTGGAATCGCCT
GCGGCAGATTCAATGCGGTTTGAAATCTATTGACATCTTTGTCAAACTAAGACCTTCTGTCAGCTGA
>seq59 [SEQ ID NO: 59]
ATGAAATACCGGTGCTTGGGGCAGCTCACTGCCTCTTACACCATGGCGGAATATTTGGCATTGGCAAAAACAGGATTAT
TTCCCAATAGGGGTTTTCCTCGCAAGACAGAGGGGACTTGGGAGTCCAGCCTGCCTCAGTCCTTCGAAGATAGGGGAGG
CTCAGGACGCCTGACCTCACTGCACCAGTTCCCTGATGTGATGGCCAAAGAGGACCGGAAAACCGAGGACTTTGCGGTC
AGCTCTCTCCCAGAGATCCAGCGCGTCTCCACGGGCCGGCCAGATATGAGATATATGCCGGAATACATTGATAATGGCC
CCGGCAGCAACTGTGTGTTTTAG
>seq60 [SEQ ID NO: 60]
ATGGACGGAGACTCCCACTATCGCACAGGGGGGACCAAGCAGGATACCCTGGTCCAGTACACATTGCTCCCTGAAATTG
ACTTTTTCGGGGGGATTGCTCAGAATATGATGATCATGCGAGTTGCCAGAACCCCCCCATTTGTTGCAGAACACCGTCA
GCTTATGCAGGATGGAGGGCCAGAGCAGAGAAATATGGAGGCCCGTGAACCAGCCCACCGGCTCACTAAGGCGATGTAT
GTGTCATGCAAAGCAGAAGTCAAGGGGATGGTGACGAGCCTCTCTGGGGTGCCGACCTGCGGCCTGCCATCGGAAAAGG
AGTGA
>seq61 [SEQ ID NO: 61]
ATGCAGATGATTGTCCCAAGTGGGGAGACAAAGATGTACCCTCCGCTGGAGGCCCTCCAGGAGGATGACTGTATCCAGG
CCCAGTGGCTGCACACAACCTCCCAAAGCTTCCATGAGTTAGTGTTAAGGAATGCAGTCCGCACACCATCAAAGGTTAC
CAAATTCCCTTGCAAAAAGTTCTGCGTCATTTGA
>seq62 [SEQ ID NO: 62]
ATGAGCTGCCCTTTTCTTCTTCGTGGCATTCAGATGCCTTCTCTGGAGAGAACCTTCGTGTCAGATCCTGGCTATTCCA
TCCATTTTGGATCTGAAATGCTTGATGTTGCTCATCTTGCTTCTGGCACAGAGCAAGTCCACTGGGCGACACTAGAATG
TGACTCGCAGCTCGGAAGGACACTTGAGCCTCTTGAGGAGATCACTCTAAGTTGGGTGTTGTTCCTCCTCAAGTTCTTT
TCAGAAGACATCTGGAAACTTAAATCCAAAGAACGTTCCGGCGATGACATGCTTGAGAGGATCACATCAATGGAGCTCT
TGCTGCCACTGAGACGGCTAGAACAGCTAAGCTTCTATTCCTTCTTCTCAGTGTACTGCCCTTCGCCGGAGCAAGAC
CAGCCCACCAATTCCTCTGTGCGTGTCCCTGGGCAGTTGCCATAAGCAGCAAAGAACCTGGCTGTACAATGCACTGATC
AAGTACGGGGCTTCGAGGAGAAGGAAGGTCCCCAAGCGGATGCCCATTGAGAGTCCGTTCAGCCTTGATGAGGAGTGTC
TTCCATTTTCAGTAATGCGGCAAAGGGAGACACGGACAATTGGCCTCACACCCATCATGCAGTTCCTGACCTGTTCGCC
CGTAAAGAGTGTGGATCCGAGCCGGAGGGCATGA
>seq63 [SEQ ID NO: 63]
ATGATCACTGCCAAAGATGAGACCAGATGTCTGCATTCCTCCCGAGTAGATCGGTATCGGACACTTGCGGACCCGATGT
CTGAGGAGATGTCGTGTTGCCTCCTGGTTGGGCGCGTTCACGCCAAGGGCCTCTTTGACAAAATTGTCCTAATCCAGAA
TCCCTTCATCCTCCACGACTTTTTCATGCGGTTCCCTTCTCCCTCCCAGGTACCTCTATATCAGCGCTACAAACAAGAC
CTTGATAAGGACCTGTGTTCCAGCCTGCCTTGGTACTACAACCCGAAGCTGCGGCAGCGCACTTCGCAGCTCACCTACA
AGCTCCGCACAATCTCTGTTGGCCCAAGACAAGACCATGGCGAAGACGTCTCTCCCAATGCTGACTATTACCCAGGT
GACTGCACTGAGCGACCTGAGAATTTTTTTCTCTGGATTTGGGGAGGACCTCCCCCTGGAGCCCTTTTTCTCACTCCTT
TCGTGTTATCGGTGCGCTTTCTGGGTTTTACAGTTCCTGCTCCTATACAAGGAATGGCCTCAAGTACAGCAAGGCGCATG
ACAAAGAGTGTCCATGGCCCTTCATGTCCAACTTCCCACATGCCCGGGCCTGTCGGGGTTGGCTGTTTTCGTGCTTCAG
AAAGACAAGAACTTTACCCTCATTCGACAGCGTGAGGGAGATAGTCTTAGCCTCAAAGTCCTCCGATAGGTACATGAAG
CATTCAGTGCATCGGAGCTGCAGTTCAACAGAGGGTGCCGAATCCAAGACGAGCCTGGACTGTCTTAATTCAATGCAGA
AGAAGAAGCGTAGAGATGAAGAATTACTCCAAACAAATGAATTTATGATCTCCTGTGGATCCCTGGCTGTGCAATACCG
```

```
AAGCATCTCCGGCATAATTTATTTGCTCCGGGAGCAGCATTACATGCACCAGACCCGCACCAGTTTTCAGTTTACCCAG
GACCAATCGTTCCTGGCTCGGGAGAATCACAATTGGGGGGGTGCCTCTAATGACTACCTCCTGCGCGAGAAGCTGGATG
GGAAGCCAATGAGAGGCATGATGCTGTCCCAACACAGCGTGGCATGTGGTTTGCAGGGCAAACCCATTGCAACCAACCT
GTTCAAGCCTTCAGTGAACTTGGCAGAAGAGTTGTCTGTGAAATACACTGGAGCTTTCCTGCGCTCAGACGCCCTGCTA
CAGCTGGCTCAGGCCGGACTGTGGCCCCAGAAGCCGTACCTGATTTGGAGAATCAGGGTGGAAAAGACCCACGAATGGG
GCACGGGTGAACTGGCGCTGAGCATGGTCCTGAGCTGCTTAGACTGA
>seq64 [SEQ ID NO: 64]
ATGTGCTATCCATCGCCTGACTGGAGAATTGTGATAATAACCCAGTTACTGAATACGAGATGGATCGCAGTCAGGGCAC
TCTTCATGGCAAGTGGACGCAAGCCTTGTTCAAAGGTGATCCAAGCCGCCATTGCCTCAATGGCACAGCTGCTCTATGT
GTCAAAGGCCAGCACATTAGTAGGGTCAGTGATGGAGGGAAGCGAGGACTGCAGTTGCGAGTTTCCTGATATGCCTGGT
ATTATGGGAGATGTCCCTTCCCCAATGTTCACTCTTGGCATGATCCTGCCATTAACCTTGTTTCAATAA
>seq65 [SEQ ID NO: 65]
ATGCTGACACTTTGCATGATCCTCCAGGCCCCGACAAAGAGAATGATGGATGGATCTGAAAGTGGAGTGTTGCAGTTCC
TGCGGAGTCGCTACTCAGGGTACCTGGGAGATCCCATGGCATTTCTCGAGGATGATTCCAGAAGTAAGCCGACGGAGAG
AACCGGCCTTCCTGTGGAGATCCACATGATGTCGTTTCTGGAATACCATGGTGAACTGGTCAACTTCTTCTGGCGCAGA
AGGCAGCTTCAGGACGAAGGACTTTAA
>seq66 [SEQ ID NO: 66]
ATGCACAGGCCACTGGGGACTAACAAGGGAAGTGCCCCAGTGGAGGGTTACTCTCGTCGGCCCAGGCCAAAAAAAGAGC
CAAATTCCCTCGGCCGCATGTTCTGCATCCGCTCAGCTTCGAACACCAATGAGCCTTACACCTTAGATCCTGAAGACTA
CATGAAAGCAGCGGGAGAGTAACTGTGGTCCCGGGAAGCCCAGCAGGCCTGACATCCAGAAGTTACTTAGAAGCGCCC
CCAGGGGAACAAACACGGGAGCGGCCCTTAGGCATTTTGGTCCCTTATATGCGAGCCCCGAAGAAATACTCTGACTACC
TGATGACATTCTGCACGCGTAAGCCCTTCCATAAGTCCCCATGA
>seq67 [SEQ ID NO: 67]
ATGCACTTGCACTACGATCGCATGTTATTTATGCAGCACGAAACGTTGGTTATATCTATTTCGCAGATCAATGACCTCT
CTTGCACCACGTCACCAGCCACGATGGGCAGGTGCATAACCTGGGGCCCACGAGGACAACTTTTCTGCTCTTTCGGGA
GACTGATGTCAGCCACCTGTGTTTGATCAAACAGCTGAGCTTCTTCAGTCAGATCCTGCAGTACAAGCAGCTCATGTCG
AACATATCGGAGCGCACGGGACGATACATCAGAAGCTACCATCTCTAA
>seq68 [SEQ ID NO: 68]
ATGAGGCACTACCCTGCTTGGCAAGCCTCAGCCATGCTCTTTGAGTACACTGGGGATGGTCTCCAGCAGTCCCCTAGTC
TTCTGAGTCTGGGCTCAATTGCCAATACGGTGATCATACGAACGGACCGGGCCCCACAGGAGCGAACGTCCTGCCATAA
TGGTGACCTTATCAAGAGTGCCGGCACCTCCCTGCTGGATATGCGAGATCCGCATGTGTCAGCGGAGGGAGTGACTCCC
TCGAACCTGATGATCTGCAAGACTCCACCCTCTGGTTTCTGCCTGTCTCACTCGGACTGCTCTGGAGAAAAGCAGATGG
CTCTGAGAATGTCAGCCAGCAATATCTTTCAGGGTCGGAAAACCCGGCCTCTCCTTGCCAGTCGACAGCTACCTGCAT
TCTCTGGTACTCCACCTCAACCCGTGCTGACTATATTCGGCAGTTTTACCTGTGCACCCGAGCGAATGGGCGAGCTCCC
CGCCAGAACTGCATTGGCATGGGCATACTGTCATTGTATTCTCCGGTCCAGATCGACTCCCCTCCGCCCCAGTGCCCAA
CACCCCTGTTGAGCCTGGTCGGCCGGGTGACGAGGGAGTCACAGCAGGTTGGGGTGCAACGAGCCCTAATGCTGGGTAC
GAGCACCCCTCTGCTCAACCGCCGCAAGTAA
>seq69 [SEQ ID NO: 69]
ATGCGGATTGATGAAGGGACCCAGGAGGAGTGTGAGCTCTGCGCTCTGGGCACGAAGAGCCCAGCCATCATTTCGCCTC
GACAGTACAGAATTCGAACTGTGGGTTTCATGCTCAGCTGA
>seq70 [SEQ ID NO: 70]
ATGCTATCGGAGGCCTCGAGAGATCGCGTGACGGAAATGGCCATGATGACAGATTCTTATCACCTGCCAACCATGCCTC
TGGCCCCTGAGTACTCTGGCACGTTTAGGGAAAGCTCTTGGCGAACATCTCCACATGCGATTGATCCAGGCTGGCAGAG
CCAGGTGTGTGAGCAGCATGATAACCGCTTGAACAGGGAGTCAATCGCTCAGGTCGCTTATCAGAGGGATCTGGATG
AGCAAGAACTGA
>seq71 [SEQ ID NO: 71]
ATGTACATGCCGATTTACGAGCCCAAGATGGAGATGTCCGGTCAGCCCAGAATCGAAAAGGCCCATCGGGATGGCAAGT
TAGCGACCCAGCTCTCTTCCGAATATTTCACCGAGAAGGAGCTAGACCTGGTTGACCATGCTGAGTCTTACCCAATGAT
AGTGGGAGATTTTGGGGGCACGCCCACCAAGAATTCAATACAGACCCCAGGCGGATCGATCTACGGCCTGGCTCAGAGG
GACATCAGCTTTAAATTAATGTCCATGTCCAGCAGTTGGAAGAATGTGGGAAGGTATGCAGCCCCTTTTGCTTAGGTC
TCTTTCCGCACTACGGGAACATGGAACTACGGGAACTTCTGTTTTCCCACATGAAAGCGCGCGAAACCAGAACCACGTC
AACCGAGTCTCTGACATCCATCAGACTCAGGTCAGGCTGGTGA
>seq72 [SEQ ID NO: 72]
ATGCTGAGATACAGCCGGATGGCCATCAAGCAACAGCTTGACCAGGTGGTTTACACACGGTCCCTTTCATTCACGGACC
TCCACTTGCAGAACAAGCAGGCAGGCCCTGAAAAACATGGTAACTTCAACCTCTGGGGCCGCATCCGGGATCTCAGGAT
GCGGTGTATCCTGAAGTTCAGCTGGGGAGGAGAGGTTTTGTTCTTCAATCAAGTTGTTCCTCTGACTCTTTCTCAGTT
GAGATTGAGTTGGCAGAGGTGAGATTCCTATCCTACCAGAACTCACGGTTGCCAGCGCCACGCACCGACTATCTGAGTG
CGAGCCGCACTTCTAAAACAAGCTGTTCTCTGCGCGTGTTCATATTGGGACACCAGCTAAACTGCCCTCTGTGCACTGC
TGCTTCTTTTATTGAAGGGAAACTATGTAGCAACGATACTGGAGACTACAGCTGGCCGCAAGCGGGCCCCTGTAACTGG
TCCGCTTATCTGTAA
>seq73 [SEQ ID NO: 73]
ATGATTGGAAAAGATGAGATCTATATGCTGTCAAAGGGACATCAGCCAAGACGTAGGACTCTGAAGGCCTCAACCCCCA
```

```
ACCTGGTCAGGCCCAAGCCGCCCTGCACCATCTCTGTGCGGGCCACCTTAATGCTAATCTGGTTTCCCTTCCAGTGCCT
GATAGCTAAGATGCAGTTGACCCTGGAGACCTGGTCTCCCTGGATTATCTGGCTCAATCTTAAGGGATGGCCCTGCCGG
ATCCTGCCGCTTATGTACCCATCAAGAAAGTCTGCAGCTGACTACACTGACTCTGTGGAAAACTGA
```
>seq74 [SEQ ID NO: 74]
```
ATGGGGCTCTGGCGGACCCTGAGGGCCGATGTCAAGAACAGCGATCCATCCCCTTTACAGAAAGGGACGAAAGCTAAGC
AGGTGGAGAGCCGGAAAATCATGGAGTACGCGCAGACAGAGGGGCACATCACGTTGGAGTAG
```
>seq75 [SEQ ID NO: 75]
```
ATGGCTCGGAACCTCCTGGGAACAGGACCCTTTTCGCACGAACGCCGGAACCAGCAAAACGCTGAGTTGGGAACTGAGA
GTATTATCCTTCTGGATGGAGATAGGAGAAGTGCGCGCACATCTGGCAAGAGGTTCAAGAAGGTATCTTATTACTTCCA
GTGTGACTGCCTGACGCTGTAG
```
>seq76 [SEQ ID NO: 76]
```
ATGGAGCTTCCCCGCTCCAGTAAGCCTATGACCCCGTATCCTGAGCGCAGCGGGATGGGGCACTGGTGGATTATCTATA
CCAAGCATTCCTCCAGAGGGTCCTCTAATATGATCTGCTGTGGTCCAGACTCTAGCAAATGA
```
>seq77 [SEQ ID NO: 77]
```
ATGCTCCAGGACCGCTGCTTCCTCGCAAAGTGCCTCTTATCCAGCATGTTATGCTATTACAAAAAAGGCTTGAGCGAGG
CTTTTGGCGAACCCAATGAACAGAGCTGCAACATGCGGATGTGA
```
>seq78 [SEQ ID NO: 78]
```
ATGGAACAAGGACCTGCCCTGGAGGAGGAAAAGTCAGCTTGCCAGAGCCTGACCTTCACGTTTCTGAGTCCCTCGAGAG
GCAACCAGATGCAGTGGAACTCCCAGGTTGGAAGAAACTGGACTGTACTGGTGCCAAAGGATTGTGCTAGTGTGTTTAA
GAGTTCCATGAACGGCTGA
```
>seq79 [SEQ ID NO: 79]
```
ATGCAGCAGCCGTTCGCCAGTTACTCCACCAGTTTCAAGTCAAGTGATCTGGCGACTAACTCCAGCACGCAGCTGGTCT
GTTCTGGCCATCCCTCGGGACTTCCCTTCGCTTCAATGTTCATTAGGGCTTTGTCGCCCCCTGCGCTGCGTGGCCCCCC
AAAGCTCGGATCATAG
```
>seq80 [SEQ ID NO: 80]
```
ATGCTGAGCCGGTTTCTTAAGGCCTTTCTGTTTCGGTGCTTTCAGTGTTCTGAGCGGGAAAAGGTGGTGAAGAAGCTCT
CAACCATCCAGATTGAGAAGGAGGAGCCGATCGCCCTGTCTTGTGGTAAGGCCCCCCATTCTGACCTGAACCAAGTGCT
CCCCATGTTTAATTTCGAGTTTTTTCATGGGCTCAACGTGGCCGAGAACCTGGTGTCTGGAACTGCTTCGCAGGAGAAG
GGACAATGCTGCTATGGTTTCAACAGCAAAGGCCGCTCTGTCCGGGCACTGGAATTCGTGTGTATCAGGGCCTTCAGCA
ACATCCAATCGGATGACTCCAGTGACGCCCCTTTTGGCCTGGTTTGA
```
>seq81 [SEQ ID NO: 81]
```
ATGAGCGGGAACCTCCGTATCAACCCATGGCTGACTGCCTGCATCTGTGGGGAAAAGTCGACTCAGTGTGGGCCTGCTA
AGGCCGCCAACAACAAACGCTTTCCCAGGGATCAGGCCAGAAAGCGGCTGTATTCGCCATCCCCACCCATCCTGAACAC
AATGATCCTCTCCCCTAAAAGTTGGGTCACGCTGCATGTTGCGAAGAAGCAGGCCCCCACGTGTTGGCTGCTCTCCACC
GCCAACTTAAAATTCCTTCCATCCCAGTTGCAACCGGAGGCAGATCGAAACTTTTGTAGCTCTGATTACCACCGCACTC
TCCCTTGTGCGCAGGCTATCATCACAAATTTGGAGCTGAAAATCTGGACCTCCACCAAAGCGAACAGTCCCGAACCTGT
GGCGAAAGCCCTGGAGTTCAACACGATAGTGCCATTGTGCAACTCAGAGGACCGCTTTATTGGGTAG
```
>seq82 [SEQ ID NO: 82]
```
ATGTCTCCCAACGACATTCAGGTGATTACAGGCTTGCACCAACGCTTGCCAGTGCTTCTCAACACCCTTCGTATGTCTG
ACAAGGCATTCACTCTTTGCTGCAAGAAGACCAACCCTGGCAGCCTGAAAATGCAGATGCGGAACCGTCACCCGGATCT
TCAGAAATAG
```
>seq83 [SEQ ID NO: 83]
```
ATGATGAAGAGGCGAACTCTCTCTCGGATCTGCGACATATGGACAGTGTACGGATGCAGGAAATGTAACCATTACAGAA
ACACTATTCTTCAGTCCCTGTTTCTCATCTTCTGGATTGAAATTTGTGAGGAGCATTCCCTTCATTCATCACCGAGGCA
GACCGCCTCCTCCCAGTTCTACTCACCGAGACTCAACTCCTACGAGTAA
```
>seq84 [SEQ ID NO: 84]
```
ATGGACCGCCCACACATCGTGTCCATGGCCTTTTTGAACTGCGCTTCCTCAGCGGCCATCTTGAAGGGCCATAAAATCC
CCCTGCCCATAAAGATCCTGCGCTTCGATCCACTCTCTCAAAGTACTGAATTTCCTCGGGGGTAG
```
>seq85 [SEQ ID NO: 85]
```
ATGATTTTTCACCTGCTGTGCTTTGCTACACTCGATGTGACCGTGACGCACACAGTGGCCACTGAAGCCTCGAATGGAA
TGCTGATCACGCCCTCTGAAGAAATCACCAGCACCAGGCCCGTGATATTGTGA
```
>seq86 [SEQ ID NO: 86]
```
ATGTGTGGCACAGGGTTAGTTTACCTTCTCAGATAAAACATGAAAACAACTTTTTATTTCCCGACTGGACAATGCTAA
ACAAGCCGGAACTGTACATTGGCGGGATTGAGGAGAACTACTGCCAGTACAAGGGTCCCATCTGGATCTTCAGGGTGGA
CCCGCAGTCAGAAGGCCAGCGTCTGAAGTTATGA
```
>seq87 [SEQ ID NO: 87]
```
ATGATGTTTGAGGCCTGCTGCCCACTCGCGGATTCGCAGGGGAAGAGCAAGTCCAAGGGTCTGAGGAAGGGAGAATCTA
CCCCGCTTGGAGGGGGCGGAAGTTCCTGATGCTGTCTACCAGCCTCAGCATCTACTCGTGTATTAACATGGGCCCCAT
CTCCCTTAACGCACACATTGATGATAACACACTCCATCAGACATTCATGTCGCGCTCAGTGCTTGAGCGGCTAGTTGGA
ACCTCTCAAAAGTTCGATACACACCCTCATATGTGTGCTGCAGATGCTCAGTACACAAAGTCTAGACGGTGTGAGCAGG
CCTTTTGGGCACCCTTGTCGCCTGCGCTTGTTTTCTCCATCCTCTCAAGAAATGGGCGACACCCCAAGAAAACCG
GTGTCTGAAGGGTCCCCAGTGCCTCAAGCGCTGTTGTCAAGAGTCCTGCCTCTCTGGTGGCTTTGTAATCTTTGACAAT
```

```
CCAGTCTGCTACTTATGA
>seq88 [SEQ ID NO: 88]
ATGAATGCAGAGGACATGCTGGGGAAACACTGCGCTTATGCTTTTTGCACAGTCCCTATCCCGAAGGGAGCTGTGAACT
TGAAAACCGAGTTTGAGAGTGGCTGTGCGAAGTCTGCCAACGGCAACTCCCGCAAAGACAGTGTTTCAGGTCCATGCCC
TAAGATGAGGCAGAAGTGGGACTGGGGACCCCGAGAAGGAGTGGCTCGGACAGGAGAATTCTAG
>seq89 [SEQ ID NO: 89]
ATGAGAGTGAGGGCACGGCTGTCAATCCCCTTCACCACGAGATCCATGGCCCTTTGCTACCGGAAGTCGGGGGACACCG
GTTTTGTTGTGCAGAAGGAGCCCCAGGATCGGTACACGGGAAGGAAATGTCAACCCGTACTGATGACCTGA
>seq90 [SEQ ID NO: 90]
ATGGAGAAGCTGTCCTGGCGTGCTGGCCTCCTCCACTCTCAGGATGGAATAACCAGGGCCGCCTACCCGGGAAAAGAGC
AGTCTTCCCGGGGCCGCAATGCGACCTTTTGGACAGCTCAGCCTGACTCCCGGGCGGCCTCTTACTCCCAGCTCTCTGT
CCAGAAGTATCGAACAACAGCGATGTGCCTGCCTGTGTCCATGTCTAGTAATCTGGTCTCCATGGAGCAGCGGTTCCGG
CACAAGCTCATCCAGTGGCGGTTGTGTCTGAGAATGTCTAGTCTAACCATTATGTCATAG
>seq91 [SEQ ID NO: 91]
ATGTCTTTGACAGATTTTCTTTCTTTCTGTGTTCTGAGAGTAATGGCCAAACATCTCACAGACTATAGGGCCTCAGCTC
AGCTTGGGTGCTGTGAACAGCAGGCTTCTGCATCCCGACCGGAGGAATGA
>seq92 [SEQ ID NO: 92]
ATGACGGCCTTGGGGCTGCAAGTTATAGCCGTTCTGTTGTCTATGATGGCCATCCGTCTGCGCCAGAGGGTGGGGCCA
AGCGTGGCAAGCAGGTGAAGCCATGGTTCAAGCAATTGGAATGA
>seq93 [SEQ ID NO: 93]
ATGGTGTGGCTCCTACCCCCCTTACCATTGAGCCACTGTAAGAATCCTTTCCTTCGTAAGTGCTTCAAGTTTGAGCGCT
CGTGTGCAGGAATTTCTTGCTCTGATACGCCGCCCTACTCCTGCCGTCAGGCCGAGAGCTCCACTTCATATTTTTACCC
ATTCTCAATGACCAGAAGCACCATGACCATCCCAGACCAAACCAAAACCTGCCAGGCGTGTTCTGTGACCCGGTTCCCC
TCCCGGGAGGAAAAGACCAAGAACCTGATGACATTCTGTTACAAGATGCATCTGCAGATGGTCGGCTATCCGGTCAAAG
ACACGTTCCTCAAAGAGGCCAAGGACTCTGATTCTTCAGGGACTGAGTTTGAGCTGGTGAATGGGCCACCTTTTGTGG
GCTCGGGATTCAGTTGAACTGCTGTTCCCCCAGTGCCTGA
>seq94 [SEQ ID NO: 94]
ATGTCCAAGGAGATTCATCTGCCTGTTCTGAGCCGGGCCGGACTCCCTCCGAGTTGTGAGAAGCTTCGAGGCTCCCCCT
CTGTGCTCTCCATGACATTTGCCTACCCCCTGCCCAAGCGGAGCCACCAGGCAATCGCCACGGCGTCCCGGGAGCTCAT
GCTAACCTTGGACCCCTCGGCCAAAGGACCGGGGTATTGA
>seq95 [SEQ ID NO: 95]
ATGCCCGCGATGGCCACTGGCGCGGAGTGGGCCTCTGCCACACGGATATGCGACCGTTATGCGACTTCCCACGTGAGGC
GCATGAGATCAGGGGCAAGACTGATCAAACAGGGAGTGGAGCTGATCAAGTACCGCCCCACCACTTGCCCCTACATAGC
CATGGATGCTCGCGACCTTTTGCGACACATTCGGAGCCCCGAATGGGAACCCTACTGCTACTGTCTGACAGCTATCTCA
AGCTCAAAGAACTATCTTCTGCTGTCCGTCAGGGCCCCTCCATTCTCGCAAAAGAAACGACTTCCCGTGGAGTGGGTCC
TTCAGTGTACCCCCATCTGCAAGGCCTTTCAAGGGTCAACTTCATACAAGCTGAACATGTTCTCCTCTTGCGCGCACAC
TAGCGCTTTGACTTCAAGGGATTGCAAAAAGTCAATCATGAGGCGCAACCATTGCTACTTTTATCCTTTCCTGGATGGA
GCAGGATTCCCGGGGGCCATTACATGCAAAATCAGAGGATGCATTCTGGGCATGCAGAACTCTCCGGTGGGCCGCCTTA
ATGGGTGCTGCAAGCAGTCTGTCAGGGATGATGAGACAAAGGCATTCCTGCAGCCCCGTTTGGTCGGGACGTCAATGGT
GGATTATGTGCCGCTGCAACTATTCTGGGAGCAAGTTCCGCTCCTCAAGTGTTCTCTTAACCCAATAAGCTTGAAAGCC
GCAGGGACGCAGTGA
>seq96 [SEQ ID NO: 96]
ATGTCTTATGACTTACGGTGGCTTCACCGTGGGGCCACAATCACAGCCGAAATCATCTTATCTTGTAAGCTCCCAAAAG
TGAGAATGGATTTCTGCTGGGTGAAGCAGTCCATGGAGGCCATGGTGGCCATGAAGGACCAGAAAGACGCCTTTTGCTG
A
>seq97 [SEQ ID NO: 97]
ATGACCAGAAGCTGGGCCCTGGTGCCACCCCACCTGTTGGTTGGAGCCGAAACAACCCCTGTGACTTCATATGGGTACA
AAGCGAAGAGCAACATACGCTTTGTGTTCTCTGAGGCTTTTGAGGCTCAACAGAGGCACGAAAGCCGTTCAACCAACCA
TGCCTGGGCCCAGCCAGCAGGTCGACCGGTCCATCTCATTAAGGGGCAGGAGAAATCTAGGGAAAATTTAGATCCGAGC
TGTCCCAAACCAAAGGGAGCGGACCGGAGTCTCACAAAGGATGGAACAATGAAGCAACGATACGACTTCTACCTGCCGT
AA
>seq98 [SEQ ID NO: 98]
ATGAAGTATGTTTCCCAGGAAGCCCACCTGGTCTATGTTTATATGTATGCGGATCACTACCTCAGCAGTGTGCTGTCTT
CCCAAGATGGGCGCCCCTCAAACTTCATCACGCGCCTGACAAATGCGAGTGACAAGTGGACTAACAAGACGAAGTCCAT
GAAGGACAGCTATCAGGGTTTGTGGGAGTTGCCTGGGATCCTGGAGCTGAGAGCACCTGACATGGAGCTGGAACTTCTG
ACGAATGGGAAAGCCCTGATGGCGATCCGCATGATCAACATGAAGAATTCCCGCAGGATGCCAAAGAGGCCTCGTCTG
CGATCATGGCCAAAGTTCCCAGTTTAGTTGTGCCATGCTCCGGCTACTTTGCCTGGCGGCAGAAGGGCTTGGAGCGCAA
CTTTGATCTGAAAGGCCAAAGTGTCAAATACAGAAAAAATACAGGTCCTGGCCTGTCTCCACCTCAGGTGAGGACCTCC
TATCAGGAAAACCTGGGGACACCCCTTCTGCCACCAATTCAGATGATGAGCTACCTAGTGATTTCGGACCTCCCCCGGA
GGTCTAAACGTGATTGCAGGCGGGCCCGTGGAGTCTTTGCCCCACGCGAGGGACTAGCCAAAGAACAGGGCAAAAGCAA
GCTCCGCGCAGCTTACATTCACAACAAGGGTTTCGAGGGCCTGACTCGTGAACAAGTCCAGGGGTATGCTGAGAGCTGT
GACGTTCTGCCACAGCAGTAG
```

```
>seq99 [SEQ ID NO: 99]
ATGGGCACAAAGCCCTTCTCACTCAAGGGAAAGAGCTACAAGCAGCCTAACCTGAAAATGCACCCCCTCGTGCCTCCCT
TAAACAGATTCTTGTGTCAGGGTGCTGCAGTTGCAGAGCGGAAAATGCGGTAA
>seq100 [SEQ ID NO: 100]
ATGAATGGGCTCCTGCACACGACATATAAGGAGAAGACGTCGTATCCGCGTGAGGTGTTTGGGCATAGTGCAGAAATTT
CCCGCCTGTGTCCTCTGCCTTCCAGTTCCATGGCAACCCCGCCAAATGACGTGAATATGGTGATCCCCCTCAAAAGACG
TGCGCTGACGAACACCTATGGGTCTGCTTCGATTCGTCAGATGACGCCGATTTACAACCCTACCGTCTCTGCCTGGGTT
TACTCGAGCCAAGAGGCACTCAAGTGTCGTTACCTGGGCTTCCGGCGGAGAATTGAAATGCCCTTTTGTTTTAGTGGTG
CGGCCAACAGATCCTACAACTTTTCTGCTAAGGAACGCTTGGGTCACGCACCTGCCTGTATCCGATGGCACAGATATTT
ATGGATGAACTTGGACATGAAAATGTTGACTGCCCTTCGCATCTGA
```

Figure 2

```
>seq960 [SEQ ID NO: 101]|seq posit = 113|Tm = [67.1886]|GC% = 51
aaccaatcccatcccaggtgtgcggcgaatcggtcgatctagtcctaattagccggataggaaaacctca
>seq393 [SEQ ID NO: 102]|seq posit = 59|Tm = [67.4662]|GC% = 51
aagaacccacgccgtctacatatcgggcacgtgctataacgactcaggagtatttaacgaccgcacggaa
>seq986 [SEQ ID NO: 103]|seq posit = 36|Tm = [66.6729]|GC% = 50
acaggtgtcctcaaaccagcctgaaacgttactaggtgaagaatcaccgcggttgtcggtagttaagcga
>seq535 [SEQ ID NO: 104]|seq posit = 133|Tm = [67.0512]|GC% = 50
acccgcgtacacagtaggcactctacggcgcgtttagcgttaatcaccaattttgcaatagtcaccagag
>seq581 [SEQ ID NO: 105]|seq posit = 103|Tm = [66.5507]|GC% = 50
acggactacctcggccacttcatttggcgacctgcggatattgcttacgaatctcgatcttccggattat
>seq866 [SEQ ID NO: 106]|seq posit = 91|Tm = [66.5878]|GC% = 50
agaagtcgtgtgatcgaggtagcactgggatttacgaaaattgccctaccggtatacgctaggccatacc
>seq71 [SEQ ID NO: 107]|seq posit = 58|Tm = [66.7385]|GC% = 50
agcccacatatagcccacgcgggtgtcgacaacatatgtcgtatgcgagtaacgttttcgtttgagatgg
>seq595 [SEQ ID NO: 108]|seq posit = 59|Tm = [66.7497]|GC% = 50
atactacttttgggtatgctagctacgtagtacccttcaatagccgtcgcttggtctcttgcgcgtcacg
>seq35 [SEQ ID NO: 109]|seq posit = 59|Tm = [|GC% = 66.157]
catctatctatgtaagttaccggcatgggttatggattcgtggaccgcgatgtgacgtaggggtttccac
>seq599 [SEQ ID NO: 110]|seq posit = 37|Tm = [66.4969]|GC% = 50
cattttaccgttaccgggaagcgtgtgtgtctttatttgcgcgtacccagtgttgagaacgacggaacag
>seq429 [SEQ ID NO: 111]|seq posit = 99|Tm = [66.8714]|GC% = 50
ccatccgggccataagtttatagtagcgattgttttgccctaccagcgaatcgcgcccagttagtaatc
>seq470 [SEQ ID NO: 112]|seq posit = 98|Tm = [67.7815]|GC% = 51
cccgagcttgcgctagtacgattatgtaccgctatgtcaatttgacgccctcgcactgcggcactttatt
>seq826 [SEQ ID NO: 113]|seq posit = 27|Tm = [67.2547]|GC% = 51
ccggctcggtgtcaccgcggaagtacctttgagtatcgcacttatcggctttaacctggacgtaactaaa
>seq121 [SEQ ID NO: 114]|seq posit = 91|Tm = [67.1271]|GC% = 51
ccttggatgggtaaattccctcgtctacgcgtaacaactgaacgcgtagcgcgacggtctcaggaaatta
>seq118 [SEQ ID NO: 115]|seq posit = 94|Tm = [66.4195]|GC% = 50
cctttccgtgttactcggccggcaaggacgcctcgtaccatctttgatagatgtatttgcgtaaattcgg
>seq622 [SEQ ID NO: 116]|seq posit = 131|Tm = [67.2651]|GC% = 51
cgcgaccccgactggtagttgcgcgctcgcattaccgagttcacatcgcatgtactacattagagaaata
>seq33 [SEQ ID NO: 117]|seq posit = 51|Tm = [66.6602]|GC% = 51
cggccacaactctcaggacgcatataagacgcggaaaggcatacacgtctacttagagacaccgagactt
>seq568 [SEQ ID NO: 118]|seq posit = 31|Tm = [66.9422]|GC% = 51
ctgcttaaccgttccagaggggcgttcgtatcaaaagggtgcgatttcgatcacgtcgcagtgactcat
>seq645 [SEQ ID NO: 119]|seq posit = 63|Tm = [66.3513]|GC% = 50
gaatggcatcaacggcgctgtacatagtcttctcgcctacataatagcgctagttgataggaaccagggg
>seq675 [SEQ ID NO: 120]|seq posit = 145|Tm = [66.9231]|GC% = 51
gagctgcacacccgcagacatcatagtgagtgtaatcacgcacgtgaccagttaacccatttcgtggaga
>seq799 [SEQ ID NO: 121]|seq posit = 55|Tm = [65.8952]|GC% = 50
gatggattcacgaacgagcacttagtaacgcctggtactgacatcttattgcacgtagtggagagcctgg
>seq1 [SEQ ID NO: 122]|seq posit = 70|Tm = [|GC% = 65.843]
gcaacgaccagctacctgttaaccgtatatcagagtcgaatgctcgcggtactgttcgaagtactcatcg
>seq683 [SEQ ID NO: 123]|seq posit = 85|Tm = [66.3914]|GC% = 50
gcagaattcctaaccatgcaagcgtggcgactcgtctctcgcaaagttctatacgaatcagcgatggta
>seq781 [SEQ ID NO: 124]|seq posit = 126|Tm = [|GC% = 65.787]
gccctctcgtcccacgttcgctcgtcttgttgacactactgacgggtatccctctaaatacttctctttt
>seq799 [SEQ ID NO: 125]|seq posit = 236|Tm = [66.3829]|GC% = 51
gcctcttcgatggggtccgtctggtcagtaccgacgaaaatgcgacggtagatgtcagaattgattctgt
>seq567 [SEQ ID NO: 126]|seq posit = 117|Tm = [67.3478]|GC% = 51
gcgggctcttgtgcaaacttatggggctagtgactcgggtgtagcacgttttgcgaagactaagacagta
>seq610 [SEQ ID NO: 127]|seq posit = 106|Tm = [|GC% = 66.353]
gcgtctatgacaggtcgggcacttaggcggcgacgcttgatgtttgagtcgcagatattagtttataagg
```

```
>seq480 [SEQ ID NO: 128]|seq posit = 71|Tm = [66.6889]|GC% = 50
gctatctaacgcggtcttgccaatactacgaatggttgctacaggatatcgagtaccgcaaaatgggggc
>seq855 [SEQ ID NO: 129]|seq posit = 33|Tm = [66.1915]|GC% = 50
gggggcaactctccaaccgagcgtgaatccagcgattattatcctactccatactattagcgggtatacg
>seq892 [SEQ ID NO: 130]|seq posit = 56|Tm = [|GC% = 67.231]
ggtacgaatctcccattgcatggacaaatatagtccacgcattggacgcacccaccgatggctctccaat
>seq65 [SEQ ID NO: 131]|seq posit = 31|Tm = [66.6237]|GC% = 51
ggtcgtacccaacctgacacgagatgtcggcgctcgtttcgattggacgatcggatatatgatcaagcaa
>seq435 [SEQ ID NO: 132]|seq posit = 133|Tm = [|GC% = 67.453]
ggttgttccatgtactcgatactacctaggcatcaggtgtatacgccggtttggatgggcgttcggcaaa
>seq552 [SEQ ID NO: 133]|seq posit = 80|Tm = [66.5367]|GC% = 50
gtgccaccccaattagtcttttgtccgggccaagagtacgacaacggggtattttggtactatatcccac
>seq391 [SEQ ID NO: 134]|seq posit = 24|Tm = [66.0311]|GC% = 50
gttaagggtctcgaaagatttctactctcgacgtaccgttggcagcgcactaagaacgggtaatgtgctg
>seq886 [SEQ ID NO: 135]|seq posit = 144|Tm = [67.8701]|GC% = 51
gttaggcacttgcgcgtcaagcgcgcaaaccctaattacgttctgtccacgcgctagggatattcgtata
>seq80 [SEQ ID NO: 136]|seq posit = 117|Tm = [66.4445]|GC% = 50
taagatgcctgacgaaaaagtcccgtgtacccacaacggaaagcgtgatctagatagttcccttagcgcc
>seq732 [SEQ ID NO: 137]|seq posit = 53|Tm = [67.4631]|GC% = 51
taattttgggttgtcgaggcataaactggtatgctcgtctcgctcgacgagcggttgaacgcctatcgct
>seq597 [SEQ ID NO: 138]|seq posit = 84|Tm = [|GC% = 66.526]
tattggccgcggcgctaacttatatcgagagatgtctagtttccccacccgttacatattctacggggag
>seq534 [SEQ ID NO: 139]|seq posit = 134|Tm = [67.5222]|GC% = 51
tattttccggtactgagtggaacgacatgaagttggcggtcaggtcgttatttcgcagccacgcaccact
>seq860 [SEQ ID NO: 140]|seq posit = 43|Tm = [66.5685]|GC% = 50
tcagatgtcgttattaacgggaaggtatccggttcactatacggcgattacttcgcgttgcgaaagggc
>seq501 [SEQ ID NO: 141]|seq posit = 65|Tm = [67.1596]|GC% = 51
tccggctccgcagacggtttaactcgaaccttaaaagtcgtgtgaagctacttcgagaccatgcgctctt
>seq775 [SEQ ID NO: 142]|seq posit = 54|Tm = [67.0808]|GC% = 50
tctgttacccacattgtcaccacttgacaggcgcacggtcgtttgtaaagcgactagctacgcaggtata
>seq49 [SEQ ID NO: 143]|seq posit = 30|Tm = [67.6598]|GC% = 51
tggagatgcgaacgttgggagtatcaatcccggtgcaaccccctaatccgacatgccgcaagtatatat
>seq554 [SEQ ID NO: 144]|seq posit = 103|Tm = [67.6507]|GC% = 51
tgggcgcctagagccagcatattacaggcgagctgttttcgcgtctctaatgacgtgtacgcgattctat
>seq983 [SEQ ID NO: 145]|seq posit = 52|Tm = [66.6572]|GC% = 50
tgtagacagggcgcgattgtatgggacagtttacgcactaaccgactctacaatgtagtgtttgtcggc
>seq631 [SEQ ID NO: 146]|seq posit = 32|Tm = [|GC% = 67.493]
ttccgcatgagatcaacgcgtggtcaatacgtgttaagaaccggtcgacgccagctagacctaatgcgtt
>seq397 [SEQ ID NO: 147]|seq posit = 120|Tm = [67.7733]|GC% = 51
tttcgactgggggtacaaagctccctatttgccgttcacgaagctacatactggtctagcgcgtgcacaa
```

Figure 3
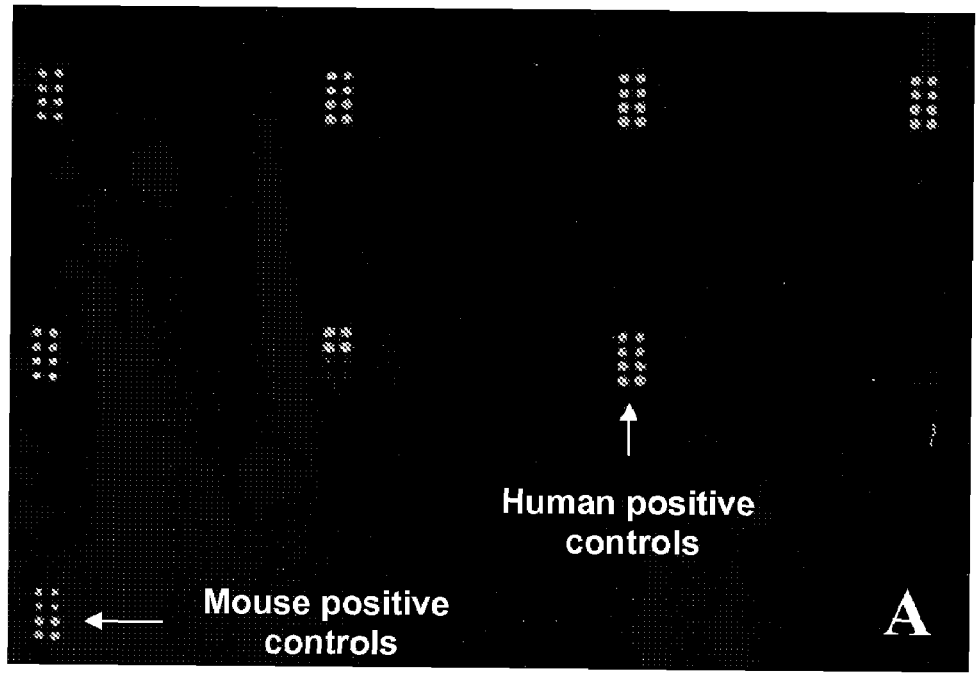
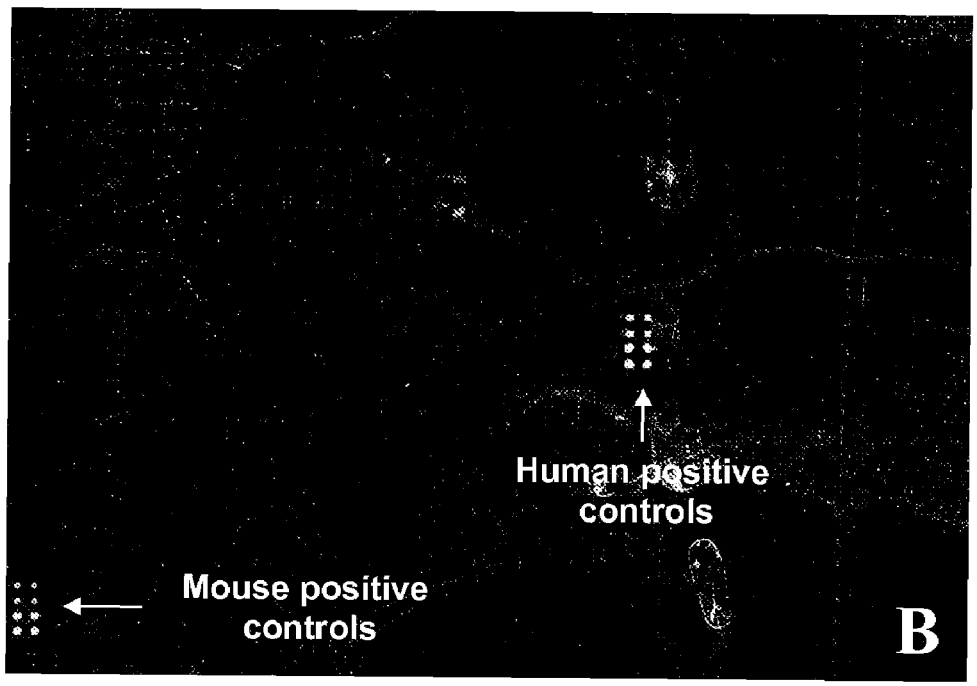

Alien Gene A (321 bp)    [SEQ ID NO: 148]

```
        T7 promoter                    A0429
5' TTCTAATACGACTCACTATAGGG|CCATCCGGGCCATACGTTTATAGTAGCGATTGTTTGCCCCTACCAGCGAATCGCGC
                                                          A0732
CCAGTTAGTAATC|TAATTTTGGGTTGTCGAGGCATAAACTGGTATGCTCGTCTCGCTCGACGAGCGGTTGCACGCCTATCG
                           A0552
CT|GTGCCACCCCAATTTGTCTTTTGTCCGGGCCAAGAGTACGACAACGGGGTATTTTGGTACTATATCCCAC|GCGGGCTC
        A0567
TTGTGCAAACTTATGGGGCTGGTTACTCGGGTGTAGCACGTTTTGCGAAGACTACGACAGTA|AAAAAAAAAAAAAAAAAA
```

B

Alien Gene B (322 bp)    [SEQ ID NO: 149]

```
        T7 promoter                   A035
5' TTCTAATACGACTCACTATAGGG|CATCTATCTATGTCAGTTACCGGCATGGGTTATGGATTCGTGGACCGCGATGTGAC
             A0860
GTTGGGGTTTCCAC|TCAGATGTCGTTATTATCGGGAAGGTATCCGGTTCACTATCACGGCGATTACTTCGCGTTGCGAAAG
                           A0732
GGC|TAATTTTGGGTTGTCGAGGCATAAACTGGTATGCTCGTCTCGCTCGACGAGCGGTTGCACGCCTATCGCT|TCCGCAT
        A0631
GCGATCAACGCGTGGTCAATACGTGTTTAGAACCGGTCGACGCCAGCTTGACCTACTGCGTT|AAAAAAAAAAAAAAAAAA
```

C

Alien Gene C (322 bp)    [SEQ ID NO: 150]

```
        T7 promoter                    A0781
5' TTCTAATACGACTCACTATAGGG|CCCTCTCGTCCCACGTTCGCTCGTCTTGTTGACACTACTGACGGGTATCCCTCTAA
              A0391
ATACTTCTCTTTT|GTTAAGGGTCTCGAAAGATTTCTACTCTCGACGTACCGTTGGCAGCGCACTAAGAACGGGTAATGTGC
            A0534
TG|TATTTTCCGGTACTGAGTGGAACGACATGAAGTTGGCGGTCAGGTCGTTATTTCGCAGCCACGCACCACT|CGGCCACA
        A033
ACTCTCAGGACGCATATAAGACGCGGAAAGGCATACACGTCTACTTAGAGACACCGAGACTT|AAAAAAAAAAAAAAAAAA
```

Figure 6
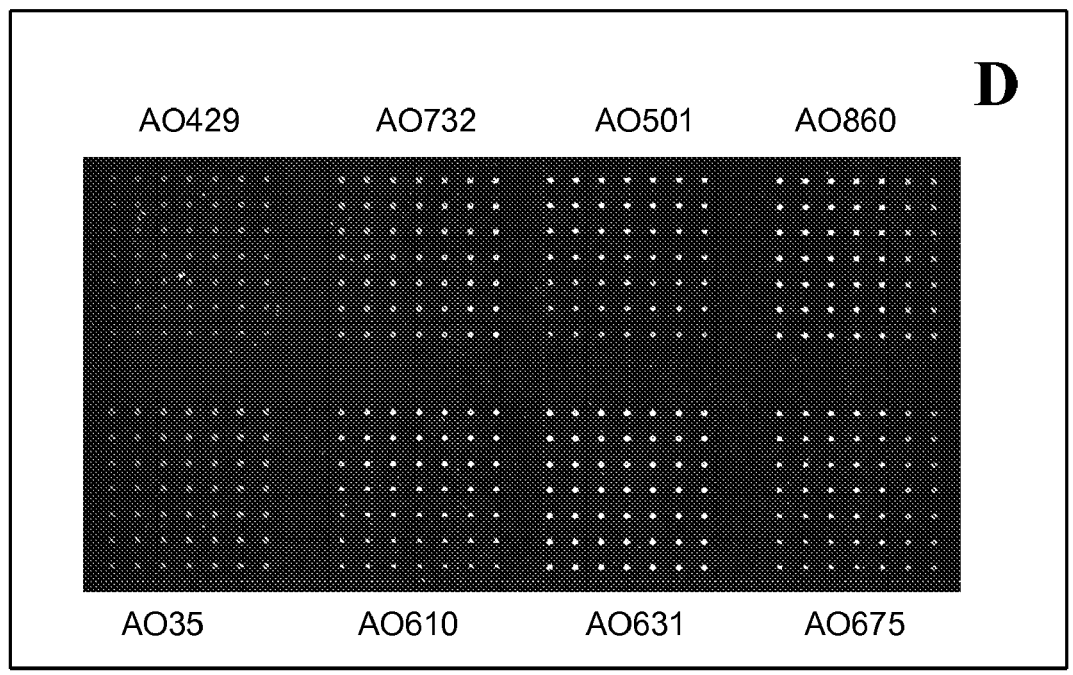
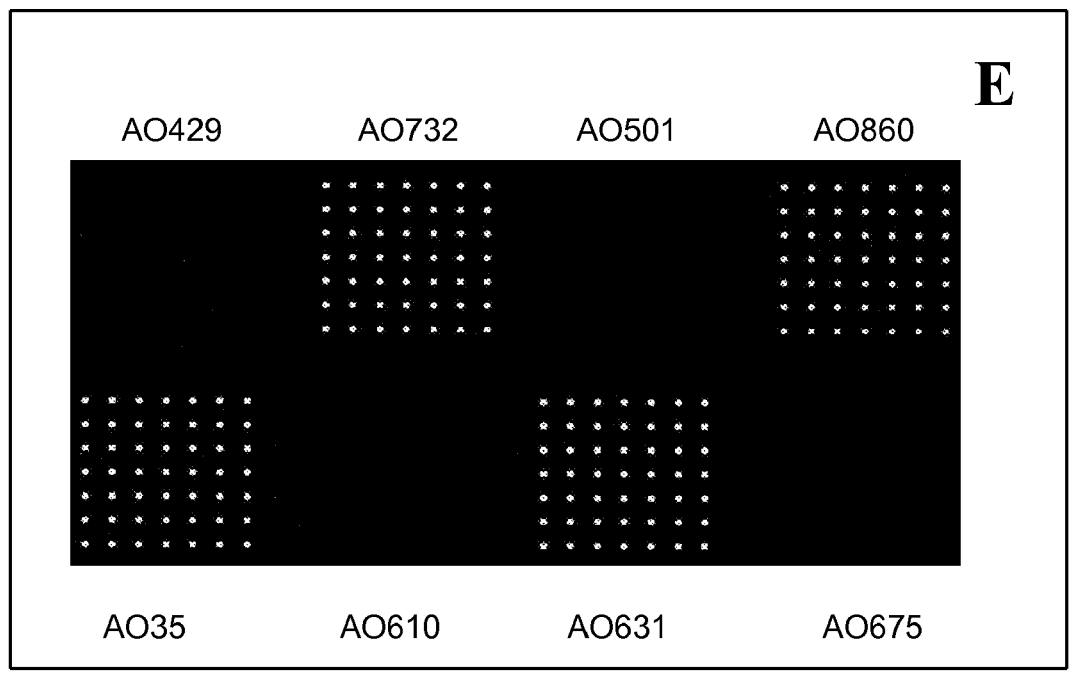

Figure 9
A. 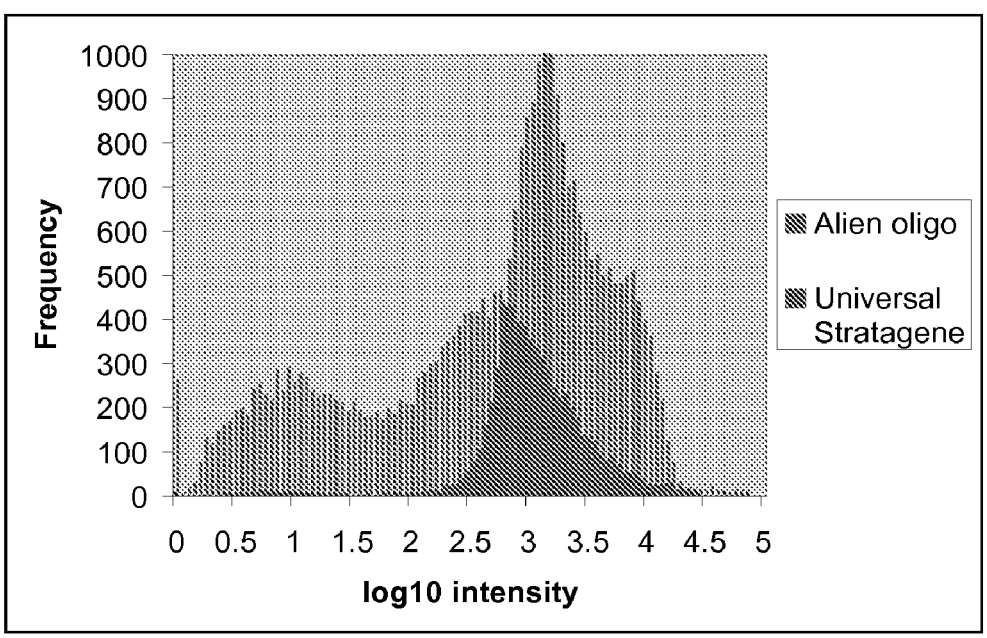
B. 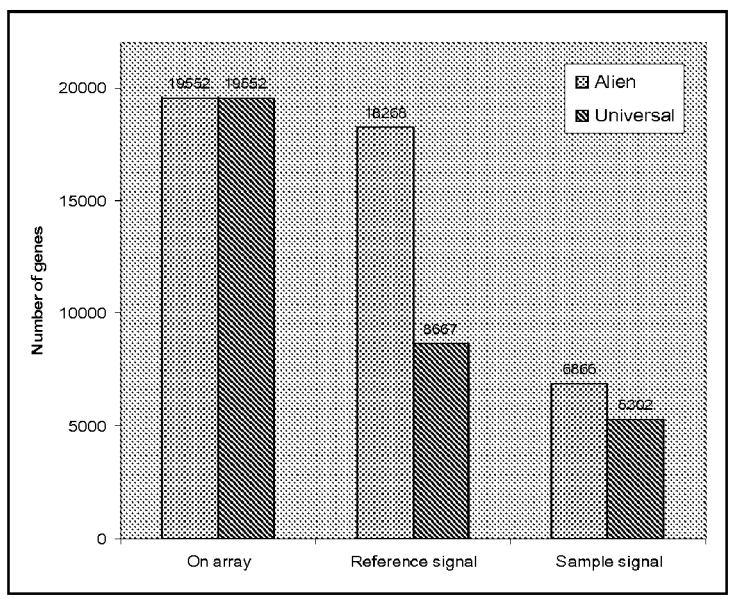

Figure 10
A.
B.
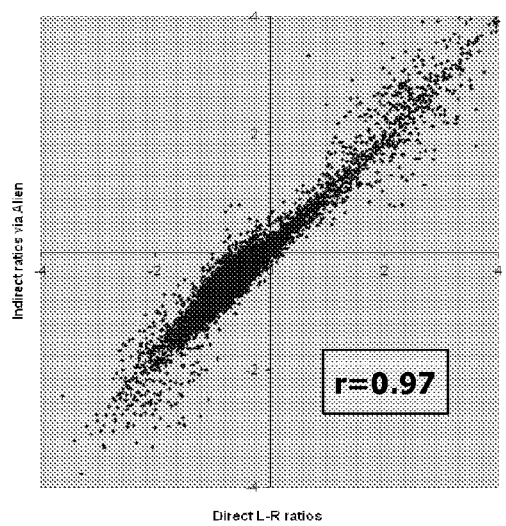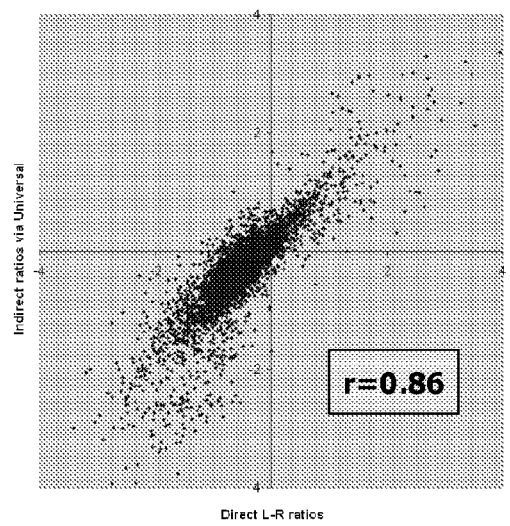

ALIEN SEQUENCES

RELATED APPLICATIONS

This application claims priority to Provisional Patent Application No. 60/441,832, filed Jan. 22, 2003, U.S. patent application Ser. No. 10/763,039 filed Jan. 22, 2004, and PCT International Application No. PCT/US04/01911, each of which is incorporated herein by reference in its entirety.

BACKGROUND

The proper and harmonious expression of a large number of genes is a critical component of normal growth and development and the maintenance of proper health. Disruptions or changes in gene expression are responsible for many diseases. Using traditional methods to assay gene expression, researchers were able to survey a relatively small number of genes at a time. Microarrays allow scientists to analyze expression of many genes in a single experiment quickly and efficiently. A microarray works by exploiting the ability of a given mRNA molecule to bind specifically to, or hybridize to, the DNA template from which it originated.

DNA arrays are commonly used to study gene expression. In this type of study, mRNA is extracted from a sample (for example, blood cells or tumor tissue), converted to complementary DNA (cDNA) and tagged with a fluorescent label. In a typical microarray experiment, cDNA from one sample (sample A) is labeled with a first dye that fluoresces in the red and cDNA from another sample (sample B) is labeled with a different dye that fluoresces in the green. The fluorescent red and green cDNA samples are then applied to a microarray that contains DNA fragments (oligonucleotides) corresponding to thousands of genes. If a DNA sequence probe is present on the microarray and its complement is present in one or both samples, the sequences bind, and a fluorescent signal can be detected at the specific spot on the array, where the DNA sequence probe is located. The signals are generally picked up using a "scanner" which creates a digital image of the array. The red to green fluorescence ratio in each spot reflects the relative expression of a given gene in the two samples. The result of a gene expression experiment is referred to as a gene expression "profile" or "signature".

This technology, though widely used, is not without its problems. Almost every procedure in the methodology is a potential source of fluctuation leading to a lot of noise in the system as a whole. The major sources of fluctuations to be expected are in mRNA preparation, reverse transcription leading to cDNA of varying lengths, systemic variation in pin geometry, random fluctuations in spot volume, target fixation, slide non-homogeneities due to unequal distribution of the probe, hybridization parameters and non-specific hybridization. Some of the errors mentioned above can be minimized by performing replicates of experiments or by using a flipped dye design.

Biological replicates are arrays that each use RNA samples from different individual organisms, pools of organisms or flasks of cells, but yet compare the same treatments or control/treatment combinations. Technical replicates are arrays that each use the same RNA samples and also the same treatment. Thus, in this setting, the only differences in measurements are due to technical differences in array processing. The rationale for the flipped dye design is that it allows for the estimation and removal of gene specific dye effects. These dye effects have been shown to be reproducible across independent arrays by the use of Control vs. Control arrays. Any deviation from a ratio of 1 in these arrays is due to either dye effect or residual error. However, none of these methods will account accurately for chip manufacturing error.

Therefore, there remains a need for the development of improved microarray technologies, and particularly technologies that allow researchers to control for errors and/or to normalize signals.

SUMMARY OF THE INVENTION

The present invention provides reagents and methods that are useful in normalizing and standardizing data from nucleic acid hybridization studies, and particularly from microarray-based hybridizations. The present invention teaches that it is useful to define nucleotide sequences that are "alien" to the sequence population under analysis. Such alien sequences may be included on microarrays and will not hybridize with the nucleic acid population under study. Alternatively or additionally, sequences complementary to the alien sequences may be mixed together with (i.e., "spiked" into) the hybridizing population in order to control for processing and hybridization events.

Use of the alien sequences (and/or their complements) according to the present invention provides a number of advantages. For instance, when an alien sequence is included in a microarray and its complement is not included in the hybridizing sample, the alien sequence may act as a negative control, revealing defects in hybridization conditions that could affect the experimental outcome.

Furthermore, when an alien oligonucleotide is present on an array, its complement may be added to the hybridizing sample, and processed and hybridized together with that sample, as a control for the processing/hybridization steps. If the alien oligonucleotide is present in spots at different locations on the chip, this strategy can also be used to control intra-chip hybridization variations.

Moreover, when the amount of anti-alien spiking nucleic acid (and/or alien oligonucleotide) is known in advance, the degree of anti-alien/alien hybridization may be relied upon to establish the amount of non-alien sequences present in the hybridizing sample based on the relative extent of their hybridization to complementary oligonucleotides. In fact, in some embodiments, multiple alien/anti-alien pairs at different amounts are utilized in order to provide multiple points for comparative quantitation of other nucleic acids. In certain preferred embodiments, the alien sequence probe and the probe detecting the target sequence to be quantified are mixed together in the same spot to allow in situ comparisons. This approach also provides a consistent standard (the fixed amount of alien probe) that can be relied upon to allow inter-slide comparisons and inter-experiment comparisons even when the experiments are carried out using rare samples (i.e., in a situations where the number of experimental replicates that can be performed for control purposes is limited), or over long time spans, etc.

Thus, alien sequence probes and their complements can be used to normalize the data obtained from array hybridizations. For instance, if every spot in an array contains a defined ratio of experimental probes to alien probes, the presence of the alien probes allows the researcher to control for variations between or among spots (e.g., by hybridizing the array with a sample containing anti-alien sequences that are differently labeled from the nucleic acid sequences under study).

Additionally, the presence of alien probes in microarray spots allows researchers to assess the quality and consistency of microarray fabrication and/or printing/spotting techniques. For example, when alien sequences are present in all or a representative collection of spots, the presence or absence of particular spots, overall spot morphology, and slide quality can often be assessed by hybridization (in parallel or simultaneously with experimental hybridization) with an anti-alien nucleic acid. Even random spotting of alien sequences can provide information about the overall integrity or uniformity of a slide. Often, however, it will at least be desirable to include alien sequences in one or more spots containing experimental samples so as to provide a direct assessment of an experimentally relevant spot.

DESCRIPTION OF THE DRAWING

FIG. 1 shows 100 sequences identified according to the present invention as "alien" to mouse cDNA.

FIG. 2 shows about 50 oligonucleotides identified according to the present invention as alien to mouse cDNA and useful for hybridization applications.

FIG. 3 shows that inventive alien oligonucleotides, selected as alien to both mouse and human cDNAs, do not hybridize with commercially available universal mouse and human mRNA sets. The presence of alien oligonucleotide probes on the slide is demonstrated on FIG. 3A, by detection of fluorescent signals over the whole array, after enzymatic 3'-OH labeling with terminal deoxynucleotidyl transferase in the presence of dCTP-Cy3. FIG. 3B shows that in the absence of such treatment the alien probe sequences failed to yield appreciable signal intensity above background threshold, while the human and mouse positive control sequence probes were detectable.

FIG. 6 illustrates the inventive anti-alien in-spike control concept. Panels A-C show sequences of alien genes designed by linking four 70 mer alien sequences together. Panel D shows a microarray containing four alien oligonucleotides whose sequences are present in one of the alien genes, and four that are unrelated. Panel E shows that cDNAs corresponding to the non-coding strand of the alien gene hybridize with the expected alien oligonucleotides on the chip, and not with the unrelated alien oligonucleotides.

FIG. 9 shows a comparison of the use of alien sequences as a reference to Stratagene Universal Mm RNA. FIG. 9A shows the $\log_{10}$ intensity distribution of the reference channel. The Universal Mouse RNA channel is labeled Cy5 and Cy3 in different experiments and is normalized for dye effects. The aliens were labeled with Alexa488. The alien hybridization intensities are within the range of the scanner. FIG. 9B shows a histogram depicting the number of spots in the final analysis as compared to the total number of spots on the array. There are totally 19,552 spots on the array. Hybridization signal intensities were measurable from 18,268 spots in the case of the aliens and 8,667 spots in the case of Stratagene Universal RNA. Of these, 6,866 alien spots and 5,302 universal spots were used in the final analysis for indirect comparisons.

FIG. 10 shows the $\log_2$ ratio of hybridization signal intensity of mouse liver mRNA to macrophage RNA. Comparison of ratios measured from direct comparison on microarrays to (A) indirect ratios using alien oligos and signals as reference and (B) using Stratagene Universal Mouse RNA as reference. The correlation coefficient for each plot is given in the plot.

DEFINITIONS

Figure 4:
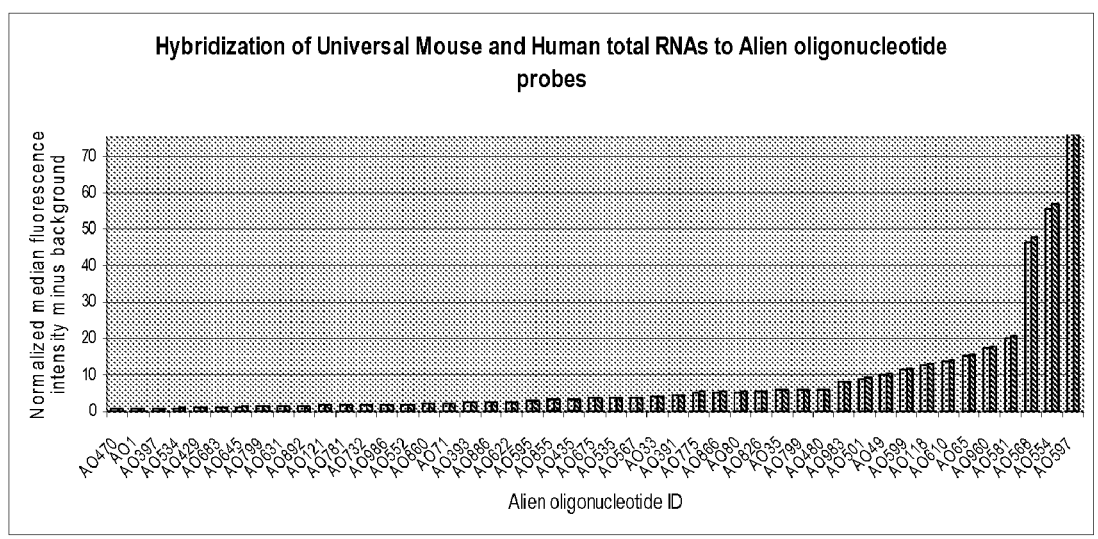
FIG. 4 ranks the alien oligonucleotides depicted in FIG. 2 based on normalized median fluorescence intensity minus background when hybridized with standard human and mouse mRNA samples.

Throughout the specification, several terms are employed, that are defined in the following paragraphs.

Alien gene—As used herein, the term "alien gene" refers to a nucleotide molecule comprised of at least two concatermerized alien sequences. The gene may contain multiple copies of a single alien sequence, or alternatively may contain a plurality of different alien sequences. An alien gene may be single or double stranded, and may contain or be associated with a promoter or other control sequence that will direct the production of a template of either strand of the gene. In particular, as will be clear from discussions herein, in some embodiments of the invention it will be desirable to produce an alien gene transcript that is an alien sequence, whereas in other embodiments it will be desirable to produce an alien gene transcript that is complementary to an alien sequence.

Alien sequence—A nucleotide sequence is considered "alien" to a particular source or collection of nucleic acids if it does not hybridize with nucleic acids in the source or collection. For example, if the source or collection is mRNA from normal kidney cells, an oligonucleotide will have a sequence that is "alien" to the mRNA if its complement is not present in the mRNA. Conversely, if the source or collection is cDNA from the same cells, then an oligonucleotide will have a sequence that is "alien" to the cDNA if its complement is not present in the cDNA. In certain preferred embodiments of the invention, the source or collection comprises expressed nucleic acids (e.g., mRNA or cDNA) of a target organism (e.g., mouse, dog, human, etc), tissue (e.g., breast, lung, colon, liver, brain, kidney, etc), or cell type (e.g., before or after exposure to a particular stimulus or treatment). Alternatively or additionally, the source or collection may preferably be a plurality of nucleic acids to be hybridized to an array.

Hybridizing sample—The terms "hybridizing sample" and "hybridizing mixture" are used herein interchangeably. They refer to the nucleic acid sample being or intended to be hybridized to a microarray. Those of ordinary skill in the art will appreciate that the hybridizing sample may contain DNA, RNA, or both, but most commonly contains cDNA. Those of ordinary skill in the art will further appreciate that the hybridizing sample typically contains nucleic acids whose hybridization with probes on an array is detectable. For example, in many embodiments, the hybridizing sample comprises or consists of detectably labeled nucleic acids.

Detectably labeled—The terms "labeled", "detectably labeled" and "labeled with a detectable agent" are used herein interchangeably. They are used to specify that a nucleic acid molecule or individual nucleic acid segments from a sample can be detected and/or visualized following binding (i.e., hybridization) to probes immobilized on an array. Nucleic acid samples to be used in the methods of the invention may be detectably labeled before the hybridization reaction or a detectable label may be selected that binds to the hybridization product. Preferably, the detectable agent or moiety is selected such that it generates a signal which can be measured and whose intensity is related to the amount of hybridized nucleic acids. Preferably, the detectable agent or moiety is also selected such that it generates a localized signal, thereby allowing spatial resolution of the signal from each spot on the array. Methods for labeling nucleic acid molecules are well known in the art (see below for a more detailed description of such methods). Labeled nucleic acids can be prepared by incorporation of or conjugation to a label, that is directly or indirectly detectable by spectroscopic, photochemical, biochemical, immunochemical, radiochemical, electrical, optical, or chemical means. Suitable detectable agents include, but are not limited to: various ligands, radionuclides, fluorescent dyes, chemiluminescent agents, microparticles, enzymes, colorimetric labels, magnetic labels, and haptens. Detectable moieties can also be biological molecules such as molecular beacons and aptamer beacons.

Fluorescent Label—The terms "fluorophore", "fluorescent moiety", "fluorescent label", "fluorescent dye" and "fluorescent labeling moiety" are used herein interchangeably. They refer to a molecule which, in solution and upon excitation with light of appropriate wavelength, emits light back. Numerous fluorescent dyes of a wide variety of structures and characteristics are suitable for use in the practice of this invention. Similarly, methods and materials are known for fluorescently labeling nucleic acids (see, for example, R. P. Haugland, "*Molecular Probes: Handbook of Fluorescent Probes and Research Chemicals 1992-1994*", $5^{th}$ Ed., 1994, Molecular Probes, Inc.). In choosing a fluorophore, it is generally preferred that the fluorescent molecule absorbs light and emits fluorescence with high efficiency (i.e., it has a high molar absorption coefficient and a high fluorescence quantum yield, respectively) and is photostable (i.e., it does not undergo significant degradation upon light excitation within the time necessary to perform the array-based hybridization). Suitable fluorescent labels for use in the practice of the methods of the invention include, for example, Cy-3™, Cy-5™, Texas red, FITC, Spectrum Red™, Spectrum Green™, Alexa-488, phycoerythrin, rhodamine, fluorescein, fluorescein isothiocyanine, carbocyanine, merocyanine, styryl dye, oxonol dye, BODIPY dye, and equivalents, analogues or derivatives of these molecules.

Microarray—The terms "microarray", "chip" and "biochip" are used herein interchangeably. They refer to an arrangement, on a substrate surface, of multiple nucleic acid molecules of known or unknown sequences. These nucleic acid molecules are immobilized to discrete "spots" (i.e., defined locations or assigned positions) on the substrate surface. A discrete spot may contain a single nucleic acid molecule or a mixture of different nucleic acid molecules. Spots on an array may be arranged on the substrate surface at different densities. In general, microarrays with probe pitch smaller than 500 μm (i.e., density larger than 400 probes per $cm^2$) are referred to as high density microarrays, otherwise, they are called low density microarrrays. Arrays come as two-dimensional probe matrices (or supports), which can be solid or porous, planar or non-planar, unitary or distributed. The term "micro-array" more specifically refers to an array that is miniaturized so as to require microscopic examination for visual evaluation. Arrays used in the methods of the invention are preferably microarrays. The present invention provides microarrays in which at least one spot contains an alien oligonucleotide. Other types of microarrays and sets of microarrays provided by the invention are described below.

Oligonucleotide—As used herein, the term "oligonucleotide", refers to usually short strings of DNA or RNA to be used as hybridizing probes or nucleic acid molecule array elements. These short stretches of sequence are often synthesized chemically. As will be appreciated by those skilled in the art, the length of the oligonucleotide (i.e., the number of nucleotides) can vary widely, often depending on its intended function or use. Generally, oligonucleotides of at least 6 to 8 bases are used, with oligonucleotides ranging from about 10 to 500 bases being preferred, with from about 20 to 200 bases being particularly preferred, and 40 to 100 bases being especially preferred. Longer oligonucleotide probes are usually preferred in array-based hybridization reactions, since higher stringency hybridization and wash conditions can be used, which decreases or eliminates non-specific hybridization.

Probe—For the purposes of the present invention, a "probe" is a nucleic acid, often an oligonucleotide that is, or is intended to be, attached to a solid support in an array. Preferably, the probes that comprise a microarray or biochip are of a defined length and similarity. This allows for similar hybridization characteristics. As is well known to those skilled in the art, for the hybridization characteristics to be similar across a wide range of oligonucleotides, it is typically required that the probes on the array be of the substantially same length, have a similar percentage of Guanine to Cytosine content and lack any extensive runs of poly A, poly G, poly C, or poly T tracts. The goal of controlling these parameters is to produce probes that have similar melting and hybridization temperatures. Additionally, these probes should, preferably, lack length complementary regions and not form hairpin structures.

Target—The term "target" refers to nucleic acids intended to be hybridized (or bound) to probes immobilized on microarrays by sequence complementarity. As is well-known in the art, target nucleic acids may be obtained from a wide variety of organisms, tissues or cells. Methods and techniques for the extraction, manipulation and preparation of nucleic acids for hybridization reactions are well-known in the art (see, for example, J. Sambrook et al., "*Molecular Cloning: A Laboratory Manual*", 1989, $2^{nd}$ Ed., Cold Spring Harbour Laboratory Press: New York, N.Y.; "*PCR Protocols: A Guide to Methods and Applications*", 1990, M. A. Innis (Ed.), Academic Press: New York, N.Y.; P. Tijssen "*Hybridization with Nucleic Acid Probes—Laboratory Techniques in Biochemistry and Molecular Biology (Parts I and II)*", 1993, Elsevier Science; "*PCR Strategies*", 1995, M. A. Innis (Ed.), Academic Press: New York, N.Y.; and "*Short Protocols in Molecular Biology*", 2002, F. M. Ausubel (Ed.), $5^{th}$ Ed., John Wiley & Sons).

Hybridization—The term "hybridization" has herein its art understood meaning and refers to the binding of two single stranded nucleic acids via complementary base pairing. A hybridization reaction is called specific when a nucleic acid molecule preferentially binds, duplexes, or hybridizes to a particular nucleic acid sequence under stringent conditions (e.g., in the presence of competitor nucleic acids with a lower degree of complementarity to the hybridizing strand).

High stringency conditions—For microarray-based hybridization, standard "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for at least 8 hours, followed by one or more washes in 0.2×SSC, 0.1% SDS at 65° C. "Moderate stringency conditions" are defined for solution phase hybridization as aqueous hybridization (i.e., free of formamide) in 6×SSC, 1% SDS at 65° C. for at least 8 hours, followed by one or more washes in 2×SSC, 0.1% SDS at room temperature.

DESCRIPTION OF CERTAIN PREFERRED EMBODIMENTS OF THE INVENTION

The present invention provides reagents and methods that are useful in normalizing and standardizing data from nucleic acid hybridization studies, and particularly from microarray hybridizations. The present invention teaches that it is useful to define nucleotide sequences that are "alien" to the sequence population under analysis.

In particular, the use of such alien oligonucleotide sequences in micro-array based hybridization is herein described to be able to serve several distinct control purposes. For example, (1) when spotted on microarrays, alien sequences can serve as negative controls during the course of hybridization experimentation to assess the stringency (i.e., specificity) of target-to-probe hybridization. (2) Alien oligonucleotides spotted on micro-arrays, in combination with their complementary sequences used as in-spike controls can enable the experimenter to gauge the robustness of both the overall target labeling and hybridization efficiency. (3) When alien probe sequences are present within each sub-array on the biochip, they allow regional (intra-slide) effects of hybridization to be ascertained. (4) Alien oligonucleotides can also be used as in-spot controls and act as references so that inter-slide differences can be measured relative to a consistent control. (5) Detectably labeled alien sequences can be used to normalize the signal intensities of the samples under analysis on a per spot basis. Also, (6) in situ alien sequences may also be used to quality control the DNA microarray printing process.

In a first aspect, the present invention provides methods of identifying nucleotide sequences that are alien to a selected population.

Generating or Selecting Alien Sequences

As mentioned above, a nucleotide sequence is considered "alien" to a particular source or collection of nucleic acids if it does not hybridize with nucleic acids in the source or collection. For example, if the source or collection is mRNA or cDNA, then an oligonucleotide has a sequence that is "alien" to the mRNA or cDNA if its complement is not present in the mRNA or cDNA. Preferred alien oligonucleotides of the invention have complementary sequences that are maximally dissimilar from (i.e., non-identical to) those present in the source or collection.

When comparing polynucleotide sequences, two sequences are said to be "identical" if the sequence of nucleotides in the two sequences is the same when aligned for maximum correspondence. Comparisons between two sequences are typically performed by comparing the sequences over a comparison window to identify and compare local regions of sequence similarity. A "comparison window" refers to a segment of at least about 20 contiguous positions, usually 30 to about 75, or 40 to about 50, in which a sequence may be compared to a reference sequence of the same number of contiguous positions after the two sequences are optimally aligned.

Any of a wide variety of selection methods, systems or strategies that lead to the generation of oligonucleotides alien to a source or collection of nucleic acids can be used in the practice of the present invention. Such methods may, for example, be based on the use of an algorithm.

The present invention provides such an algorithm, in which the underlying logic is that of "partially reversing" the mathematical logic of the standard Hidden Markov Model. Such standard models are used to generate model sequences of DNA, RNA, proteins as well as other biological molecules, based on the statistics of known real (i.e., naturally occurring) sequences. Model sequences are generated based on sets of sequence symbol occurrences. For example, given the measured nearest neighbor frequencies (i.e., how often one nucleotide follows another) one then draws and outputs "randomly" from that set proportional to those frequencies. A very wide range of sequences statistics can be employed, from the simplest, the occurrence frequencies of the individual symbols, through all possible nearest neighbor frequencies to arbitrary spaced sequences frequencies.

A first approach used by the Applicants with the goal of generating "alien" or maximally dissimilar sequences from known real sequences was to perform a complete "reversal" of the statistics (i.e., to invert the sets of occurrence probability from most likely to least likely). However, when this strategy was tested over a very large set of sequences statistics, it did not work.

What did work in generating model sequences which are maximally dissimilar from those employed to obtain the sequence statistics, was to use a Markov process, in which, at an adjustable frequency, one draws from the measured real statistics but inversely proportional to those frequencies (or probability distributions). The sequence generated by this process contains, scattered throughout its length, intermittent highly improbable sequence patterns or subsequences. The frequency with which one switches between draws from the measured real sequence occurrence frequencies proportional to those frequencies and inversely proportional to those frequencies and inversely, ranges from one in five to one in ten. The selection of this ratio is partly a function of which sets of sequence statistics are used.

In the generation of maximally dissimilar DNA or mRNA complement sequences for microarray controls, preferably in the length range of 50 to 70 nucleotides, codon occurrence and codon boundary di-nucleotide frequencies were used for a range of inverse proportional inverse probability draws on these two statistics. This process was then followed by two filters, including: (1) a full genome sequence similarity search of all known or predicted protein coding regions, and (2) the calculation of TMs for all possible mRNA annealings for those with any sequence similarities above 60% identity and/or with matching runs longer than 18 nucleotides. All generated sequences with predicted annealing temperature above 37° C. or runs of twenty identities were eliminated. The TMs (i.e., midpoint disassociation temperatures) were calculated using multiple public domain software which included nucleotide stacking energies. This resulted in approximately one predicted "alien" or non-mRNA annealing oligo for every 5,000 genome coding regions in the higher animal and plant eukaryotic genomes currently known. Sets of these alien sequences were then synthesized and placed on "long oligo" microarray chips and physically tested for their annealing to real mRNA and/or cDNA samples. With rare exceptions (of one in ten), no detectable annealing was observed under standard experimental conditions for 70 mer oligo array chips for 21,000 mouse genes. These alien sequences then define a set of negative controls.

A set of microarray "alien positive controls" was then generated from the above set of alien oligo negative control sequences using the following algorithm. First all possible set of three to five sequentially concatenated alien oligos as defined above were generated in silico. These were investigated for the incidental creation of a sequence crossing the boundary between the concatenated alien oligos that have a significant match or predicted annealing TM above 37° C. to any of the non-alien oligos on the micro-array targeted. Only those that showed no such matches or higher TMs were selected. These oligos were then physically synthesized as "positive alien gene" controls and tested for their ability to only anneal to their complementary alien oligos.

FIG. 1 shows about 100 sequences (of about 1000) that were generated using the inventive alien cDNA algorithm described above, by inverting sequences 35% of the time. FIG. 2 shows about 50 oligonucleotides identified as alien to mouse cDNA by the inventive algorithm and useful for hybridization applications.

In light of the inventive results described herein, those of ordinary skill in the art will appreciate that other algorithms may be employed or developed, for example, to include filter steps that, for example, verify the degree of "alien"ness of the selected sequence by comparing the generated oligonucleotide sequences to the organism's genome (if available) or cDNA by using any of a large number of sequence comparison programs.

A variety of methods for determining relationships between two or more sequences (e.g., identity, similarity and/or homology) are available, and well known in the art. The methods include manual alignment, computer assisted sequence alignment and combinations thereof. A number of algorithms (which are generally computer implemented) for performing sequence alignment are widely available, or can be produced by one of skill in the art. These methods include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

For example, a software for performing sequence identity (and sequence similarity) analysis using the BLAST algorithm is described in Altschul et al., J. Mol. Biol., 1990, 215: 403-410. This software is publicly available, e.g., through the National Center for Biotechnology Information on the World Wide Web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extensions of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP (BLAST Protein) program uses as defaults a wordlength (W) of 3, an expectation (E) of 10, and the BLOSUM62 scoring matrix (see, Henikoff & Henikoff, Proc. Natl. Acad. Sci. USA, 1989, 89:10915).

Additionally, the BLAST algorithm performs a statistical analysis of the similarity between two sequences (see, e.g., Karlin & Altschul, Proc. Natl. Acad. Sci. USA, 1993, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, or less than about 0.01, and or even less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (J. Mol. Evol. 1987, 35: 351-360). The method used is similar to the method described by Higgins & Sharp (CABIOS, 1989, 5: 151-153). The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their nucleotide coordinates for regions of sequence comparison.

An additional example of an algorithm that is suitable for multiple DNA sequence alignments is the CLUSTALW program (J. D. Thompson et al., Nucl. Acids. Res. 1994, 22: 4673-4680). CLUSTALW performs multiple pairwise comparisons between groups of sequences and assembles them into a multiple alignment based on homology. Gap open and Gap extension penalties can be, e.g., 10 and 0.05 respectively.

An algorithm for the selection of alien sequences may also include filter steps that check for TM, % GC content, low-complexity regions and self hybridization. A large number of software programs (including those described above) are available and can be used to carry out these steps.

Alien Oligonucleotide Preparation

In another aspect, the present invention provides isolated oligonucleotides or nucleic acids that are alien to a given source or collection of nucleic acids. As will be appreciated by one skilled in the art, alien oligonucleotides may be of different lengths, depending on their intended use (as negative control, normalization and/or quantification tool or as in-spike control). For example, alien oligonucleotides may contain a single alien sequence. Alternatively, an alien oligonucleotide may contain at least two alien sequences linked to one another. Inventive oligonucleotides provided herein also include those polynucleotides that contain anti-alien sequences. For example, as described herein, it will often be desirable to prepare anti-alien sequences for use in hybridization reactions. In some embodiments, such sequences are prepared by polymerization directed by an alien gene.

Alien and anti-alien oligonucleotides of the invention may be prepared by any of a variety of chemical techniques well-known in the art, including, for example, chemical synthesis and polymerization based on a template (see, for example, S. A. Narang et al., Meth. Enzymol. 1979, 68: 90-98; E. L. Brown et al., Meth. Enzymol. 1979, 68: 109-151; E. S. Belousov et al., Nucleic Acids Res. 1997, 25: 3440-3444; D. Guschin et al., Anal. Biochem. 1997, 250: 203-211; M. J. Blommers et al., Biochemistry, 1994, 33: 7886-7896; and K. Frenkel et al., Free Radic. Biol. Med. 1995, 19: 373-380; see also for example, U.S. Pat. No. 4,458,066).

For example, oligonucleotides may be prepared using an automated, solid-phase procedure based on the phosphoramidite approach. In such a method, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytrityl (or DMT) group at the 5'-position. After base base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on commercial oligo synthesizers such as the Perkin Elmer/Applied Biosystems Division DNA synthesizer. Such a synthesis is described in Example 2.

Oligonucleotides can also be custom made and ordered from a variety of commercial sources well-known in the art, including, for example, the Midland Certified Reagent Company (mcrc@oligos.com), The Great American Gene Company (available on the World Wide Web at genco.com), ExpressGen Inc. (available on the World Wide Web at expressgen.com), Operon Technologies Inc. (Alameda, Calif.) and many others.

Purification of oligonucleotides of the invention, where necessary, may be carried out by any of a variety of methods well-known in the art. Purification of oligonucleotides is typically performed by either by native acrylamide gel electrophoresis or by anion-exchange HPLC as described, for example, by Pearson and Regnier (J. Chrom. 1983, 255: 137-149). The sequence of the synthetic oligonucleotides can be verified using the chemical degradation method of Maxam and Gilbert (in Grossman and Moldave (Eds.), Academic Press, New York, Methods in Enzymology, 1980, 65: 499-560).

The present invention provides nucleic acid arrays in which at least one spot contains an alien oligonucleotide. More specifically, inventive nucleic acids arrays comprise a solid support, and a plurality of nucleic acid probes attached to the solid support at discrete locations, wherein at least one the probes is an alien probe in that it has a sequence that is alien to a hybridizing mixture to be hybridized to the array.

Microarrays generally have sample spot sizes of less than 200 μm diameter, and generally contain thousands of spots per slide. For gene-expression analysis, each microarray preferably contains at least about 1,000, 5,000, 10,000, 50,000, 100,000, or 500,000 spots. The probes are printed (or attached) to the surface of the substrate, and the number of probes per unit area of the print surface is called the print density. The print surface corresponds to that area of the substrate on which the individual probes are printed, plus the surface area between the individual probes. If there are two or more groupings of a substantial number of probes on the substrate surface separated by surface area in which few or no probes are printed, the print surface includes the surface area between probes of a group but not the surface area of the substrate between groupings. For gene expression analysis, the print density is preferably high so that a large number of probes can fit on the substrate. Preferably, the print density is at least about 200, 500, 1,000, 5,000, 10,000, 20,000, or 40,000 probes per $cm^2$.

There are two standard types of DNA microarray technology in terms of the nature of the arrayed DNA sequence. In the first format, probe cDNA sequences (typically 500 to 5,000 bases long) are immobilized to a solid surface and exposed to a plurality of targets either separately or in a mixture. In the second format, oligonucleotides (typically 20-80-mer oligos) or peptide nucleic acid (PNA) probes are synthesized either in situ (i.e., directly on-chip) or by conventional synthesis followed by on-chip attachment, and then exposed to labeled samples of nucleic acids. In the present invention, microarrays of the second type are preferably used.

In the practice of the methods of the invention, investigators may either buy commercially available arrays (for example, from Affymetrix Inc. (Santa Clara, Calif.), Illumina, Inc. (San Diego, Calif.), Spectral Genomics, Inc. (Houston, Tex.), and Vysis Corporation (Downers Grove, Ill.)), or generate their own starting microarrays (i.e., arrays to which at least one alien oligonucleotide is to be spotted). Methods of making and using arrays are well known in the art (see, for example, S. Kern and G. M. Hampton, Biotechniques, 1997, 23:120-124; M. Schummer et al., Biotechniques, 1997, 23:1087-1092; S. Solinas-Toldo et al., Genes, Chromosomes & Cancer, 1997, 20: 399-407; M. Johnston, Curr. Biol. 1998, 8: R171-R174; D. D. Bowtell, Nature Gen. 1999, Supp. 21:25-32; D. J. Lockhart and E. A. Winzeler, Nature, 2000, 405: 827-836; M. Cuzin, Transfus. Clin. Biol. 2001, 8:291-296; M. Gabig and G. Wegrzyn, Acta Biochim. Pol. 2001, 48: 615-622; and V. G. Cheung et al., Nature, 2001, 40: 953-958).

Arrays comprise a plurality of probes immobilized to discrete spots (i.e., defined locations or assigned positions) on a substrate surface. Substrate surfaces for use in the present invention can be made of any of a variety of rigid, semi-rigid or flexible materials that allow direct or indirect attachment (i.e., immobilization) of probes (including alien oligonucleotides) to the substrate surface. Suitable materials include, but are not limited to: cellulose (see, for example, U.S. Pat. No. 5,068,269), cellulose acetate (see, for example, U.S. Pat. No. 6,048,457), nitrocellulose, glass (see, for example, U.S. Pat. No. 5,843,767), quartz or other crystalline substrates such as gallium arsenide, silicones (see, for example, U.S. Pat. No. 6,096,817), various plastics and plastic copolymers (see, for example, U.S. Pat. Nos. 4,355,153; 4,652,613; and 6,024,872), various membranes and gels (see, for example, U.S. Pat. No. 5,795,557), and paramagnetic or supramagnetic microparticles (see, for example, U.S. Pat. No. 5,939,261). When fluorescence is to be detected, arrays comprising cyclo-olefin polymers may preferably be used (see, for example, U.S. Pat. No. 6,063,338).

The presence of reactive functional chemical groups (such as, for example, hydroxyl, carboxyl, amino groups and the like) on the material can be exploited to directly or indirectly attach probes including alien oligonucleotide sequences to the substrate surface. Methods of attachment (or immobilization) of oligonucleotides on substrate supports have been described and are well-known to those skilled in the art (see, for example, U. Maskos and E. M. Southern, Nucleic Acids Res. 1992, 20: 1679-1684; R. S. Matson et al., Anal. Biochem. 1995, 224; 110-116; R. J. Lipshutz et al., Nat. Genet. 1999, 21: 20-24; Y. H. Rogers et al., Anal. Biochem. 1999, 266: 23-30; M. A. Podyminogin et al., Nucleic Acids Res. 2001, 29: 5090-5098; Y. Belosludtsev et al., Anal. Biochem. 2001, 292: 250-256).

Methods of preparation of oligonucleotide-based arrays that can be used to attach probes to surface support of microarrays include: synthesis in situ using a combination of photolithography and oligonucleotide chemistry (see, for example, A. C. Pease et al., Proc. Natl. Acad. Sci. USA 1994, 91: 5022-5026; D. J. Lockhart et al., Nature Biotech. 1996, 14: 1675-1680; S. Singh-Gasson et al., Nat. Biotechn. 1999, 17: 974-978; M. C. Pirrung et al., Org. Lett. 2001, 3: 1105-1108; G. H. McGall et al., Methods Mol. Biol. 2001, 170; 71-101; A. D. Barone et al., Nucleosides Nucleotides Nucleic Acids, 2001, 20: 525-531; J. H. Butler et al., J. Am. Chem. Soc. 2001, 123: 8887-8894; E. F. Nuwaysir et al., Genome Res. 2002, 12: 1749-1755). The chemistry for light-directed oligonucleotide synthesis using photo labile protected 2'-deoxynucleoside phosphoramides has been developed by Affymetrix Inc. (Santa Clara, Calif.) and is well known in the art (see, for example, U.S. Pat. Nos. 5,424,186 and 6,582,908).

Alternatively or additionally, oligo probes may first be prepared or print-ready oligonucleotide (e.g., 60-70 mers) sets that are commercially available for human, mouse and other organism (see, for example, http://www.cgen.com, http://www.operon.com) may be obtained and then attached to the array surface. Similarly, alien oligonucleotides are first synthesized and then immobilized on the surface of a microarray.

In these cases, the preparation of microarrays is preferably carried out by high-speed printing robotics. The established robotic spotting technique (U.S. Pat. No. 5,807,522) uses a specially designed mechanical robot, which produces a probe spot on the microarray by dipping a pin head into a fluid containing an off-line synthesized nucleic acid molecule and then spotting it onto the slide at a pre-determined position. Washing and drying of the pins are required prior to the spotting of a different probe in the microarray. In current designs of such robotic systems, the spotting pin, and/or the stage carrying the microarray substrates move along the XYZ axes in coordination to deposit samples at controlled positions of the substrates.

In addition to the established quill-pin spotting technologies, there are a number of microarray fabrication techniques that are being developed. These include the inkjet technology and capillary spotting.

Example 2 describes the printing of alien oligonucleotides to the surface of oligo slides (CodeLink, Amersham Biosciences, Piscataway, N.J.), which also contain human and mouse positive control spots.

As mentioned above, microarrays provided by the present invention are arrays containing a plurality of oligo probes and in which at least one spot contains an alien oligonucleotide. In certain preferred embodiments, an alien oligonucleotide is printed at more than one spot on the array. For example, an inventive microarray may contain, in addition to a plurality of oligo probes, a representative collection of spots containing the same or different concentrations of the alien oligonucleotide. Alternatively, all the spots on an inventive microarray may contain the same or different concentrations of the alien oligonucleotide.

In other embodiments, an inventive microarray contains at least two different alien oligonucleotides. These alien oligonucleotides may be spotted randomly throughout the whole array or they may be present in specific areas of the substrate surface, for example, forming probe elements (i.e., sub-arrays) containing only one type of alien oligonucleotide.

In still other embodiments, an inventive microarray contains alien oligonucleotides of different sizes. For example, an inventive microarray may contain a first oligonucleotide comprising a single alien sequence and a second oligonucleotide comprising at least two different alien sequences. The presence of both types of alien oligonucleotides on the microarray may, for example, allow two different types of controls to be performed.

The present invention also provides sets of microarrays that all contain identical probe elements (i.e., defined sets of spots) except for one microarray (or part of one microarray), which contains no alien oligonucleotide and another microarray (or part of a microarray) that contains the same probe elements but with fixed amount(s) of alien oligonucleotide.

Labeling of Nucleic Acid Molecules

In certain embodiments, nucleic acid molecules of the hybridizing mixture are labeled with a detectable agent before hybridization. In other embodiments, complementary sequences of alien oligonucleotides (i.e., anti-alien oligonucleotides), which are added to the hybridization sample before hybridization, are also labeled. In both cases, the role of a detectable agent is to facilitate detection and to allow visualization of hybridized nucleic acids. Preferably, the detectable agent is selected such that it generates a signal which can be measured and whose intensity is related to the amount of labeled nucleic acids present in the sample being analyzed. The detectable agent is also preferably selected such that it generates a localized signal, thereby allowing spatial resolution of the signal from each spot on the array.

The association between the nucleic acid molecule and detectable agent can be covalent or non-covalent. Labeled nucleic acids can be prepared by incorporation of or conjugation to a detectable moiety. Labels can be attached directly to the nucleic acid or indirectly through a linker. Linkers or spacer arms of various lengths are known in the art and are commercially available, and can be selected to reduce steric hindrance, or to confer other useful or desired properties to the resulting labeled molecules (see, for example, E. S. Mansfield et al., Mol. Cell. Probes, 1995, 9: 145-156).

Many methods for labeling nucleic acid molecules are well-known in the art. For a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachment of fluorescent dyes or of enzymes; chemical modifications of nucleic acids making them detectable immunochemically or by other affinity reactions; and enzyme-mediated labeling methods, such as random priming, nick translation, PCR and tailing with terminal transferase. More recently developed nucleic acid labeling systems include, but are not limited to: ULS (Universal Linkage System; see, for example, R. J. Heetebrij et al., Cytogenet. Cell. Genet. 1999, 87: 47-52), photoreactive azido derivatives (see, for example, C. Neves et al., Bioconjugate Chem. 2000, 11: 51-55), and alkylating agents (see, for example, M. G. Sebestyen et al., Nat. Biotechnol. 1998, 16: 568-576).

Any of a wide variety of detectable agents can be used in the practice of the present invention. Suitable detectable agents include, but are not limited to: various ligands, radionuclides (such as, for example, $^{32}P$, $^{35}S$, $^{3}H$, $^{14}C$, $^{125}I$, $^{131}I$ and the like); fluorescent dyes (for specific exemplary fluorescent dyes, see below); chemiluminescent agents (such as, for example, acridinium esters, stabilized dioxetanes and the like); microparticles (such as, for example, quantum dots, nanocrystals, phosphors and the like); enzymes (such as, for example, those used in an ELISA, e.g., horseradish peroxidase, beta-galactosidase, luciferase, alkaline phosphatase); colorimetric labels (such as, for example, dyes, colloidal gold and the like); magnetic labels (such as, for example, Dynabeads™); and biotin, dioxigenin or other haptens and proteins for which antisera or monoclonal antibodies are available.

In certain preferred embodiments, nucleic acid molecules (or anti-alien oligonucleotides) are fluorescently labeled. Numerous known fluorescent labeling moieties of a wide variety of chemical structures and physical characteristics are suitable for use in the practice of this invention. Suitable fluorescent dyes include, but are not limited to: Cy-3™, Cy-5™, Texas red, FITC, Alexa-488, phycoerythrin, rhodamine, fluorescein, fluorescein isothiocyanine, carbocyanine, merocyanine, styryl dye, oxonol dye, BODIPY dye (i.e., boron dipyrromethene difluoride fluorophore), and equivalents, analogues, derivatives or combinations of these molecules. Similarly, methods and materials are known for linking or incorporating fluorescent dyes to biomolecules such as nucleic acids (see, for example, R. P. Haugland, "*Molecular Probes: Handbook of Fluorescent Probes and Research Chemicals 1992-1994*", $5^{th}$ Ed., 1994, Molecular Probes, Inc.). Fluorescent labeling dyes as well as labeling kits are commercially available from, for example, Amersham Biosciences, Inc. (Piscataway, N.J.), Molecular Probes, Inc. (Eugene, Oreg.), and New England Biolabs, Inc. (Berverly, Mass.).

Favorable properties of fluorescent labeling agents to be used in the practice of the invention include high molar absorption coefficient, high fluorescence quantum yield, and photostability. Preferred labeling fluorophores exhibit absorption and emission wavelengths in the visible (i.e., between 400 and 750 nm) rather than in the ultraviolet range of the spectrum (i.e., lower than 400 nm).

Hybridization products may also be detected using one of the many variations of the biotin-avidin technique system, which that are well known in the art. Biotin labeling kits are commercially available, for example, from Roche Applied Science (Indianapolis, Ind.) and Perkin Elmer (Boston, Mass.).

Detectable moieties can also be biological molecules such as molecular beacons and aptamer beacons. Molecular beacons are nucleic acid molecules carrying a fluorophore and a non-fluorescent quencher on their 5' and 3' ends. In the absence of a complementary nucleic acid strand, the molecular beacon adopts a stem-loop (or hairpin) conformation, in which the fluorophore and quencher are in close proximity to each other, causing the fluorescence of the fluorophore to be efficiently quenched by FRET (i.e., fluorescence resonance energy transfer). Binding of a complementary sequence to the molecular beacon results in the opening of the stem-loop structure, which increases the physical distance between the fluorophore and quencher thus reducing the FRET efficiency and allowing emission of a fluorescence signal. The use of molecular beacons as detectable moieties is well-known in the art (see, for example, D. L. Sokol et al., Proc. Natl. Acad. Sci. USA, 1998, 95: 11538-11543; and U.S. Pat. Nos. 6,277,581 and 6,235,504). Aptamer beacons are similar to molecular beacons except that they can adopt two or more conformations (see, for example, O. K. Kaboev et al., Nucleic Acids Res. 2000, 28: E94; R. Yamamoto et al., Genes Cells, 2000, 5: 389-396; N. Hamaguchi et al., Anal. Biochem. 2001, 294: 126-131; S. K. Poddar and C. T. Le, Mol. Cell. Probes, 2001, 15: 161-167).

Multiple independent or interacting labels can also be incorporated into the nucleic acids. For example, both a fluorophore and a moiety that in proximity thereto acts to quench fluorescence can be included to report specific hybridization through release of fluorescence quenching (see, Tyagi et al., Nature Biotechnol. 1996, 14: 303-308; Tyagi et al., Nature Biotechnol. 1998, 16: 49-53; Kostrikis et al., Science, 1998, 279: 1228-1229; Marras et al., Genet. Anal. 1999, 14: 151-156; U.S. Pat. Nos. 5,846,726, and 5,925,517)

A "tail" of normal or modified nucleotides may also be added to nucleic acids for detectability purposes. A second hybridization with nucleic acid complementary to the tail and containing a detectable label (such as, for example, a fluorophore, an enzyme or bases that have been radioactively labeled) allows visualization of the nucleic acid molecules bound to the array (see, for example, system commercially available from Enzo Biochem Inc., New York, N.Y.).

The selection of a particular nucleic acid labeling technique will depend on the situation and will be governed by several factors, such as the ease and cost of the labeling method, the quality of sample labeling desired, the effects of the detectable moiety on the hybridization reaction (e.g., on the rate and/or efficiency of the hybridization process), the nature of the detection system to be used, the nature and intensity of the signal generated by the detectable label, and the like.

Hybridization

According to the methods provided, an inventive nucleic acid array (i.e., a microarray in which at least one spot contains an alien oligonucleotide) is contacted with a hybridizing mixture comprising a plurality of nucleic acids under conditions wherein the nucleic acids in the mixture hybridize to the probes on the array.

The hybridization reaction and washing step(s), if any, may be carried out under any of a variety of experimental conditions. Numerous hybridization and wash protocols have been described and are well-known in the art (see, for example, J. Sambrook et al., "*Molecular Cloning: A Laboratory Manual*", 1989, $2^{nd}$ Ed., Cold Spring Harbour Laboratory Press: New York; P. Tijssen "*Hybridization with Nucleic Acid Probes—Laboratory Techniques in Biochemistry and Molecular Biology (Part II)*", Elsevier Science, 1993; and "*Nucleic Acid Hybridization*", M. L. M. Anderson (Ed.), 1999, Springer Verlag: New York, N.Y.).

The hybridization and/or wash conditions may be adjusted by varying different factors such as the hybridization reaction time, the time of the washing step(s), the temperature of the hybridization reaction and/or of the washing process, the components of the hybridization and/or wash buffers, the concentrations of these components as well as the pH and ionic strength of the hybridization and/or wash buffers.

In certain cases, the specificity of hybridization may further be enhanced by inhibiting or removing repetitive sequences. By excluding repetitive sequences from the hybridization reaction or by suppressing their hybridization capacity, one prevents the signal from hybridized nucleic acids to be dominated by the signal originating from these repetitive-type sequences (which are statistically more likely to undergo hybridization).

Removing repetitive sequences from a mixture or disabling their hybridization capacity can be accomplished using any of a variety of methods well-known to those skilled in the art. Preferably, the hybridization capacity of highly repeated sequences is competitively inhibited by including, in the hybridization mixture, unlabeled blocking nucleic acids.

Microarray-based hybridization reactions in which alien oligonucleotides may serve as controls include a large variety of processes. For example, they may be useful in gene expression methods, such as those developed and used in pharmacogenomic research (see, for example, M. Srivastava et al., Mol. Med. 1999, 5: 753-767; and P. E. Blower et al., Pharmacogen. J. 2002, 2: 259-271); in drug discovery (see, for example, C. Debouk and P. N. Goodfellow, Nat. Genet. 1999, 21: 48-50; and A. Butte, Nat. Rev. Drug Discov. 2002, 1: 951-960), or in medicine and clinical research, for example, in cancer research (see, for example, J. DeRisi et al., Nat. Genet. 1996, 14: 457-460; C. S. Cooper, Breast Cancer Res. 2001, 3: 158-175; S. B. Hunter and C. S. Moreno, Front Biosci. 2002, 7: c74-c82; R. Todd and D. T. Wong, J. Dent. Res. 2002, 81: 89-97).

In another aspect, the inventive provides methods of using alien oligonucleotides and their complements in microarray-based hybridization experiments for different control purposes.

Alien Sequences as Negative Controls

In certain embodiments of the invention, alien oligonucleotide sequences are used to serve as a negative control during the course of the microarray experimentation. Negative controls are valuable when assessing the stringency of target-to-probe hybridization. For example, the selectivity of hybridization is known to be paramount to the accurate reflection of differential gene expression.

When present on a microarray, inventive alien oligonucleotides (i.e., molecules comprising sequences selected for their inability to hybridize nucleic acids of the source or collection under analysis) can act as negative controls. If a detectable signal can be measured from spots containing alien sequences, then hybridization conditions are not stringent and lead to significant cross-hybridization reactions, which, in turn, adversely affect the measured differential gene expression.

Use of Alien Sequences to Quantify Hybridization Sample Components

The present invention also provides methods that allow quantification of hybridizing sample components. Such methods are based on the use of microarrays containing alien oligonucleotides and on the addition of their complements (i.e., anti-alien sequences) to the hybridizing mixture before hybridization.

More specifically, inventive methods comprise providing a hybridizing mixture comprising a plurality of nucleic acids; and hybridizing the hybridizing mixture to a nucleic acid array of the invention, wherein the step of providing a hybridizing mixture comprises providing a mixture containing at least one anti-alien hybridizing nucleic acid whose sequence comprises a sequence complementary to the alien probe present on the inventive nucleic acid array.

In certain preferred embodiments, a known amount of an anti-alien oligonucleotide is added to a sample containing at least one experimental hybridizing nucleic acid of unknown quantity, and the mixture thus obtained is processed and prepared for hybridization to a microarray containing the alien oligonucleotide. The processing and preparation include labeling of both the anti-alien sequence and test nucleic acids with the same detectable agent. The degree of anti-alien/alien hybridization may be relied upon to establish the amount of test sequences present in the hybridizing sample based on the relative extent of their hybridization to complementary oligo probes present on the microarray.

In preferred embodiments, the degree of hybridization between the anti-alien and alien oligonucleotides and/or between the hybridizing nucleic acid and oligonucleotide probe present on the array is determined by measuring the signal intensities from the detectable label attached to the hybridized targets.

More specifically, if, for example, the target nucleic acids have been fluorescently labeled, the amount of a particular sequence in the hybridizing mixture is determined by comparing the intensity of the fluorescence signal measured for the hybridized sequence to the intensity of the fluorescence signal measured for the anti-alien sequence hybridized to the alien oligonucleotide present on the microarray.

In other preferred embodiments, an unknown amount of the anti-alien oligonucleotide is added to a nucleic acid sample to be analyzed and the resulting mixture is processed as above, before hybridization to a microarray containing a known amount of the alien oligonucleotide. The quantification of hybridization sample components may then be carried out as described above.

In other preferred embodiments of the invention, different amounts of multiple alien/anti-alien pairs are used for comparative quantification of nucleic acids of the test sample. Using amounts of multiple alien/anti-alien pairs, that vary from rare, to low, to abundant and highly abundant provides reference signal intensities for widely different ranges of target amounts (or concentrations), and therefore can help improve the accuracy of the quantification of test sequences. Such a method may be particularly useful when the signal intensity vs. detectable label amount (which is equivalent to hybridized target amount) exhibits a deviation from linearity in one or more concentration ranges.

Use of Alien Sequences for Normalization

Also provided by the present invention are methods wherein alien oligonucleotides are used as controls for in situ normalization.

At present, differential gene expression relies on changes in the relative abundance of any given mRNA between a test and reference total RNA sample. Usually ratios are derived that identify if a test sample mRNA is up- or down-regulated with respect to a reference sample, however in many instances no appropriate reference sample exists. Such a problem is typically encountered when samples are collected over extended periods of time (i.e., clinical studies) and need to be compared to a common reference or in diseased patients where no applicable reference is available.

In certain preferred embodiments, a microarray has spots containing a mixture of known amounts of the alien oligonucleotide and of a probe able to detect target (or hybridizing) sequences. Such an arrangement allows in situ comparisons. This approach also provides a consistent standard (the fixed amount of alien oligonucleotide) that can be relied upon to allow inter-slide comparisons and inter-experiment comparisons even when experiments are carried out with rare samples, or over a long time spans.

In these particular instances, an alien sequence can be used as an in-spot control and act as the reference so that inter-slide expression differences can be measured relative to a consistent control.

For instance, if every spot in an array has a defined mixture of experimental probes to alien probes, the presence of the alien oligonucleotides allows the researcher to control for variations between and among spots (e.g., by hybridizing the array with a sample containing anti-alien sequences that are differently labeled from the target sequences.

Those of ordinary skill in the art will appreciate that it is not essential that every spot on the array contain alien oligonucleotide, though it will typically be desirable that the alien oligo be present in a representative collection of spots, for example, so that the researcher can have reasonable confidence in the general uniformity of the spots. It will also be appreciated that, although convenient, it is not essential that every spot containing the alien sequence contain the same ratio of alien and experimental probes; so long as the ratio for each spot is defined and known.

In these methods, normalization is performed according to standard techniques.

Figure 8:
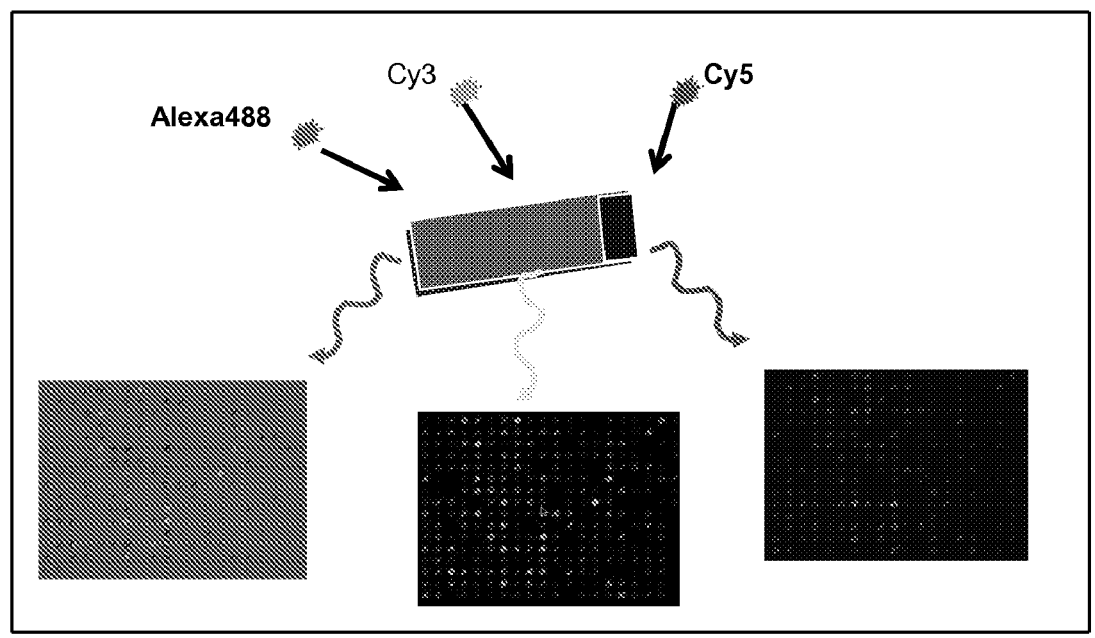
FIG. 8 illustrates the inventive concept of using an alien oligonucleotide and its complementary sequence as controls for in situ normalization. In such experiments, a microarray, to which an alien 70 mer probe has been co-printed with different gene specific probes, is contacted with a hybridization mixture containing the complementary sequence of the alien oligo labeled with Alexa-488, and two different nucleic acid test samples labeled with Cy3 and Cy5, respectively. A 3 color laser scanner is used to analyze the hybridized microarray.

As shown on the scheme presented in FIG. 8, an alien 70 mer probe can be co-printed with a gene specific probe on the microarray so that the two independent hybridizations can be measured within the same spot. A complementary alien oligonucleotide labeled with a fluorescent dye can be employed to serve as the reference, and can be simply mixed with the labeled target at known concentration prior to hybridization. The test RNA signal intensity is then compared to the alien control allowing like inter-slide comparisons to be made across a large data sets.

Controlling Hybridization Sample Processing and Hybridization with Alien Sequences Furthermore, when an alien oligonucleotide is present on an array, its complement may be added to the hybridizing sample, and processed (i.e., subjected to different treatments including labeling) together with the sample, and hybridized to an inventive microarray as a control for the processing/hybridization steps. If the alien oligonucleotide is present in spots at different locations on the chip, this strategy can also control intra-chip hybridization variation.

To give but one example, as described in the Examples, the present inventors have designed alien sequences that consist of four alien sequences that have been concatemerized behind a T7 promoter and to maintain polyadenylated tails. Upon transcription of the alien genes with T7 RNA polymerase, an alien transcript can be added to the total RNA input and act as an internal control during the course of cDNA generation, labeling, and hybridization. When alien probes, complementary to the alien gene, are included on the microarray, the experimenter can measure the extent of hybridization between the alien probe and the anti-alien nucleic acid in the labeled cDNA milieu to ascertain the overall labeling and hybridization efficiency. While this control does not definitively identify whether the labeling or hybridization may be at fault when there is a failure to detect fluorescent signal, it does allow the experimenter to identify if a problem has occurred and to compare the relative labeling efficiencies from experiment to experiment. One would anticipate that when the labeling and hybridization are successful, the relative signal intensity from the alien probe would be similar between slides. Similarly, regional effects of hybridization can be ascertained by including alien probe sequences within each sub-array on the chip. This comparative metric for inter-slide and intra-slide comparison is beneficial for quality control purposes.

Controlling for Array Manufacture using Alien Sequences

In another aspect, the invention provides methods that allow control of array manufacture. More specifically, when an alien oligonucleotide is present on an array, a standardized (i.e., a known amount, optionally labeled) complementary nucleic acid may be added to the hybridizing sample, and the extent of its hybridization to the alien sequence on the microarray can be used to assess the quantity of the array manufacture (e.g., the extent to which oligonucleotides were effectively coupled to the surface, etc).

Thus, according to the present invention, it is possible to analyze printed microarrays (e.g., prior to their experimental use, for example to ascertain if any spots are missing (and if so which ones), as well as to judge overall spot morphology and slide quality.

EXEMPLIFICATION

The following examples describe modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

EXAMPLE 1

Identification of Alien Sequences

The present invention provides systems for identifying "alien" sequences that are not found in the relevant population of nucleic acids being hybridized to an array. For instance, the invention provides systems for identifying sequences that are not present in the cDNA of a selected organism.

In particular, a software program was developed that allows the user to generate "alien" cDNAs for a particular organism. The program, the algorithm of which was described above, takes in a list of all known cDNA sequences for that particular organism (e.g., mouse). From this list, the program calculates the codon frequency of the sequences as well as dinucleotide or transition sequences at the codon boundary. These files can be stored and are specific for the organism from which the frequencies are generated. The program then generates cDNA (with start and stop codons) using the above frequencies. A small percentage of the time (as may be specified by the user), the generated frequencies are flipped such that the least frequent codon is now generated in the middle of the sequence. Such a sequence should be different from any cDNA occurring in the genome. The degree of "alien"ness of the sequence can be verified by comparing the generated sequences to the organism's genome (if available) or cDNA by using BLAST or another sequence comparison program. Oligos are then generated from the sequences by using another software program which checks for Tm and % GC content. The generated oligos are also compared to the organism genome or cDNA to verify that they do not hybridize to any part of the genome.

For example, FIG. 1 shows about 100 sequences (of about 1000) that were generated using the inventive alien cDNA software, by inverting sequences 35% of the time.

FIG. 2 shows about 50 sequences that were identified as alien to mouse cDNA and desirable for use in hybridization applications. The sequences were passed through oligo selection software to check Tm, % GC content, low-complexity regions and self hybridization. The software also checks by using two programs, Fuzznuc (EBI tool) and BLAST, whether the sequences have any similarity to cDNA from the organism in question. The oligos are then filtered by comparing them using BLAST against the organism's genome if available.

EXAMPLE 2

Attaching Alien Sequences to Chips

Synthesis of alien oligonucleotides. Each of the 47 70 mer alien oligonucleotide probes depicted in FIG. 2 was synthesized using an Expedite DNA synthesizer (Applied Biosystems, Framingham, Mass.) following standard protocols of phosphoramidite chemistry at a 200 nmol scale (S. L. Beaucage and R. P Iyer, Tetrahedron, 1992, 48: 2223-2311; S. L. Beaucage and R. P. Iyer, Tetrahedron, 1993, 49: 6123-6194). All alien oligonucleotides were modified at the 5' terminus with a TFA-amino-C-6-phosphoramidite (Prime Organics, Lowell, Mass.) to enable subsequent covalent attachment of the oligonucleotide to a CodeLink (Amersham Biosciences) slide surface. After synthesis, oligonucleotides were cleaved and deprotected from the CPG support with concentrated ammonium hydroxide at 80° C. for 16 hours and lyophilized. The oligonucleotides were re-dissolved in 300 μL of water and then desalted on Performa SR DNA synthesis cleanup plates (EdgeBiosystems, Gaithersburg, Md.). All oligonucleotides were quality assessed by capillary electrophoresis (CombiSep, Ames, Iowa) and quantified by UV spectroscopic measurement.

Preparation of oligo slide. Alien oligonucleotides were then printed and linked to the surface of oligos slides (CodeLink, Amersham Biosciences, Piscataway, N.J.), which also contained human and mouse positive control spots. All the plates were prepared following the same protocol.

Alien oligonucleotides were arrayed in Greiner 384-well flat-bottom plates (600 pmol of alien oligonucleotide per well). After resuspension in water to 20 μM, the oligonucleotides (5 μL) were re-arrayed into 384-well, Genetix polystyrene V-bottom plates, which were then allowed to dry in a chemical hood. Before printing, 5 μL of 1× Printing Buffer (150 mM sodium phosphate, 0.0005% Sarcosyl) were added to each well. The plates were incubated at 37° C. for 30 minutes to aid resuspension of DNA, vigorously shaken on a flat-bed shaker for 1 minute, and centrifuged at 2000 rpm for 3 minutes. These plates were then placed into an OmniGrid® 100 microarrayer (GeneMachines, San Carlos, Calif.) for the preparation of oligos slides.

After completion of each print run, the slides were removed from the microarrayer and placed overnight in a sealed humidification chamber containing a saturated brine solution and lined with moist paper towels. The slides were then transferred to a slide rack (25 slides per rack), which was placed into a container filled with Pre-warmed Blocking Solution (50 mM 2-aminoethanol; 0.1 M Tris pH 9, 0.1% N-Lauroyl sarcosine) to completely cover the slides, and then shaken for 15 minutes. The slides were rinsed twice with de-ionised water by transferring the slide rack to water filled containers. The slide rack was then transferred to another container filled with pre-warmed Washing Solution (4×SSC, 0.1% N-Lauroyl sarcosine) to completely cover the slides, and then shaken for 30 minutes. After the slides were rinsed twice with de-ionized water, they were dried by centrifugation at 800 rpm for 5 minutes, and stored in a dessicator.

Terminal Deoxynucleotidyl Transferase Quality Control. A first set of slides were treated with Terminal Deoxynucleotidyl Transferase in the presence of dCTP-Cy3, so that all oligonucleotides attached to the slide could be visualized and their attachment assessed. The labeling was performed by adding 10 μL of 5× reaction buffer (containing 500 mM sodium cacodylate, pH 7.2, 1 mM 2-mercaptoethanol, and 10 mM $CoCl_2$), 0.5 μL of Cy3-dCTP (Amersham), 2 μL of Terminal Deoxynucleotidyl Transferase (Amersham, 12 units/mL) and water to a final volume of 124 μL. The reaction solution was briefly vortexed and spun. The slides were boiled for 10 minutes in $ddH_2O$ and dried with a gentle air stream. The Terminal Transferase hybridization procedure, which was performed using a GeneTac Hybridization station (BST Scientific, Singapore), included an incubation cycle carried out at 37° C. for 2 hours followed by three washing steps.

After the slides were rinsed with 0.06×SSC, and then dried by centrifugation, they were scanned within the next 24 hours using an Axon GenePix 4000B scanner (Axon Instruments, Union City, Calif.). The resulting images were analyzed using the GenePix 3.0 software package.

As shown in FIG. 3A, the labeled alien oligonucleotides attached to slides having undergone such a Terminal Deoxynucleotididyl Transferase process were readily detectable, as were the human and mouse positive controls.

A second set of slides was not treated with terminal deoxynucleotidyl transferase, and instead was hybridized with labeled mRNA from human (Stratagene's Universal RNA Human) and mouse (Stratagene's Universal RNA Mouse).

Labeling of Universal Mouse/Human RNA. Before hybridization, samples of both types of mRNA were labeled using the standard indirect labeling method developed by J. B. Randolph and A. S. Waggoner (Nucleic Acids Res. 1997, 25: 2923-2929). Human mRNA was labeled with Cy5™ and mouse mRNA was labeled with Cy3™. Briefly, aminoallyl dUTP was incorporated during the reverse transcription of the total RNAs. This modified cDNA in turn was labeled via a coupling between an N-hydroxysuccinimide activated ester of a fluorescent dye (Monoreactive Cy3 and Cy5 from Amersham) and the aminoallyl moiety of the dUTP, following a modified version of the Atlas Powerscript Fluorescent Labeling Kit (BD Biosciences Clontech, Palo Alto, Calif.) protocol.

Hybridization to alien oligonucleotide microarrays. Hybridizations were performed on a Genomic Solutions GeneTac Hybridization Station (BST Scientific). A competitive DNA mix (containing salmon sperm DNA, Poly-A DNA and optionally Cot-1 DNA when the nucleic acid population under analysis was human) was added to hybridizing mixtures before hybridization. After hybridization, the slides were rinsed with 0.06×SSC, dried by centrifugation and scanned within the next 24 hours as described above.

As shown in FIG. 3B, although the alien oligonucleotides were present on the chip, they did not cross-hybridize to any known transcript in either the human or mouse universal total RNA set, while the human and mouse control probes did.

The results presented in FIG. 3 were quantified in different ways in order to evaluate the alien sequences employed. Specifically, as shown in FIG. 4, the 47 alien oligonucleotide probes were ranked according to the normalized median fluorescent signal intensity derived from the hybridization of the Universal Human and Mouse total RNA sets. While most probes gave signals slightly above background, three alien sequences (AO568, AO554, and AO597) exhibited significantly greater levels of hybridization (2-80 fold higher).

Figure 5:
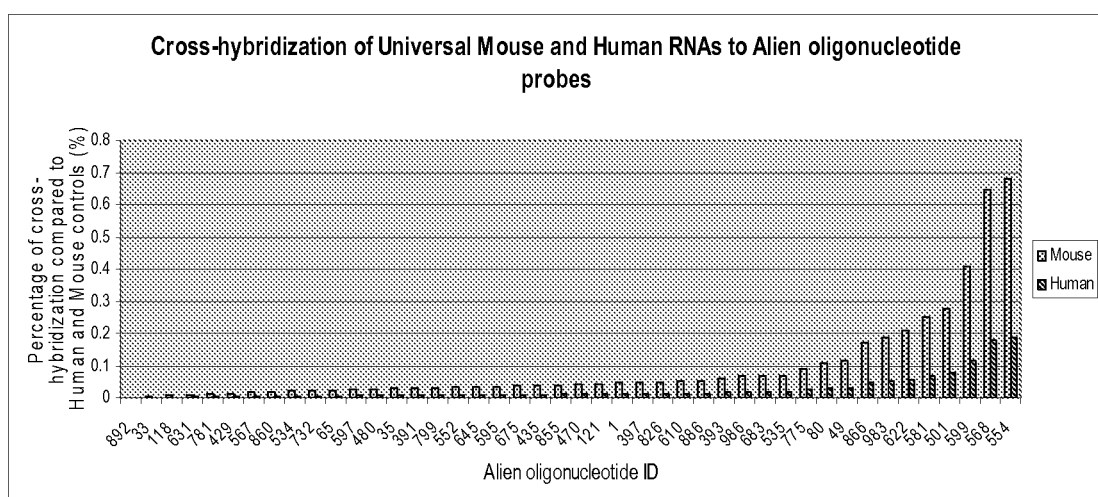
FIG. 5 ranks the alien oligonucleotides depicted in FIG. 2 based on their percentage of hybridization with standard human and mouse mRNA samples, as compared with the positive control oligonucleotides designed to hybridize with those samples.

Also, as shown in FIG. 5, the alien oligonucleotide probes generally showed higher levels of hybridization with the mouse mRNA sample than with the human mRNA sample, and no probe other than AO597 hybridized at a level that was as much as 1% of the positive control.

EXAMPLE 3

Using Alien Gene Transcripts as In-Spike Controls

As described herein, one advantage of using alien sequences in microarray experiments is that their complements may serve as an in-spike control, enabling the experimenter to gauge the robustness of the target labeling and hybridization. Specifically, if an alien oligonucleotide is present on a chip or slide, then a known amount of its complement may be added to the population of nucleic acids (e.g., mRNA or cDNA) to be hybridized to the slide. The population, now spiked with a known amount of anti-alien nucleic acid, is then labeled and hybridized to the chip or slide. Global problems in labeling or hybridization are revealed through the extent of alien/anti-alien hybridization on the chip or slide.

In order to create an in-spike control that would mimic an experimental cDNA sample to the greatest extent possible, three alien genes have been designed to consist of four different 70 mer alien sequences linked to one another in series and to a T7 promoter. The three alien genes also contained a polyadenylated tail to facilitate oligo(dT) priming. Alien gene A (321 bp), Alien gene B (322 bp) and Alien gene C (322 bp) are presented in FIG. 6 on Panels A, B and C, respectively.

The alien gene shown in FIG. 6B was constructed, and was used as a template for runoff transcription such that a single transcript containing four alien sequences followed by a polyA tail was generated.

More specifically, 10 ng of alien B was PCR amplified with a forward primer (5'-TTCTAATACGACTCACTATAGGGCATCTATCTATGTCAGTTACCGGC [SEQ ID NO: 151]) and a reverse primer (5'-TTTTTTTTTTTTTTTTTTTTTTTCTAATAACTGAGGTGATTTCCGAC [SEQ ID NO: 152]) using the SuperMix High fidelity polymerase (Invitrogen, Carlsbad, Calif.) and the Manufacturer's suggested protocol (which included the following cycle program: 94° C. for 30 sec, 55° C. for 55 sec, and 72° C. for 1 min) was followed. The reaction was performed for 30 cycles followed by a 3 min. final elongation incubation. The PCR product was analyzed on a 1.5% agarose gel and quantified according to quantitative low range DNA markers (Invitrogen).

The PCR product was then used as a template for in vitro transcription. In a reaction volume of 50 µL, 500 nM of PCR product was combined with 200 mM HEPES, pH 7.5, 7 mM NTPs, 20 mM $MgCl_2$, 40 mM dithiothreitol, 2 mM spermidine, 100 µg/mL bovine serum albumin (Roche, Nutley, N.J.), 8 units RNasin inhibitor (Promega, Madison Wis.), 0.5 units inorganic pyrophosphatase (Sigma, St. Louis, Mo.), and 500 units of T7 RNA polymerase (Epicentre, Madison, Wis.). The reaction was incubated for 16 h at 37° C. Following transcription, the reaction was phenol:chloroform extracted and LiCl precipitated. The pellet was rinsed with 70% aqueous ethanol, dissolved in 25 µL of buffer and quantified using UV spectroscopic methods.

The alien gene B run-off transcript was then reverse transcribed in the presence of amino-allyl dUTP (to allow for the incorporation of a label), using either a polyT primer or a collection of random hexamer primers. The resulting oligodT-primed cDNA was labeled with N-hydroxysuccinamide-Cy3; the resulting random-primed cDNA was labeled with N-hydroxysuccinamide-Cy5.

Microarrays were prepared by linking 8 different alien 70 mers, four of which were present in the alien gene and four of which were not, to a slide as described above in Example 2. As also described in Example 2, linkage of the 8 different oligonucleotides to the slide was assessed via enzymatic labeling with terminal transferase. As shown in FIG. 6D, detectable oligonucleotide was observed at each location.

A comparable chip was then hybridized with a mixture of the labeled oligodT-primed cDNA and the labeled random-primed cDNA. FIG. 6E shows that the cDNA mixture hybridized with the expected alien oligonucleotides, and not with the unrelated oligonucleotides. Furthermore, upon analysis, normalized median signal intensities from both the random and oligodT-primed cDNAs were similar for all four alien oligonucleotides present in the gene, indicating that, regardless of priming strategy, all four alien sequences were well represented with no positional bias within the alien gene.

EXAMPLE 4

Alien Sequences as Internal Controls

In order to demonstrate the use of alien sequences as internal controls for microarray spotting and hybridization, alien oligonucleotides were first shown to be able to effectively hybridize with their targets even when included in spots containing other oligonucleotides. Specifically, microarrays were constructed in which a single alien oligonucleotide, AO892 (5'GGTACGAATCTCCCATTGCATGGACAAATATAGTCCACGCATTGGACGCACCCACCGATGGCTCTCCAAT [SEQ ID NO: 153]), was spotted by itself in concentrations ranging from 2 to 20 µM, and was also spotted with a mixture of other 70 mer probes, whose concentrations also increased.

Figure 7:
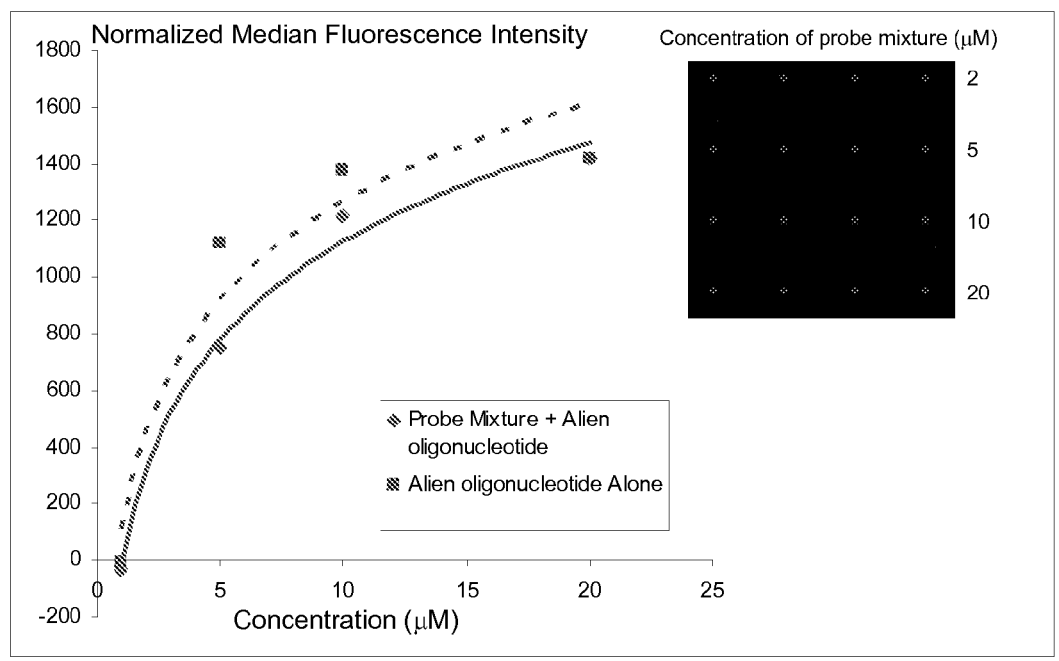
FIG. 7 illustrates the inventive concept of using alien sequences as internal controls for microarray spotting and hybridization. Microarrays were constructed in which a single alien oligonucleotide, AO892, was spotted by itself or with a mixture of other 70 mer oligonucleotide probes. AO892 alone or the probe mixture containing AO892 was spotted in concentrations ranging from 2 to 20 µM. The figure insert presents a small area of such a microarray. The graph shows the variations of the normalized signal intensity as a function of concentration of probe mixture, for AO892-alone spots and mixture spots.

An 70 mer oligonucleotide whose sequence was complementary to that of AO892 was prepared, modified at the 5'-terminus with a C-6 amino linker, and labeled with N-hydroxysuccinimide Alexa-488. This labeled complement was hybridized to the array under standard hybridization conditions, and differences between its hybridization to the pure AO892 spots and the mixture spots were assessed. As can be seen in the insert of FIG. 7, which shows one subarray, little change in signal intensity was observed as the concentration of the probe mixture increased. As shown in the graph presented in FIG. 7, there was no significant difference in normalized signal density between the AO892-alone spots and the mixture spots. These data demonstrate that hybridization to an alien oligonucleotide can be detected even in spots containing other sequences, such that alien sequences should be useful in the normalization of gene chip data on a per-spot basis.

EXAMPLE 5

Using Alien Oligos as In-site Controls and for Normalization

Methods:

Microarray fabrication, hybridization and scanning: The process of microarray fabrication, alien oligo synthesis, hybridization and scanning was carried out by the Massachusetts General Hospital, DNA Core Group. The protocols used for each of the following steps are described in detail at their website (dnacore.mgh.harvard.edu/microarray/protocols.shtml).

Alien oligo synthesis: The alien oligonucleotide probes were synthesized using an Expedite DNA synthesizer following standard protocols of phosphoramidite chemistry. All oligonucleotides were modified at the 5' terminus with a trifluoroacetamidohexyl-amino-C6-phosphoramidite which functionalizes the terminus and enables subsequent covalent attachment of the oligonucleotide to a CodeLink slide surface.

Preparation of the oligo slide: Briefly, alien oligos were arrayed in 384-well plates and mixed with printing buffer. These plates were then placed onto an Omnigrid 100 microarrayer for the preparation of oligo slides. After each print run, the slides were placed in a sealed humidification chamber. The slides were immersed in blocking solution, washed in 4×SSC and 0.1% N-lauroyl sacrosine and then stored in a dessicator. The alien oligos were printed along with a mouse oligonucleotide probe set which has 19,549 probes on the array providing complete coverage of the 2002 Mouse genome. Alien oligo 892 ("AO892") was printed in known concentrations in all spots of the microarray that contained mouse probes. Oligos that make up the alien gene transcripts were printed in separate spots on the slide. To act as print quality control and to check the attachment of all nucleotides to the slide, a few slides were treated with terminal deoxynucleotidyl transferase in the presence of dCTP-Cy3.

Labeling of RNA: Before hybridization, mRNA samples were labeled using the standard indirect labeling method developed by Randolph and Waggoner, *Stability, specificity and fluorescence brightness of multiply-labeled fluorescent DNA probes*, Nucleic Acids Research, 15;25(14):2923-9, 1997. Briefly, aminoallyl dUTP was incorporated during the reverse transcription of total RNA. The modified cDNA was labeled via a coupling between an N-hydroxysuccinimide-activated ester of a fluorescent dye (Cy3 or Cy5) and the aminoallyl moiety of the dUTP. The anti-alien to oligo AO892 and the three alien gene transcripts were mixed in known concentrations with the extracted mouse RNA. The anti-alien to oligo AO892 was labeled with Alexa488 while the alien gene transcripts were labeled with both Cy5 and Cy3.

Hybridization reactions: Hybridizations were performed on a Genomic Solutions GeneTac Hybridization Station. Cy3 and Cy5-labeled RNA were mixed with a competitive DNA mix containing salmon-sperm DNA, Poly-A DNA and Cot-1 DNA before hybridization Scanning: After hybridization and washing, the microarrays were scanned using the ProScanArray HT microarray scanner and the resulting images analyzed using ScanArray® Express v3.0 software.

Data Normalization and Filtering: Data from image analysis was stored for further processing in BASE (BioArray Software Environment). All spots flagged as unusable by the ScanArray software were excluded from further analysis. All array images were also analyzed manually to check for hybridization artifacts and to identify bad spots that had not been identified by the ScanArray program. The identified spots were also excluded from further analysis. Using BASE, all reference spots that had hybridization intensity readings less than 300 and all test sample spots that had hybridization intensity readings less than 50 were also removed from the dataset for analysis.

Typically, the first transformation applied to expression data, referred to as normalization, adjusted the individual hybridization intensities to balance them appropriately so that meaningful biological comparisons could be made. The filtered data was normalized in two ways depending on the presence or absence of information from alien/anti-alien hybridization.

Data normalization and replicate filtering in the absence of alien control data: Microarray data was normalized initially by scaling all individual intensities such that the total intensity was the same for both comparative samples (control and treatment) within a single array and across replicate arrays. This was based on the assumption that the starting amounts of RNA in each sample were equal. Using this approach, a normalization factor was calculated by summing the measured intensities in both channels:

$$N_{total} = \frac{\sum_{i=1}^{Narray} R_i}{\sum_{i=1}^{Narray} G_i},$$

where $G_i$ and $R_i$ are the measured green and red fluorescence intensities for the $i^{th}$ array element and Narray is the total number of elements represented in the microarray. One or both intensities were appropriately scaled to adjust for the normalization factor.

In addition to total intensity normalization, locally weighted linear regression (lowess) analysis was used to remove systematic, intensity-dependent effects in the data. The starting point for the lowess analysis, the 'R-I' (for ratio-intensity) plot, can reveal intensity-specific artifacts in the $\log_2$ (ratio) measurements. The RI or MA plot shows the measured $\log_2 (R_i/G_i)$ for each element on the array as a function of the $\log_{10} (R_i*G_i)$ product intensities. Lowess detects systematic deviations in the R-I plot and corrects them by carrying out a local weighted linear regression as a function of the $\log_{10}$ (intensity) and subtracting the calculated best-fit average $\log_2$ (ratio) from the experimentally observed ratio for each data point. The data was normalized globally.

The replicates per treatment and per time point when available were then combined to reduce the complexity of the data set. Genes with only one data point across all replicates after initial selection were excluded. Genes with more than one replicate data point were then analyzed for outliers and discarded if necessary. The data was combined using the geometric mean of the replicate ratios.

Data normalization and replicate filtering in the presence of alien controls: Two different methodologies were used to normalize data using alien hybridization intensities. Due to experimental design, the amount of anti-alien to alien hybridization in every spot on the array should be equal. This implies that the recorded alien hybridization (Alexa488) intensities should also be equal. One normalization procedure is to calculate the average alien hybridization intensity across all spots on the array and then normalize the alien hybridization intensity at a spot to that average intensity. The normalization factor for each spot can then be used to scale the treatment and control intensities for that spot. This normalization algorithm can be applied globally or locally. Local normalization can be applied to each group of array elements deposited by a single spotting pen.

Another method of normalization is to scale all alien hybridization intensities to an arbitrary constant intensity value. In the analyses conducted here, the second method was used. All alien hybridization intensities were scaled to a uniform intensity value of 1000. The normalization factor used to scale each individual spot was then used to adjust the other channel intensities at that spot. Replicates were then combined and genes with only one data point across all replicates after initial selection were excluded. Genes with more than one data point were analyzed for outliers using intensities from all three channel. The data from replicates were combined by calculating the geometric means of the individual intensities.

Identifying differentially expressed genes: The $\log_2$ ratio of gene expression for each spot for each gene was calculated either using direct or indirect comparison. Assuming there are two samples A and B, while using direct comparisons, the ratio T of gene i in sample A to sample B is $T_i=A_i/B_i$, where $A_i$ and $B_i$ are the normalized intensity values.

Further assuming that U is the universal reference sample used in two separate microarray experiments 1 and 2 to compare sample A to sample B indirectly, if $T_{1i}$ is the ratio of intensities of gene i in sample A to gene i in the universal reference, and $T_{2i}$ is the ratio of intensities of gene i in sample B to gene i in the universal reference, then the ratio $T_i$ of gene i in sample A to gene i in sample B is $T_i=T_{1i}/T_{2i}$.

When using the aliens as the reference channel for indirect comparison, the intensity of gene i in sample A and the intensity of gene i in sample B can be compared directly. This is possible as all spots in all arrays have been scaled such that the alien hybridization intensities are all equal to 1000. Therefore $T_i=A_{1i}/B_{2i}$, where $A_{1i}$ and $B_{2i}$ are intensity normalized and scaled values.

The standard $\log_2$ ratios were then calculated for each gene in each of the above cases. The mean and standard deviation of the distribution of $\log_2$(ratio) values was then calculated. The Z-score value for each gene was then used to determine if the gene was differentially expressed. Genes with $\log_2$ ratios over 2 standard deviations from the mean were identified as differentially expressed and chosen for further analysis. This allowed us to identify genes that were expressed sufficiently above the noise without having to resort to an arbitrary minimum ratio value.

Results and Conclusions:

The alien oligos can be used as internal controls for microarray spotting and hybridization, by spotting them in a mixture with the probes used to hybridize to the sample. This arrangement allows for in situ comparisons of every spot on a microarray. The aliens thus spotted can also act as references for inter-slide expression measurement and for inter-experiment expression measurement even when the experiment has been carried out over a long time span. Spotting a known amount of oligo in every spot and hybridizing to it a known amount of anti-alien along with the experimental sample, allows one to normalize for variations between spots. This would also serve to control for errors in the hybridization and labeling steps and for controlling intra-chip hybridization variation.

To demonstrate this, alien genes were first shown to hybridize to their targets even when other probes were present in the same spot. A single alien oligo, AO892, was used for this experiment. A sequence complementary to the oligo was synthesized and labeled with Alexa488. This sample was then hybridized to a slide which had pure alien oligo spots as well as spots with mixtures of the alien and normal probes. There was no significant change in normalized signal intensity between the two types of spots (data not shown).

To determine whether alien AO892 could be used as an in-spot reference, it was tested against another sample that could be used for an indirect reference, Stratagene's Universal Mouse® Reference RNA mix. A twelve-slide experiment was designed and carried out using mouse liver and macrophage RNA samples. All slides had spots with mixtures of the alien oligo and probes for mouse RNA. Alien oligo AO892 was printed in known concentrations in spots of the microarray that contained mouse gene-specific probes. It was printed at 10% final concentration of the mouse gene-specific probes in that spot. In four slides, Universal Mouse Reference RNA was used as the reference sample and liver RNA was used as test. Another four slides used mouse macrophage RNA as test samples and Universal Mouse as reference. A transcript complementary to AO892 and labeled with Alexa488 was added to all pre-hybridization mixes of labeled cDNA. These set of slides permitted comparison of differential expression between mouse liver and mouse macrophage samples by using both the Universal Mouse Reference RNA as well as the aliens as references. The last four slides directly compared liver RNA samples to macrophage RNA samples. A dye-swap was incorporated in each set of experiments.

The RNA was labeled and then hybridized on a chip containing the probe mixtures. The intensity readings were collected and quantified. Genes with low intensities not significantly above background were excluded from analysis. This reduced the number of spots from 19,552 to 18,268 for aliens and to 8,667 for the Universal RNA. The $\log_{10}$ of the intensities was then calculated and their frequency plotted (see FIG. 9). The readings for the aliens varied over two orders of magnitude but were within the linear range of the scanner. Also, there were few spots with very low intensities. The intensities of the Universal Mouse Reference RNA channel were bimodal and varied over a wide range. There were also many spots with very low intensities.

When using Universal Mouse RNA as reference, the microarray data was normalized by scaling all individual intensities such that the total intensity of the all channels was the same across replicate arrays for that experiment. Data from the replicate arrays were then combined to identify outliers and reduce statistical variation. When using the alien channel as reference, a spot to spot comparison across the two experiments was done and all intensities adjusted such that the alien intensity was set to 1000. For the final analysis, spots were chosen such that data was available for both direct and indirect comparisons. 6,866 spots were selected for comparison through the alien channel and 5,322 through the Universal RNA channel. The data was compared using $\log_2$ ratios of test RNA intensity to reference intensity and plotted (see FIG. 10). As can be seen from FIG. 10, there is a definite decrease in correlation when comparing the direct ratios to indirect ratios through the Universal RNA reference data than through the alien data. Thus, this example demonstrated that the alien data can be used as a reference channel to compare data from multiple chips and multiple experiments.

EXAMPLE 6

Using Alien Oligos as controls for TNF-α in Fracture Healing Mice

In the most widely used experimental design for microarrays, all the direct comparisons are made to a single reference sample. By following this method, the path connecting any two samples is always two steps. Thus, all comparisons are made with equal efficiency. In experiments that analyze RNA samples from two different conditions or two different treatments and when these samples derive from a series of time points, the most commonly used reference is the wild-type or untreated sample. This is inefficient because fully half of the measurements are made on the reference sample, which is presumably of little or no interest. Alien sequences could be used as a common reference in this experiment design as well. In this example, we have designed an experiment to compare fracture healing in wild-type and TNF-α receptor-deficient mice that would also allow us to test the use of the alien sequences as a common reference.

A total of 56 DNA arrays were divided into five sections (Table 1). RNA extracted from the tibia of wild type mice before fracture was used as the universal reference. All microarrays had the alien oligo AO892 mixed in with the gene-specific probes. The complementary sequence to AO892 was labeled with Alexa 488 and mixed into all hybridizing samples. The alien oligos that can bind the three alien transcripts to be used as in-spike controls were deposited in separate spots on the array. The alien transcripts were mixed with the sample and reference RNA before labeling in all experiments other than those in Experiment E of Table 1.

microarray datasets in Experiments A and B enabled a differential expression comparison of fracture healing in the transgenic mice as compared to the wild type mice at each time point, using either the common reference channel or the alien channel as control. The two references, wild type mice at time zero and the alien channel can also be used to compare across time points to generate a time series profile of gene expression during fracture healing.

Experiments C and D compared healthy tissues in wild type mice and knockout strains with themselves. This method identified genes that could cause problems during analysis. Ideally, ratios of the test channel intensity to the reference channel intensity in the case of these experiments should be 1. However, this was not true for some genes, due to factors beyond the control of the experiment. These genes were removed from the dataset before analysis. Also, differential mRNA expression between healthy knockout strains and knockout strains undergoing fracture healing can be measured using datasets from Experiments A and C.

Experiment E checked whether the alien oligos cross-hybridize to RNA from the two test samples. The test samples used here were not mixed with the in-spike alien transcripts. Analysis of channel 1 intensities from spots that contain the only alien oligos as well as analysis of channel 2 intensities of spots that don't have in-spike controls showed any non-specific hybridization to the alien sequences. The RNA was labeled and then hybridized on a chip containing the probe mixtures. The intensity readings were collected and quantified. Genes with low intensities in each of the reference channels were filtered out from the dataset. This reduced the dataset by approximately 10% when using the aliens as reference as opposed to more than 50% when using the sample from unfractured tibia.

The data was normalized as discussed in the Methods section of Example 5 above, using both the sample from unfractured tibia as well as the alien reference. Data from the microarrays in Experiment A was concatenated with data from microarrays in Experiment B and a common list of genes for which information was available from both set of experiments for each time point was identified. This helped in

TABLE 1

Experimental design to compare mRNA expression levels in fractured vs. unfractured tibia in wild-type vs. TNFα receptor knockout mice.

| | Experiment | | | | | |
|---|---|---|---|---|---|---|
| | | | | | E | |
| | A | B | C | D | 1 | 2 |
| Ch1 | TNF-α receptor KO fracture | Wild-type fracture | Wild type (T = 0) | TNF-α receptor KO (T = 0) | WT (T = 0) | KO (T = 0) |
| Ch2 | Wild type (T = 0) | | Wild type (T = 0) | TNF-α receptor KO (T = 0) | In-spike transcripts only | |
| Ch3 | | | Anti-alien to AO892 | | | |
| Time points | 5 | 5 | 1 | 1 | 1 | 1 |
| Replicates | 4 | 4 | 4 | 4 | 4 | 4 |

In Experiment A, the different time points of fracture healing for the TNF-α receptor knockout mice were compared to the reference. There were four replicates per time point, including a dye swap. In Experiment B, the time points of fracture healing in wild-type mice were compared to the reference again with four replicates per time point. The performing an indirect comparison of the genes in each of the knock-out time points to those in the wild-type. Differentially expressed genes were then identified using both indirect comparisons to the sample of unfractured tibia as well as the alien channel. Table 2 compares the data available from indirect comparisons for each of the time-points of fracture healing.

TABLE 2

Results from indirect comparison of fracture healing in TNF-α receptor deficient mice to that in wild-type mice. The table compares results from using unfractured tibia RNA and alien sequences as common reference.

| Time-point | Unfractured tibia as reference | | Alien sequences as reference | | Genes identified using both methods | |
|---|---|---|---|---|---|---|
| | Total No of spots | Genes identified as differentially expressed | Total No of spots | Genes identified as differentially expressed | Total No of spots | Genes identified as differentially expressed |
| 3 | 7704 | 374 | 10687 | 528 | 6382 | 200 |
| 7 | 7981 | 378 | 11752 | 567 | 6823 | 147 |
| 10 | 7950 | 385 | 11486 | 552 | 6657 | 165 |
| 14 | 8026 | 379 | 11664 | 546 | 6887 | 197 |
| 21 | 9010 | 339 | 12644 | 593 | 7871 | 86 |

As can be seen from the data in Table 2, more genes were available for analysis when using the alien sequences as reference. Most of the missing data in either method is due to the initial filtering step when spots with low intensities are removed. Since there were more genes available for analysis while using the aliens as reference, that method also identified more genes as differentially expressed as compared to using the sample from unfractured tibia as reference. There were some genes that were identified as differentially expressed by one method but not by the other. RT-PCR experiments would need to be performed to verify which of the methods provided better results. Some cytokine-related genes were identified as differentially expressed only when the alien sequences were used as reference. These genes showed little or no expression in the sample from unfractured tibia.

Figure 11:
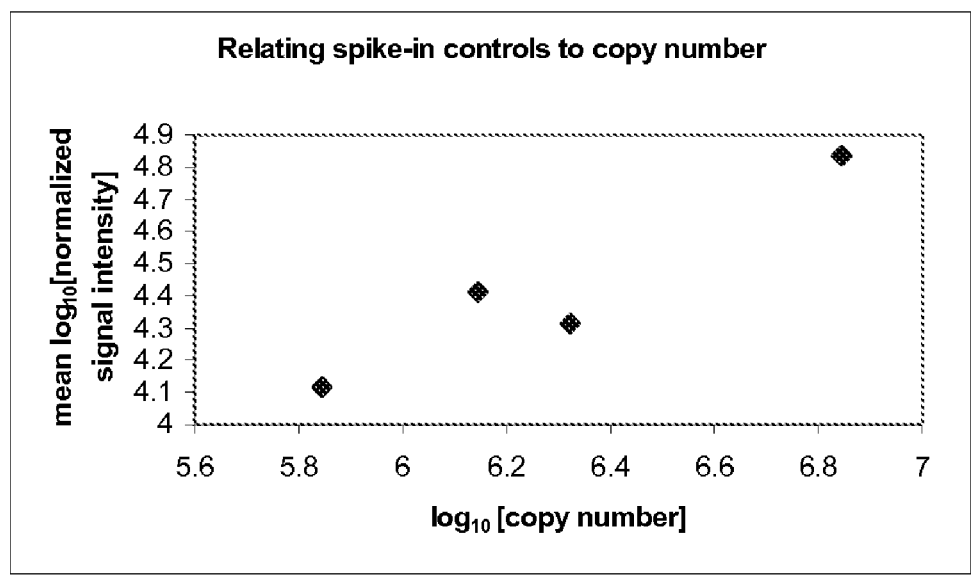
FIG. 11 shows the relationship between the mean intensity values from spike-in control spots to copy number.

Data from the in-spike control spots on the microarray was also analyzed. The three alien transcripts were spiked into the test samples at different concentrations. The mean normalized $\log_{10}$[intensity] values for the spike-in control probes was used to define a standard curve relating signal intensity to copy number (see FIG. 11) for estimation of endogenous transcript abundances. There was a large variation observed in the raw intensity values but there was a good correlation between mean $\log_{10}$ [intensity] and $\log_{10}$ [input copy number], with $r^2 \geq 0.90$. This correlation increased to $r^2 \geq 0.98$ when data from alien oligo AO732 was removed from analysis. AO732 was present in alien genes A and B. There may have been some competitive hybridization between the two transcripts for the alien oligo and this may have affected the analysis.

What is claimed is:

1. A method of generating an alien sequence comprising steps of:
   A) providing a naturally-occurring sequence;
   B) determining one or more natural sequence statistics of the naturally-occurring sequence;
   C) applying a Hidden Markov Model algorithm to the one or more natural sequence statistics of the naturally-occurring sequence to generate an alien sequence, wherein the sequence statistic is selected from the group consisting of: codon occurrence, codon boundary di-nucleotide frequencies, and combinations thereof;
   D) generating and displaying the alien sequence, with the proviso that, at an adjustable frequency, at least one of the natural sequence statistics of the naturally-occurring sequence is switched to a sequence statistic that is inversely proportional to the natural sequence statistic,
   such that the alien sequence comprises intermittent highly improbable sequence patterns or subsequences throughout its length.

2. The method of claim 1, wherein the adjustable frequency comprises a frequency of about 1 in 5.

3. The method of claim 1, wherein the adjustable frequency comprises a frequency of about 1 in 10.

4. The method of claim 1, wherein the alien sequence is about 50 to about 70 nucleotides in length.

5. The method of claim 1, wherein the adjustable frequency comprises a frequency between 1 in 5 and 1 in 10.

6. A method comprising steps of:
   A) generating an alien sequence according to claim 1,
   B) generate an array comprising a solid support and a plurality of nucleic acid probes attached to the solid support at discrete locations, wherein at least one of the probes is said generated alien sequences,
   C) providing a hybridizing mixture comprising a plurality of nucleic acids; and
   D) hybridizing the hybridizing mixture to a nucleic acid array.

7. The method of claim 6, wherein the step of providing a hybridizing mixture comprises providing a mixture containing at least one anti-alien hybridizing nucleic acid whose sequence comprises a sequence complementary to the alien probe.

8. The method of claim 7, further comprising a step of: measuring hybridization between the anti-alien hybridizing nucleic acid and the alien probe.

9. The method of claim 8, wherein:
   the hybridizing mixture contains both the anti-alien hybridizing nucleic acid and at least one experimental hybridizing nucleic acid of unknown quantity; and
   the plurality of probes attached to the microarray includes at least one cognate probe whose sequence is complementary to at least part of the experimental hybridizing nucleic acid.

10. The method of claim 9, further comprising a step of: measuring hybridization between the experimental hybridizing nucleic acid and the cognate probe.

11. The method of claim 10, further comprising a step of: comparing the measured hybridization between the anti-alien hybridizing nucleic acid and the alien probe with the measured hybridization between the experimental hybridizing nucleic acid, thereby determining how much hybridizing nucleic acid was present in the hybridizing mixture.

12. The method of claim 7, wherein the step of providing a hybridizing mixture comprises providing a mixture containing at least one anti-alien hybridizing nucleic acid whose sequence comprises a sequence complementary to the alien probe and also containing at least one experimental hybridizing nucleic acid, the method further comprising steps of:
   processing the hybridizing mixture such that the anti-alien and experimental hybridizing nucleic acids are simultaneously subjected to identical treatments;
   hybridizing the hybridizing mixture to the array; and
   measuring hybridization of the anti-alien hybridizing nucleic acid to the alien probe such that information about efficiency or accurateness of the processing or hybridizing steps is revealed.

13. The method of claim 7, wherein the step of providing a hybridizing mixture comprises providing a known amount of at least one anti-alien hybridizing nucleic acid whose sequence comprises a sequence complementary to the alien probe, the method further comprising steps of:
   hybridizing the hybridizing mixture to the array; and
   measuring hybridization of the anti-alien hybridizing nucleic acid to the alien probe such that information about quality of the array is revealed.

14. The method of claim 13, wherein the step of providing a hybridizing mixture does not include providing experimental hybridizing nucleic acids, and the hybridizing step is performed prior to exposing the array to experimental hybridizing nucleic acids.

15. The method of claim 11, wherein at least one alien probe is present in each discrete location on the array.

16. The method of claim 6, wherein the adjustable frequency comprises a frequency of about 1 in 5.

17. The method of claim 6, wherein the adjustable frequency comprises a frequency of about 1 in 10.

18. The method of claim 6, wherein the alien sequence is about 50 to about 70 nucleotides in length.

19. The method of claim 6, wherein the adjustable frequency comprises a frequency between 1 in 5 and 1 in 10.

* * * * *

SEQUENCE LISTING

```
<160> NUMBER OF SEQ ID NOS: 163

<210> SEQ ID NO 1
<211> LENGTH: 174
<212> TYPE: DNA
<213> ORGANISM: Artificial
<220> FEATURE:
<223> OTHER INFORMATION: Alien to Mouse cDNA

<400> SEQUENCE: 1
atggttgggg actgcctctc cccagtcgga tggtccacct ctgcgtacac cccacctgat      60
ccggatgagg ccagatacac ctgtaaggct cctgaccaat tcaaaaagac acgcacctgt     120
ttgcgatccc caaagccttg cctgtcgata agtgcagagg aactcttaat gtga           174

<210> SEQ ID NO 2
<211> LENGTH: 651
<212> TYPE: DNA
<213> ORGANISM: Artificial
<220> FEATURE:
<223> OTHER INFORMATION: Alien to Mouse cDNA

<400> SEQUENCE: 2
atggcctgca ccctggtggt agaggccccc ttgtcaaaaa ctcccgactt gactggtgac      60
ttcaatagct ccttgtcctg gtcttgcctc gacaataacc cggttttggg attagtgcag     120
ctcaaggtgg cctcctcctc tagctataag tcggaggaac ttgatctgga gcttcccaag     180
```

```
cgagccaaga ttctggattc gatcagtggc acttggaaac tccatcttcg caaggagttc    240
cgcctcattg tgtgtatgtc gcatgcctgg aaccggcggc atgcagctga tttgaaccgg    300
tgcaaatgga agggcaagag ggcaggctgg agaggggccc ccgtgctttt tgctcccatg    360
caggtgacgc gcaagtgtgc accagacccc acagagcagt caggcctctt cgataactct    420
ttcctggatc actaccagag tctggcctgc atttacctag ctcccttgc ccgaaagggc     480 tcttctctga ccaaggatgg aaaggtggat tttcagggcc cttgccttcg tggtggccag    540
aattattcga acttttctca gagctcagcg tgttggaaac cgctggacga ccaggaacag    600
atcgcccgtc ccctcagtgt ctcgttgtac tatgcagcct agtgggctg a              651

<210> SEQ ID NO 3
<211> LENGTH: 228
<212> TYPE: DNA
<213> ORGANISM: Artificial
<220> FEATURE:
<223> OTHER INFORMATION: Alien to Mouse cDNA

<400> SEQUENCE: 3
atgccaaagt tgttaaacct gattcgggca gtcggctgct gtgagaaaca gaccctcctg     60
gctgccgaga gcctcaatga ccgggaggaa atctcctgtt tgttccggcg aaacctcctc    120
cagggaatgc ttctgggaga cagagcagat gacaatacca gtgaccacac gatagtctgc    180
tacaccttca tgatcccctc ccacgccagg atgcctggaa gtaggtag                 228

<210> SEQ ID NO 4
<211> LENGTH: 174
<212> TYPE: DNA
<213> ORGANISM: Artificial
<220> FEATURE:
<223> OTHER INFORMATION: Alien to Mouse cDNA

<400> SEQUENCE: 4
atggaagcag agctctgttc acgaggcgtc aacagacgtg acaatactaa acttccactt     60
tcgtctttgc cttcagcttc tcctcatgat tccaagagat gtccgcgctc taagatcgct    120
cacgtctggg acaccagggc cgacggtgag atcgattcgc gaatctttgta ctga         174

<210> SEQ ID NO 5
<211> LENGTH: 306
<212> TYPE: DNA
<213> ORGANISM: Artificial
<220> FEATURE:
<223> OTHER INFORMATION: Alien to Mouse cDNA

<400> SEQUENCE: 5
atgaactctc tgtctgaata cgagacctta aggcggacca tgctgcagag ctctaacaag     60
tgtaactctc tgtgccaaat tgtacaaact tgggttgagg gtggcaaggc caaggccaat    120
atgaatggct accagaagca tttggttcca cttcgcgttc aaatgtggga gatggcaatg    180
cgacttaatg gaacccagcc aaatgaattc cacccggcag tccagcagtg catcctggct    240
ccttacctaa agacttttcct cagtatgcgt cctgattcgc aaacttaccc ggccaagctg    300
agctga                                                               306

<210> SEQ ID NO 6
<211> LENGTH: 156
<212> TYPE: DNA
<213> ORGANISM: Artificial
<220> FEATURE:
<223> OTHER INFORMATION: Alien to Mouse cDNA
```

<400> SEQUENCE: 6

```
atgcctcgag ggcgtactct ggtatctcgt caagcatggc gaacagtgac cggtaaggcg      60
ggatgctctg ggcggtatcc aagagagagc gggaccttga gtctatcgca ttttccctg      120
gggattatgt ctaagcggag ccaggaggag ctctga                               156
```

<210> SEQ ID NO 7
<211> LENGTH: 135
<212> TYPE: DNA
<213> ORGANISM: Artificial
<220> FEATURE:
<223> OTHER INFORMATION: Alien to Mouse cDNA

<400> SEQUENCE: 7

```
atgatgcagc cttgctccaa acaagaaaga atatgcggac ctcctgactc cagcatcgag      60
tccgcgtacc gctcagcctc tctcacttct agccctgcca cgcttgctcc ggccttctct     120
gcctgcccct gctaa                                                      135
```

<210> SEQ ID NO 8
<211> LENGTH: 144
<212> TYPE: DNA
<213> ORGANISM: Artificial
<220> FEATURE:
<223> OTHER INFORMATION: Alien to Mouse cDNA

<400> SEQUENCE: 8

```
atgaggcgag ccctggtagt gtgccccttg gcgggaccct ggaagaacca gcggtccatt      60
gccctggtga aagatcttcc catgaacgcc agcgttgcct catactttat agaaaggggg     120
agcatcagct ggcatttctc atga                                            144
```

<210> SEQ ID NO 9
<211> LENGTH: 165
<212> TYPE: DNA
<213> ORGANISM: Artificial
<220> FEATURE:
<223> OTHER INFORMATION: Alien to Mouse cDNA

<400> SEQUENCE: 9

```
atggggtggg tcaaggccct gcagagtgaa agcggctggt ggtttgtatt ttctcaggt      60
cgagtgagcc tgaaacccga gccgggccta gcgctggttg tacaccaggg ctttgaccaa    120
acagtcacag aatgtctaag cttcacagga aagcccatgt attag                    165
```

<210> SEQ ID NO 10
<211> LENGTH: 561
<212> TYPE: DNA
<213> ORGANISM: Artificial
<220> FEATURE:
<223> OTHER INFORMATION: Alien to Mouse cDNA

<400> SEQUENCE: 10

```
atgatgagct tcgaacattc cgacttctcc aatgtcgagg accgcaagct cttaacggaa      60
gcgatgtcca caggcttcga agtaatcgag tcgccgtgca agatctgcat gccaagcttt     120
ggaggtaaaa caactgcgga tggcaaactc acttccgtga ctcagggcat gaaacactgg     180
tctctcacca gagctagtcc cccggaccag tcgcaaaagg gccgaccta caggagcacg     240
gtgcaagggg agattgaagc gggacagccc ccacatgaaa tctcctccga ctggtacccc     300
atgttcaaga tggaaacaga cagcccgatt aagaatgttc cccaggcaca catgggggag    360
```

```
ttcgggcact gcgacaatct ccccaatggc aacacagtga gcaacccgga gcctagggag    420
aatgggaatg tggcgccggg agtgggctta gacggacagg aagaaatggg ctggctttgg    480
ccggttcgtc cttcttgtat gaactatttc tttaaagcat ccactctctc cttttggatg    540
ggctttcttg agcgccgcta g                                              561
```

<210> SEQ ID NO 11
<211> LENGTH: 480
<212> TYPE: DNA
<213> ORGANISM: Artificial
<220> FEATURE:
<223> OTHER INFORMATION: Alien to Mouse cDNA

<400> SEQUENCE: 11

```
atgggaaaat ctcgctttga gtatgcagtg acgccccttc aagcccaagc ccgcagtttg     60
ggcagatccc tgaataaaag cccggtgttc ttgttttact ctgagactac atccctgcca    120
gccaaggatc tcccgtgtga gtcaggactt gctgtgagag acctgagcaa caggacacag    180
aacagtctag ctatgttttt ggcttcacgg gggatcaaag accctgaaat gaagatgaat    240
tattccatct atttggggca acccttgcaa gaaggtctgt cccccgtgca ggagaacttt    300
tctcaatggg aactcccact cgtggcttac atgagctttt tctgtccctt ccgtgcgggc    360
gaccggggtt cgatccataa tcatctctcc acggtcagag cgaagattga ctactgtggt    420
cagcggtgca gtgcctcaga tccaaggagg ggccctcagg actattctca aatgctctga    480
```

<210> SEQ ID NO 12
<211> LENGTH: 231
<212> TYPE: DNA
<213> ORGANISM: Artificial
<220> FEATURE:
<223> OTHER INFORMATION: Alien to Mouse cDNA

<400> SEQUENCE: 12

```
atgcgggaag agtccaagac tatctcgatc aatggtgtga atggctcat tgatttgcca      60 gctgaaaaaa tcttcacgag gaactatggt gttgccgact gcaggagaag cttctacatc    120
ctgggcctgt ttggttgcca cctggtgact ggagggtacc gaacattcat gatctacatc    180
gggtccattt cttctttcat catgtatgtg ggggtccgga tcattcgttg a              231
```

<210> SEQ ID NO 13
<211> LENGTH: 426
<212> TYPE: DNA
<213> ORGANISM: Artificial
<220> FEATURE:
<223> OTHER INFORMATION: Alien to Mouse cDNA

<400> SEQUENCE: 13

```
atggtgcccc aagtgtgcga gcagtggagc ctgtgttggt cctcgggcgg gttcccaaat     60
cctgcaggct cttatttaga gccgtggtca agcgacttgt ccaggagct tcagtgcccc     120 ggctacagcg gcttcttaag tggccccacg gatttctct ctatgggagt gtcatgtcac    180
ctagcacagg aatcatttcg gttcccactg caggatgatt gcctcctgac caagatgcac    240
aggttgaaag atttctggga ctccaccagc aggtttaagc agctgggcga atctgaggcc    300
cctcagcaga ttcgcaagaa aaaatcatcg tttagttct ggggctcatc ggagaactct    360
gcgcccgcaa ccgaaaatac cagcaagaag tcccaggatt ccttctttga tgccatcctc    420
aagtga                                                                426
```

```
<210> SEQ ID NO 14
<211> LENGTH: 192
<212> TYPE: DNA
<213> ORGANISM: Artificial
<220> FEATURE:
<223> OTHER INFORMATION: Alien to Mouse cDNA

<400> SEQUENCE: 14
atgggtgtgt cgatggccag cttcatgctc tcttctggcc tcctggatgc agagggagaa      60
agcttcatgt cttggcatct cagcagccct ggaacagccg tggaccgaac ggcccaaatg     120
tttattcact tcagaatgat ggggtcaatc ttcagtgtta ccctgacgct tgaagtcatg     180
cggtctctgt ga                                                         192

<210> SEQ ID NO 15
<211> LENGTH: 351
<212> TYPE: DNA
<213> ORGANISM: Artificial
<220> FEATURE:
<223> OTHER INFORMATION: Alien to Mouse cDNA

<400> SEQUENCE: 15
atgacaatgg aaacagggag gcacccggtc atgaaggacc aagcccttga cgaatgcgaa      60
cggtcgatgt ggccggtccc ttcttgggcc tgggagagtt cttgttctca tcgtgtcgat     120
gagggagatg tatcggtact gctggaacag tttcggcacc agactgaaca gctcccgccc     180
atgagctact ttttggacaa gccaaagctg tcttcgttcc aggaagagcc acggctgtgg     240
gtgactttat gccaggagac attgccattt ccctgggta attctgggta tgatgagcag     300
gaagaggagg gcctgtgtct ggtctgtccg ttgcccagac ttcagacatg a              351

<210> SEQ ID NO 16
<211> LENGTH: 153
<212> TYPE: DNA
<213> ORGANISM: Artificial
<220> FEATURE:
<223> OTHER INFORMATION: Alien to Mouse cDNA

<400> SEQUENCE: 16
atgggtaaaa tcaatcacac cacatcgaca cctaccttga gcactttaaa atccccaca       60 tttgaggcct tacgcccgct actatgccct agactggatc ccccaccctc gtctgtccgc     120
ctggcatttg aaggccagtc tcagaaattg tag                                  153

<210> SEQ ID NO 17
<211> LENGTH: 324
<212> TYPE: DNA
<213> ORGANISM: Artificial
<220> FEATURE:
<223> OTHER INFORMATION: Alien to Mouse cDNA

<400> SEQUENCE: 17
atggttcgca aggttgctca caatgttctg tatgagacca tgggtcagaa agctgactca      60
aagtggggaa ccagaaagaa gcagccacaa gggacccgcc tgagcaaacc ttgcaccacg     120
gtggtggagt ggctgtctgc cttcatgtac cgatcccgca agaaactgac gagccgcttc     180
tatctgaaac ctaacatgtc ttccggttct atccgctacg agagcggca accactcttt      240 ttggacagcc tgctttggtc cgacagtgga aagggagcct ttgcctcctg caaatgctct     300
tatgctaaat cattttttga ctga                                            324

<210> SEQ ID NO 18
```

<210> SEQ ID NO 18
<211> LENGTH: 450
<212> TYPE: DNA
<213> ORGANISM: Artificial
<220> FEATURE:
<223> OTHER INFORMATION: Alien to Mouse cDNA

<400> SEQUENCE: 18

```
atgagcaact acctccacat tcgttccccg gagtcggtcc ataacacctt tcctttgtgg      60
gtccatattg ctcaagcaaa gttcggtcac ctacaagcct tgttaaagcg cgagagtggg     120
tttgaagcca acaccgcgaa tgctgggccg ctaggccccc gcatcagcga tgacactcgc     180
aatatccttt tgactggatt gttcctctcc ctgaccaaga agtgtggatg tgtccagtta     240
cagtgtggcc gacagagtag cctcgatgcc aaaatgccat gtgaccagca ctatagaaag     300
gtgcagtctg ccctcagcca gggtctgcag atgggtggtg cgtgggtgaa gcagaaagca     360
agccaggaga ttgccgggtg gctccacagc agcagccttc aagagcaggc cttggatgga     420
tcatccaact tcgccactct gtccgtttaa                                      450
```

<210> SEQ ID NO 19
<211> LENGTH: 720
<212> TYPE: DNA
<213> ORGANISM: Artificial
<220> FEATURE:
<223> OTHER INFORMATION: Alien to Mouse cDNA

<400> SEQUENCE: 19

```
atgcggagaa ttaagtttga gttcaagaaa ataccttctg ttcgtttgta ccggttcttc      60
ttcggttctt gggctaagat ttctaccctg gcatttgtgg aggacaccta tacctatgcc     120
ttctggatgg aaggagcagg cttcactctt gtctcagctg actgcattac ttcccggacc     180
tttaggagtc cacttgccaa ggacccgctg gcttggcggc tcctggatct tgtgcgggca     240
aaaactcaag aagcgcggac gaactcagct ttgtccttga agtgctccct gcctgatttt     300
ggtccactcg gggagatcaa cagagcccag gcctctgaag gccagcagac ctttggctcc     360
tttgagaagc cgtcagagca tgtcctaaca gcaaagaatc agctccaggt gatcataagt     420
tatcccttct gctatctgct catcataccg gaacgtccat cgacagtag caatatgtcc     480
ttgttcagta agccaagggt gccggccttg aagtgattg gagtacgcct caagacccag     540
atgctagtca cgcctttcag tgagttccag ctatattccc gtgcatttct cagagaatca     600
gatttgtctg agagctccct ctgggtgacg atctcttttg acacggcgaa tctgtcttat     660
gtccaagcgg ctgaggaaga gtgttcattg agaagttccc tggcttacac gtggtcttga     720
```

<210> SEQ ID NO 20
<211> LENGTH: 465
<212> TYPE: DNA
<213> ORGANISM: Artificial
<220> FEATURE:
<223> OTHER INFORMATION: Alien to Mouse cDNA

<400> SEQUENCE: 20

```
atggggatga tgctcaactt ttgtctgaga atctactcca gcagaaaggg agacgccatc      60
atgtctggcc cttctgggtc tttccttaga aaaagagtg tgccctacca aacctggcga     120
gcggagcagt ctcgtaaggt aagcgtgtgc tcctcgcagt tttactccca gaccatcttg     180
cgttggcggc cccaggatgc cgaaacagag agacagagga gaagcggctt caagctggcc     240
atgatgcag cgggcaagtg ccagcctgtg aacgaccca cctcttgctc ttatgaagct     300
tacctaaggc ccatctggaa tggtatgagc tttcttgatt ggctgatctt tgtccccatg     360
```

```
aaccttggtg gacacagaca cagcacctcc ctgagcgcga acaaggtcac gtccatttac    420
aaggaatatg caggctattc cacctgctcg tctaccagag gctga                   465

<210> SEQ ID NO 21
<211> LENGTH: 216
<212> TYPE: DNA
<213> ORGANISM: Artificial
<220> FEATURE:
<223> OTHER INFORMATION: Alien to Mouse cDNA

<400> SEQUENCE: 21
atgcagtact gcgcagctgc cgcttccaag ctgttcccag ccttgccgtt aagggcccaa    60
accctcagac actacctaaa tgtggcccta cacaagtctg ccctcctggg agatctggcc   120
tggcggcgga actcggcagg gggccagggc tttatgactc tagggccaaa agagattctg   180
ccagctcagg tggccccagg tggagagttt ggatga                            216

<210> SEQ ID NO 22
<211> LENGTH: 1188
<212> TYPE: DNA
<213> ORGANISM: Artificial
<220> FEATURE:
<223> OTHER INFORMATION: Alien to Mouse cDNA

<400> SEQUENCE: 22
atgtatgcct gtgctgctct cagttcattc cttgccttcc caaagtacgg actgactgcc    60
aagagatacc caaccctgag aacctattgc ctctgcttat tgtggaagtg tgagaagcat   120
attttgtggc aggggatcaa tctaacgatg cgacaggtga gtgccaatgg gacgcccatg   180
gtgaactggg gggtgctgaa gcccaccact caccagattc tcaatggtga cacagactgt   240
ctgtgccgcc cgaggtcatt tggtttgaag gccaatcagg cccgccgacc gaagaagtac   300
caaggctgcc tctcacggag gtgctctgct gacttcctct gttcccatgg ggctgttgta   360
agagatcagt gctcgatgat tcaagtgtct ttgagcaccc ggctgccgtt ctctaatcca   420
tggattcagg tcgctgtcat gaagttcttt tgttacagaa ccaaggcctg cgcatgtaat   480
ggggggggta aaaaagcccct atctgtgagt tggcaaaaat tccagaactt gtacgtgaca   540
cggaaagcaa tcctagtttt cagcatagct aacaagggtt ccctgactaa gataaacatc   600
cagcggaaga agctcagtaa cagggactca gtgacagagt gcgtcttcgg actaacctat   660
aggagctttc taggtaaacg ccatgtattc gaaggagcct cactcttgac gaacggaccc   720
aacccaggga ggagcaagtg gccctgtgaa acaataagcg atcagtatta ctgtttcaac   780
aggaagttgt ctgagagcgg catgtgcttc atgttgtgta gtacctgcag agggtacctg   840
ccgccggact acctgtttgc agctctgctc aagacagtca gccggacacat cgttaaagtc   900 cgccaggtgt tgcttttttt agaactttac cctggctcga aggctagatc aagcgatgaa   960
attccccacg agcacaataa gacgcctgag ctggaggaac ttccgcctat caacagctgt  1020
acccagattg ccatgctcct ttgcagccgc tcctcagtga aaaccaagga cagtacgacg  1080
gcacctgttc tgtgttcttt tttccttaga ctgtttgctg aggaaatccg gctgcgctct  1140
tttgaacggg agtaccgcaa agattcttac aagtacctgc gggtgtga              1188

<210> SEQ ID NO 23
<211> LENGTH: 126
<212> TYPE: DNA
<213> ORGANISM: Artificial
<220> FEATURE:
```

<223> OTHER INFORMATION: Alien to Mouse cDNA

<400> SEQUENCE: 23

```
atggatctcg atctgcggtt cattctgtta tggaaacagg aggagctggg gctgtgtcgg    60
tacctgaaaa tgagaaaatt tagtctgcag tatgggaaga caaaaaaatg ttcctcaccg   120
gcctga                                                             126
```

<210> SEQ ID NO 24
<211> LENGTH: 951
<212> TYPE: DNA
<213> ORGANISM: Artificial
<220> FEATURE:
<223> OTHER INFORMATION: Alien to Mouse cDNA

<400> SEQUENCE: 24

```
atgggcagtc gcgccccatc gtctggtgat gaaactcaaa tccacgaact ctcactcacc    60
ccccgggatc ccaccttaaa ggaggggacc aagaagggcc agctaagggc atcccgtac   120
ttccttcgtg caatgccgtc cttcctttca gtcaacacac cccaccagca gttctaccac   180
cgtcagcggg ccagctttca ggactacgcg ggagatatgg cctacatcga acttttcagt   240
cagatcagtc ctactgcgca aagagcacta cagatgccaa tcaaccctgc gaacgcgggc   300
gcggtatcca tggggaaatc tttccccttc tccatgcttt tgcctcgcaa ctccgtgtta   360
cccccaacca agcgcccgtt ccaaagactt tccattccgc aatctctgac cagcaagggc   420
cactacctga gcctgtatct gctggaagga gaaatcttag caggaaccat ctccaccgta   480
gcggtggtga ccaaatggac atctcagttc tacatgtgtg tgctggctgt cctttacggt   540
caacacgcac cttccttcag tcagagggct gttgaggttg accggaagtc ccaatccaag   600
gccccaaagg ttcaggaaat gtggcgagac gggattaaat tcacgtctgg taaactcctc   660
tcctgttgtg aggggcaccg catcgccttt gactggtcct tcccaaccag gttcatacag   720
attggacgtc cggggagta cattgcagaa tgcttccagc ggtcccggag aaaggctaac   780
ttcctgaacg ttgacataaa cagctgtctg cgcaagagca ttgaaacttt ttttgggaga   840
aactatatgc acccgccgcg cgacccgctc ttttcaggg tgagtatccc ttgctgctat   900
tgggcactag agggacccct tctgtgaatac cccaaattcc ttcacgctta a           951
```

<210> SEQ ID NO 25
<211> LENGTH: 273
<212> TYPE: DNA
<213> ORGANISM: Artificial
<220> FEATURE:
<223> OTHER INFORMATION: Alien to Mouse cDNA

<400> SEQUENCE: 25

```
atggaaccaa tcgcgcttaa catcaactac cagcggatgc tgctatcggg catagctca    60
aaccagatga ttcatattgt gaacaaaatt gatcttgcga ggacccctc ttctgtaacc   120
agatcccggc tcaatgactg tagaggccct ttatgcagaa aggaccaaaa ggctgagcgc   180
gacagccagc ttggcaagcg ggtgcactat gcattgatcc ttcggttcaa tcggccaaat   240
gcgcctgaca gccaggacta ttcgctaact tga                                273
```

<210> SEQ ID NO 26
<211> LENGTH: 198
<212> TYPE: DNA
<213> ORGANISM: Artificial
<220> FEATURE:
<223> OTHER INFORMATION: Alien to Mouse cDNA

<400> SEQUENCE: 26

```
atgcggaagt cgctttcgcg caaactgcgg atggcctgct ccaagggcct ctccggggtt       60
cctgtctcct cttgtcacat gcactacttc gacgggtccc tggtggtgcg gctgacctgt      120
aagaggagac atggcttgtg caaagaacag cagggtatcg cgggcaccat cagacagaac      180
ggcaccatcc taagttag                                                    198
```

<210> SEQ ID NO 27
<211> LENGTH: 213
<212> TYPE: DNA
<213> ORGANISM: Artificial
<220> FEATURE:
<223> OTHER INFORMATION: Alien to Mouse cDNA

<400> SEQUENCE: 27

```
atgtattatc cagatattac gtatcccaag cccagcagaa ttattgagaa cttagatgaa       60
attgtttctc agtcaggatc gattgaaaat cactcccgac cgatgattgg tctgcgtgtc      120
aactctaagt ggatgccact tggaggggggc ccctacaaga tgatgcgaag cagtagaaaa      180
aaggtgagtc agtgccttct gaatgacatg taa                                   213
```

<210> SEQ ID NO 28
<211> LENGTH: 675
<212> TYPE: DNA
<213> ORGANISM: Artificial
<220> FEATURE:
<223> OTHER INFORMATION: Alien to Mouse cDNA

<400> SEQUENCE: 28

```
atgggtgatg tggtcatgac ggaggaaagc tgcagcgcct tggtgtttga acatctgca       60
atgtctgggt tttacaagac atggacaccc cggttctacg gagtgcaggg gcatcgtgtc     120
tcggacctcg ctgctgttca acagccggcg cgcggtgagt ttcgaaggca ccctccaccc     180
tctcaacgac tgtgggcact cctgggtgca tggtggcgtg atctggcat cctggactcc     240
ggggcccctgc gtgaaatgga gctgggcatc cagggtacca tacgattctg gctacctact    300
gcgcgctcgc ggagttgctt gctctgccga tgcctggggg ctgagatcca ggctctcaag     360
ggcaacaacc agaactcatt ctatcgtcag ctcttccgcc aagcttcgta ccgttatctg     420
agatgtagtt tggcgtaccc atcgatgggt gacttcttgc cattgcagcg cggcaagtgg     480
gttctcctgg gcagagggaa gcctccaggg caagctcgag ctctgaagcg cacaggggat     540
ggcaagggggc aggctcgatt aagaacaagt caacttgttc attccctggg agagtatgtg    600
caggttttcc ctttctatcc agaggaccta atgctgagta agaccagga agacagccaa     660
cagagagtga actag                                                       675
```

<210> SEQ ID NO 29
<211> LENGTH: 609
<212> TYPE: DNA
<213> ORGANISM: Artificial
<220> FEATURE:
<223> OTHER INFORMATION: Alien to Mouse cDNA

<400> SEQUENCE: 29

```
atgtcaagtg aaacttcacc ccgcctgatc cctaagtcct ggagtagagg gcgcagcgaa       60
atttcaatcc cttccatcat tgccctgggt gagctgcttg cccgttggag ctagtttct      120
ctctccattg gcaaacgtct tatgcatcct ctgcgccaga catacatgcg aattttttcca    180
```

```
cgaacctttα ttgtcagtaa gatccctgat ggcatggaga tcatgctaag caagtggtat    240
gtggctaatg gaactcccga gcccaagagg ttctgcctga caaccagtca atggctgagc    300
ctttacatga tttccccatg cacatcatac tgcagactcc gcgcatcagc aatgccgcga    360
ggcaggcggc ttgaagcctg gcacggactg agcaaggctg ccaaggagat cactgcatct    420
cggatgtatg cggagatcct cttgtccgag ttaatgccgg tggagactta tatctgttac    480
ttcccgaacc tcgaagccag atgtccacga aaatccccgt tttcgcgtga tgaatggagc    540
atgataagcg taccttgat caacagtgtg ttccgcttgc gcttctcctg gcttgcctct    600
gggccttga                                                             609

<210> SEQ ID NO 30
<211> LENGTH: 789
<212> TYPE: DNA
<213> ORGANISM: Artificial
<220> FEATURE:
<223> OTHER INFORMATION: Alien to Mouse cDNA

<400> SEQUENCE: 30
atgttcacat tcaccagagt tgggtggcct cggtcccatt ggagatccgc cgtggggaac     60
agtgaacgac ccctcttcat atgggcagcc ggtgccctgc ggcccaagga acctcttctg    120
tttcggttgg aaaaaggccg gggtgtggcc gagctgcgga aaggctgag atttttacag     180 tgtgaagcta tgtattcgaa atttctgggg atccctgaaa tgatggaaaa ctccaaggcc    240
gtgatcgtca atttttgcac caaaatcgga cgcaggaat gggagtcgca agcgtcaatg    300
ctcccacagc tgtcaaattt catgacaccg cccagtgaaa gcacgctaag cagctcagcc    360
actttgagga tgagcctcct gtacttcgct tctgcaccca ctaacaagac aaaaattaag    420
ggtgtgaatt tctactcgcc tcccaaccac atgccccta agctgctaga gtgcttgaga    480
catgtgaacc gcgagtgctt caccaacctg ggataccttc tggcttatat gaattgcagc    540
atggacatcc ttaagggcaa gatttctgac gtgatgggac cgcgtgcctc agaagtcaac    600
tcaacagaca gtactatgtg ggtcctgtca acaggagcca ccccaccgt ggttctcatg     660 gaaacaacat gtgcccccct gtcttggagc tacctgcctg ctctgtatga tgcaccgcgc    720
ttcacatccg aaacctacat ctcccttgct gaagcctgtt atcgaagcca ggcctttcag    780
caaatgtaa                                                             789

<210> SEQ ID NO 31
<211> LENGTH: 258
<212> TYPE: DNA
<213> ORGANISM: Artificial
<220> FEATURE:
<223> OTHER INFORMATION: Alien to Mouse cDNA

<400> SEQUENCE: 31
atgtacctca tggcactgaa tatagagcct gaagatctgg cgggattcag caaactcact     60
atggacctgt attttgatga atatgcagat tccatgttgg acaagagtcc cggcctgatc    120
gaatttctga ccgttgggac tccgaagtgt cttctggggc tcggctgag tggtagcgat    180 gcccatcggg ccagtatcgc tcgggactat cgccccatga tccaacaggt gggtctgggt    240
gtcaacttgg tcacatag                                                   258

<210> SEQ ID NO 32
<211> LENGTH: 264
<212> TYPE: DNA
<213> ORGANISM: Artificial
```

```
<220> FEATURE:
<223> OTHER INFORMATION: Alien to Mouse cDNA

<400> SEQUENCE: 32
atgatttccc acacaatctc cgagatcctc accgaagttc agcggcagtt cttctttctg      60
gcctgcaggg gcttcttcta tccgcctctc atgggtggcc gtgaagcttc tgaaactcag     120
ggaatggaat acggcaaggg gtggaacacc catgtccagt gtcgtaagtg caatgattgt     180
gtgtgtctgt tgggggaggt ttatgagaaa ggcataagat acagttgcag tgtgagttac     240
agatccctgg cctacctgca atga                                            264

<210> SEQ ID NO 33
<211> LENGTH: 210
<212> TYPE: DNA
<213> ORGANISM: Artificial
<220> FEATURE:
<223> OTHER INFORMATION: Alien to Mouse cDNA

<400> SEQUENCE: 33
atggaaccta tgtctgcatt accactcgag agcgcattga atgacaaaaa gttcagtacc      60
aagacggggt tgccaagcgg acttaaattt ggagaggttg ctccagcccg agcccccaat     120
ggcttgtcta ggaaagcttc caccaggttc aacagacgg acgttcgtgg caaccagcag     180
catggtctta tcatgatgca gatttgttga                                      210

<210> SEQ ID NO 34
<211> LENGTH: 375
<212> TYPE: DNA
<213> ORGANISM: Artificial
<220> FEATURE:
<223> OTHER INFORMATION: Alien to Mouse cDNA

<400> SEQUENCE: 34
atgcacggca tccactactc gctccccacc cagactgctg acaaagcctt aggtgtgggc      60
atttcctccc aaggccagat tcctcaggca aatgctggca acctcccctt cgccgatgag     120 ccggatggc agatgctcag gatgggtggt ggagaagacc agtcccggtt cacaacattt     180
gtcttgattc gattctgtgt aatcttcgtc ggcaggtgcc aggatatgta cctgctcaaa     240
acaacgccac tgaactgcg ccagaatctc atgtgcctga agatggagtg cactagcgct     300
ctcaagctta aggatgcgca ggtgcagctt gacctcacgc ttcccttttg ctacgccgcc     360
acggtgtcgg cctaa                                                      375

<210> SEQ ID NO 35
<211> LENGTH: 135
<212> TYPE: DNA
<213> ORGANISM: Artificial
<220> FEATURE:
<223> OTHER INFORMATION: Alien to Mouse cDNA

<400> SEQUENCE: 35
atgtcaagct tcaactcaca gtacttcttc ttcgcactgg aacccacgtg gtggttctct      60
atgggacctg aggacattgt gatgcaccag ctcctctctt ttttcaggct gtgtggagct     120
gccagttacc ggtga                                                      135

<210> SEQ ID NO 36
<211> LENGTH: 231
<212> TYPE: DNA
<213> ORGANISM: Artificial
<220> FEATURE:
```

```
<223> OTHER INFORMATION: Alien to Mouse cDNA

<400> SEQUENCE: 36
atgtgccaga gggagagacg attcacatac ccgcagatta gccactgcag ggaattctgc    60
agaggcttca cccaaagtaa agaacctgga ggacatgaca cagctgagta caaggatctg   120
gctgaagccc tgccaatgaa gaacttcagc tgtccggtgc tggaggagag tttcctttac   180
gcaagcgaaa tgagagcttt tctcaagcag caattcgata gttggaggta g            231

<210> SEQ ID NO 37
<211> LENGTH: 180
<212> TYPE: DNA
<213> ORGANISM: Artificial
<220> FEATURE:
<223> OTHER INFORMATION: Alien to Mouse cDNA

<400> SEQUENCE: 37
atgtcctggg tgctcaaaca gtttaaggta atgcgagcca gacctcaatt cctgatggca    60
acttcaacac aggggaatg caccaagaac tggaatgtga ggtggaaaat atgggatctc    120
tcaatgctgc ttgactctca taacacctct tactttaca tttgcgatcc ggtagtttag   180

<210> SEQ ID NO 38
<211> LENGTH: 123
<212> TYPE: DNA
<213> ORGANISM: Artificial
<220> FEATURE:
<223> OTHER INFORMATION: Alien to Mouse cDNA

<400> SEQUENCE: 38
atgcattggt cccaggtgaa actgttggag cgcttcagta atagcaaaga gacgggtgct    60
gaagatgtgc tagaaaatgc catgccttct gaaatggcct taccccttgg agaaagcccc   120
tag                                                                 123

<210> SEQ ID NO 39
<211> LENGTH: 147
<212> TYPE: DNA
<213> ORGANISM: Artificial
<220> FEATURE:
<223> OTHER INFORMATION: Alien to Mouse cDNA

<400> SEQUENCE: 39
atggattcgc ccacgacatt cacaaagttc acaaactgga ttttccttta ttctgtgagg    60
gacgaccacg tgtggctggt atctccattc cagcagttct gcttcccctt atcctctgcc   120
gcacctgggc cgctggcatg caattaa                                       147

<210> SEQ ID NO 40
<211> LENGTH: 339
<212> TYPE: DNA
<213> ORGANISM: Artificial
<220> FEATURE:
<223> OTHER INFORMATION: Alien to Mouse cDNA

<400> SEQUENCE: 40
atgagaaagg atttggagtg cctcctgtcc aaaggcacat cgaatatgct gaagagtttt    60
ctgatctgct gggggaaggc taccctccgc ttctgcgaag aaatgcctct cacccttgag   120
atggttcacc tctacatgga catccctgat gaacgctggc ctccctctaa ccagccattc   180
tttggaaagt tctactcgac tttcttcagc cgccacagcc tgggcccaa gctccaccgc   240 cctcagggtg caggaaggac acagctgtca gaggtcgtgg gcaacttgcg gtgggatcaa   300
```

```
tactgttggg gcaatcctca aacgcgcagg cccagttga                              339

<210> SEQ ID NO 41
<211> LENGTH: 354
<212> TYPE: DNA
<213> ORGANISM: Artificial
<220> FEATURE:
<223> OTHER INFORMATION: Alien to Mouse cDNA

<400> SEQUENCE: 41
atgccctgcc tgggccgaca ggaactcgcc cgcgcgggag gtgtgccagg aagtgcggat        60
cggaggaaga aagcgttcag gttggaagaa gccagatatc ccctgtacat ggagggtctt      120
ggatctgaga cgcaaggggc agcaaaggat caggccccct cgttccggag cccgagaatg      180
gccctgccct acctaagact ccggcccatc aagagagtcc ccatcatctg gcggatagtt      240
tttcagagcc tccaccctgg cgagaagccc agggagacgt atggaaacgc ataccgggga      300
gaagcggcca gggcagagtt cacccaagag tctgcaagcc aaagcttcac ttga            354

<210> SEQ ID NO 42
<211> LENGTH: 267
<212> TYPE: DNA
<213> ORGANISM: Artificial
<220> FEATURE:
<223> OTHER INFORMATION: Alien to Mouse cDNA

<400> SEQUENCE: 42
atgaccttca tgaacgtatg tatagccggg caagatgcaa cgcagccata ttatagggcc        60
agttacaata gccacagtaa agttcacacc ttggaatgtc gagttgagct caaactcaca      120
gaattaatgc gctgtgcgca tagaggaaag ggcacccgta ccacgcgctg tcttatcact      180
gccgccttaa ttctgtgtcc ccccacctcc aaagaattcg cgtacaacaa cttgctcatt      240
gcttcccaca cttggggcaa tgattag                                          267

<210> SEQ ID NO 43
<211> LENGTH: 210
<212> TYPE: DNA
<213> ORGANISM: Artificial
<220> FEATURE:
<223> OTHER INFORMATION: Alien to Mouse cDNA

<400> SEQUENCE: 43
atggcaccgg acaggtccac attctcttac ctgtgggatc ctcaggatca ccatcaggac        60
gcctccccta gttctccaat tgccagggtg tcatcacctg ccttccgggg ttatgactca      120
gaggacctcg catgcagccc cccctttcag aatgcccagc tttggtgcaa ttcgagaaac      180
tcaactgtaa tgctgtacct cacactgtag                                       210

<210> SEQ ID NO 44
<211> LENGTH: 942
<212> TYPE: DNA
<213> ORGANISM: Artificial
<220> FEATURE:
<223> OTHER INFORMATION: Alien to Mouse cDNA

<400> SEQUENCE: 44
atgagcgtga gggaacgtga ggcttcagac aaatctttct ttttggtctt tgcattttt         60 ttacgaagca gttcattgg gttcatgaga cagtctttgc atagctgtgc gaaagcacgc       120
tgcgcgacgt tcaagcccca ggaacgaatg tgtaaccagc ggaccatggt tgccaacgct      180
```

```
ccggaaccca ggctgatgac actggttgtc cgcttggtcg gccatggcgg ttgcacaata      240
gtcacttctg accccgatc cccccagggt gagaaggccc aggatcgcta caacctcatt      300
cgggtgcccc tgtacccggc tgcctacatc ccctgttact acatgaatgt gctatccatc      360
tcaagggaac ttgagctgct attgagctca atccaggttg aaatgagaca cccagtgagc      420
aacccgggac agttatacta tatctctggt caggtggatc ccggctgtga caggagaatt      480
gccaagtcgc ctcgggatga ccagtcggga tctccccggc agagagatgc acccagctac      540
aaggtttcca cgttttaccg ggctagcaga gctaagagta gactaaaacg gacagacccc      600
aagaggacct catccagtca ttccacgttg attttgttta tgctaatctt ggacacttcg      660
aagttcatgg tgaagtccag ccggacttc actctccttc ttcaggactt ccattcagtg      720
acacggaatc agagctccag atttcagttc aggcggaatc aggaaacagc gagatctcct      780
ggagtggcca ctaaggagac gggagcgttg acacagatgt caccccttc tccgcagtac      840 cgcagagtga ctgagtcgtt tttcttagtg cacggttctc tctctccacg tcggtgcctg      900
gagccctacc ctttagccca actggaggaa atccagaagt ga                         942

<210> SEQ ID NO 45
<211> LENGTH: 357
<212> TYPE: DNA
<213> ORGANISM: Artificial
<220> FEATURE:
<223> OTHER INFORMATION: Alien to Mouse cDNA

<400> SEQUENCE: 45
atgacctacc tgtggatgaa ggcgatcagc agtcatgcca agctgccggc aaacttcacg       60
atacagtcat tctcccagtg cattcaggaa acaaccgcaa gtcctgatag agaactcctg      120
acgatgctga agcccacaag atctcaagaa gagacggacc tactgaatag actgtggccg      180 gataaccctct cttctctgac ggagatgcca atctcccgtt gtctgtgcag aagcatccgc      240
ccttacacct cttcagcgga ctccgtgtct aaagagatgt gccagttttg gcaggtggcc      300
tttggcgagg ctggcaagcg tgaggactgt cctctttacc ccaggtcaat cctgtaa        357

<210> SEQ ID NO 46
<211> LENGTH: 129
<212> TYPE: DNA
<213> ORGANISM: Artificial
<220> FEATURE:
<223> OTHER INFORMATION: Alien to Mouse cDNA

<400> SEQUENCE: 46
atgaaatcct gcgtggatga agaatcaagt cattgctatg gtccgcgcg gtgggaagcg       60 cttaagcaga gcacgggttt tttcgccact cgtgagcgag agagcggctt caagcaggat      120
gggtcctga                                                              129

<210> SEQ ID NO 47
<211> LENGTH: 156
<212> TYPE: DNA
<213> ORGANISM: Artificial
<220> FEATURE:
<223> OTHER INFORMATION: Alien to Mouse cDNA

<400> SEQUENCE: 47
atgctgctga tgccagagtt gttagaaaca aaggactcaa tggaagccga atccaaattg       60
aagagcatca gcatgcagaa ggctgagttc aaagaggggg gcatttcttt aggaaaacgg      120
ctcacatcgt acccgaaggt ccctctggaa tcttga                                156
```

<210> SEQ ID NO 48
<211> LENGTH: 240
<212> TYPE: DNA
<213> ORGANISM: Artificial
<220> FEATURE:
<223> OTHER INFORMATION: Alien to Mouse cDNA

<400> SEQUENCE: 48

```
atgttcgcct tcttagatct gactagtttc attctcgcgg gccgggcttg gtacactacc      60
tcaccctctc ctgacaccga aatctggcat ttaccgcctt ctggtgctga gctgtgcaaa     120
gcttgcctct tgcgaacccg caatgcgaca acagactctg agtaccacac tatttcccgg     180
aagtacttaa ttgaccccat ctcacagctt tcgctgttta ccttaatgca cctgctctga     240
```

<210> SEQ ID NO 49
<211> LENGTH: 138
<212> TYPE: DNA
<213> ORGANISM: Artificial
<220> FEATURE:
<223> OTHER INFORMATION: Alien to Mouse cDNA

<400> SEQUENCE: 49

```
atgatgagca agcatcacac cccaaccacg gtactctgct gccaaaatga agacctgcag      60
ggaaccccga ggctgcgagt gctgaaccca atcaaaata cctggggcat catcaacttg     120
gcctacagaa gcatgtga                                                   138
```

<210> SEQ ID NO 50
<211> LENGTH: 201
<212> TYPE: DNA
<213> ORGANISM: Artificial
<220> FEATURE:
<223> OTHER INFORMATION: Alien to Mouse cDNA

<400> SEQUENCE: 50

```
atgaacgaca tgcatgcgct ctttgcgacc aaaacacgta tcaccgagag gggaaataag      60
ttcttctccc agccctcgac caactggaac acgttccagg cagaggagca ctgtcagtcc     120
ctcagagcgc cactccgtac cagcggtatg tatggcccct catgctcagc gtacctcttt     180
gatatacttc tgatctcgtg a                                                201
```

<210> SEQ ID NO 51
<211> LENGTH: 240
<212> TYPE: DNA
<213> ORGANISM: Artificial
<220> FEATURE:
<223> OTHER INFORMATION: Alien to Mouse cDNA

<400> SEQUENCE: 51

```
atgatgacgc ttggttttgt ggaggcccaa atccactctt tacctctgac tctgagcgtc      60
ctctgctgtt tgaaaatgga tcagatggga tccattgagc ctgacagaaa gaaaacccca     120
gagctcgagc tgatgcccgc actcttggcc ccgagtcgtc agccaaagtt cctgccagcg     180
gcggatcttc tcccagaggg tgctcagacg tctaccctcc tcctgggtca ggcaggttga     240
```

<210> SEQ ID NO 52
<211> LENGTH: 123
<212> TYPE: DNA
<213> ORGANISM: Artificial
<220> FEATURE:
<223> OTHER INFORMATION: Alien to Mouse cDNA

```
<400> SEQUENCE: 52
atggaagaga atggcctggc acattcctac actggggtga agttacgggc caatgacact    60
ggctccctgg cgctgcgtaa gcagtcagat gtctgtgttg agtcccagac agcaagtgcg   120
tga                                                                 123

<210> SEQ ID NO 53
<211> LENGTH: 156
<212> TYPE: DNA
<213> ORGANISM: Artificial
<220> FEATURE:
<223> OTHER INFORMATION: Alien to Mouse cDNA

<400> SEQUENCE: 53
atgaccttgt tcctttccgg cctgtacccc aagtgggccg tgagccagag ccactatcaa    60
tcctgggagg gacccgacat cgctgaaggg accatcgagg atcacctgga gcgcctcaaa   120
ccggtcatga gagccttgat taatggtggg acgtaa                             156

<210> SEQ ID NO 54
<211> LENGTH: 225
<212> TYPE: DNA
<213> ORGANISM: Artificial
<220> FEATURE:
<223> OTHER INFORMATION: Alien to Mouse cDNA

<400> SEQUENCE: 54
atgacacagt actggaggat tttgatcgtg ctgcgaattg atctgccggt ctccttccta    60
cagttctatg gagagagccc ccctcagtgg ttttgccgcc ccaaacgctg cttaaaaagg   120
tctcggtcga acggactaaa ggcacgatgc aattggcccc ctgttagctc tcgcacctac   180
atcaagttca agacaatgtc ctatgctctg aagtggacac cctga                   225

<210> SEQ ID NO 55
<211> LENGTH: 882
<212> TYPE: DNA
<213> ORGANISM: Artificial
<220> FEATURE:
<223> OTHER INFORMATION: Alien to Mouse cDNA

<400> SEQUENCE: 55
atgattgtgt tgaagtacat cctcttgctg tgtatttaca taaacctcct ggggtgcaga    60
aatgcaaaga ctagctgtga gtgtcccagg ccgaccatta ggaagtatgt caggcagcct   120
tcaatctctt gttacatgca ctggtgctgc atcggaaca caggtgagca gactgacagt   180
ggtcttacac ccaggcatga tcggcgtagc cctgacatgg ctaagggtca gcaatgggtt   240
gtcccggcaa tgggcagttc cggggggccat gagccgaact catctgcata cttatgctcc   300
agaggaatat acttcagaga ccggaatgaa tgtgccgagg gcctgctcca cacttggccc   360
ctggtgtatg acttcgtgat agaactaaca caacggttcc cttacaactc tcgggtcac   420 ggcattgaag acatagaatc cttcaaaaat tggaacttgt accggacttt cgtcatctcg   480
gagggctata aactactgaa catcaagaga tcaccaaagt ctgagttatg ctcaggacgt   540
atggcttttt ctttcctccg gctgtttctg ttccacaaga cagccccg tggtaaaatg   600 gcaatgcgct atgagggcaa gtggatcttt cgtggggaag gcacagagag tggcgttgtc   660
cctctcaggg tcggactttc caagagcgca ggcaaagata ggatgtgtca gaccccatg   720 accttagcaa ccaagggtcg aaatacccga ggcctgcagg gctaccgcct catcaagctg   780
aagtgtgctc acctgtgccg gatggatgat caggagaggg cggtccgggc catggccatc   840
```

```
ccattcaatg gcaagggtgg ggtgacactg tctatgctgt aa                              882

<210> SEQ ID NO 56
<211> LENGTH: 264
<212> TYPE: DNA
<213> ORGANISM: Artificial
<220> FEATURE:
<223> OTHER INFORMATION: Alien to Mouse cDNA

<400> SEQUENCE: 56
atgaagcttt gtcctatgag gtggctaggc ccgaacaagc caaacaacct ccacctgtat           60
ttgccgccta tggtcccata ccgccacgga ttgaggtgca catttttcaa ggccgacttc          120
tgcagggacc cctgttggac aaatatgtgg ccaatcctca ggcgaaatct gattgcgcag          180
gcagggctgt actgtccgtt tcaggtccca ctcctggaga tgtctgattt ctccgctaac          240
cgagaagaaa tctgggctgc ctga                                                 264

<210> SEQ ID NO 57
<211> LENGTH: 327
<212> TYPE: DNA
<213> ORGANISM: Artificial
<220> FEATURE:
<223> OTHER INFORMATION: Alien to Mouse cDNA

<400> SEQUENCE: 57
atgccggttg cgcggtatcc cagtgacagt ctcaaactgt ctctgaaatc caaggcctgg           60
gtgttccatc aaaaccctac tgggcccttc acgacaaccc ggcccgtcgg ccgcctgcag          120
gggcggcagc agccccccct tggaggtcag aagaagttgg ccgaggagca tcctagacgc          180
tccctggcca aactgaaatc ggctggggcg agcactgggg gacttaatat tggggatgat          240
cggaccttcc cgctgtgcac gtcggcctcg ctcagcagac ccctcaaccc taagagtaaa          300
cagagcaaca ttatttgcat ctcctga                                              327

<210> SEQ ID NO 58
<211> LENGTH: 225
<212> TYPE: DNA
<213> ORGANISM: Artificial
<220> FEATURE:
<223> OTHER INFORMATION: Alien to Mouse cDNA

<400> SEQUENCE: 58
atgacaggta tcttttgctc ttatgccact aaagctggaa ctgcaatgtc cttgagattg           60 cccccctgtaa aggccagcaa tgcctgtgac ctgagccctg aacatgtcc tcaggaccta         120 gatagtgaaa tgatcaatca ccagtattgg aatcgcctgc ggcagattca atgcggtttg          180
aaatctattg acatctttgt caaactaaga ccttctgtca gctga                          225

<210> SEQ ID NO 59
<211> LENGTH: 339
<212> TYPE: DNA
<213> ORGANISM: Artificial
<220> FEATURE:
<223> OTHER INFORMATION: Alien to Mouse cDNA

<400> SEQUENCE: 59
atgaaatacc ggtgcttggg gcagctcact gcctcttaca ccatggcgga atatttggca           60
ttggcaaaaa caggattatt tcccaatagg ggttttcctc gcaagacaga ggggacttgg          120
gagtccagcc tgcctcagtc cttcgaagat aggggaggct caggacgcct gacctcactg          180
```

-continued

| caccagttcc ctgatgtgat ggccaaagag gaccggaaaa ccgaggactt tgcggtcagc | 240 |
| tctctcccag agatccagcg cgtctccacg ggccggccag atatgagata tatgccggaa | 300 |
| tacattgata atggccccgg cagcaactgt gtgttttag | 339 |

<210> SEQ ID NO 60
<211> LENGTH: 321
<212> TYPE: DNA
<213> ORGANISM: Artificial
<220> FEATURE:
<223> OTHER INFORMATION: Alien to Mouse cDNA

<400> SEQUENCE: 60

| atggacggag actcccacta tcgcacaggg gggaccaagc aggatacccct ggtccagtac | 60 |
| acattgctcc ctgaaattga cttttttcggg gggattgctc agaatatgat gatcatgcga | 120 |
| gttgccagaa ccccccccatt tgttgcagaa caccgtcagc ttatgcagga tggagggcca | 180 |
| gagcagagaa atatggaggc ccgtgaacca gcccaccggc tcactaaggc gatgtatgtg | 240 |
| tcatgcaaag cagaagtcaa ggggatggtg acgagcctct ctggggtgcc gacctgcggc | 300 |
| ctgccatcgg aaaaggagtg a | 321 |

<210> SEQ ID NO 61
<211> LENGTH: 192
<212> TYPE: DNA
<213> ORGANISM: Artificial
<220> FEATURE:
<223> OTHER INFORMATION: Alien to Mouse cDNA

<400> SEQUENCE: 61

| atgcagatga ttgtcccaag tggggagaca aagatgtacc ctccgctgga ggccctccag | 60 |
| gaggatgact gtatccaggc ccagtggctg cacacaacct cccaaagctt ccatgagtta | 120 |
| gtgttaagga atgcagtccg cacaccatca aaggttacca aattcccttg caaaaagttc | 180 |
| tgcgtcattt ga | 192 |

<210> SEQ ID NO 62
<211> LENGTH: 666
<212> TYPE: DNA
<213> ORGANISM: Artificial
<220> FEATURE:
<223> OTHER INFORMATION: Alien to Mouse cDNA

<400> SEQUENCE: 62

| atgagctgcc ctttttcttct tcgtggcatt cagatgcctt ctctggagag aaccttcgtg | 60 |
| tcagatcctg gctattccat ccattttgga tctgaaatgc ttgatgttgc tcatcttgct | 120 |
| tctggcacag agcaagtcca ctgggcgaca ctagaatgtg actcgcagct cggaaggaca | 180 |
| cttgagcctc ttgaggagat cactctaagt tgggtgttgt tcctcctcaa gttctttttca | 240 |
| gaagacatct ggaaacttaa atccaaagaa cgttccggcg atgacatgct tgagaggatc | 300 |
| acatcaatgg agctcttgct gccactgaga cggctagaac agctaagctt ctattccttc | 360 |
| ttctctcagt gtactgccct tcgccggagc aagaccagcc caccaattcc tctgtgcgtg | 420 |
| tccctgggca gttgccataa gcagcaaaga acctggctgt acaatgcact gatcaagtac | 480 |
| ggggcttcga ggagaaggaa ggtccccaag cggatgccca ttgagagtcc gttcagcctt | 540 |
| gatgaggagt gtcttccatt ttcagtaatg cggcaaaggg agacacggac aattggcctc | 600 |
| acacccatca tgcagttcct gacctgttcg cccgtaaaga gtgtggatcc gagccggagg | 660 |
| gcatga | 666 |

<210> SEQ ID NO 63
<211> LENGTH: 1311
<212> TYPE: DNA
<213> ORGANISM: Artificial
<220> FEATURE:
<223> OTHER INFORMATION: Alien to Mouse cDNA

<400> SEQUENCE: 63

```
atgatcactg ccaaagatga gaccagatgt ctgcattcct cccgagtaga tcggtatcgg      60
acacttgcgg acccgatgtc tgaggagatg tcgtgttgcc tcctggttgg gcgcgttcac     120
gccaagggcc tctttgacaa aattgtccta atccagaatc ccttcatcct ccacgacttt     180
ttcatgcggt tcccttctcc ctcccaggta cctctatatc agcgctacaa acaagacctt     240
gataaggacc tgtgttccag cctgccttgg tactacaacc cgaagctgcg gcagcgcact     300
tcgcagctca cctacaagct ccgcacaatc tctgttggcc aagacaaga ccatggcacg      360
aagacgtctc tcccaatgct gactattacc caggtgactg cactgagcga cctgagaatt     420
tttttctctg gatttgggga ggacctcccc ctggagccct ttttctcact cctttcgtgt     480
tatcggtgcg ctttctgggt tttacagttc ctgctctata caaggaatgg cctcaagtac     540
agcaaggcgc atgacaaaga gtgtccatgg cccttcatgt ccaacttccc acatgcccgg     600
gcctgtcggg gttggctgtt ttcgtgcttc agaaagacaa gaactttacc ctcattcgac     660
agcgtgaggg agatagtctt agcctcaaag tcctccgata ggtacatgaa gcattcagtg     720
catcggagct gcagttcaac agagggtgcc gaatccaaga cgagcctgga ctgtcttaat     780
tcaatgcaga agaagaagcg tagagatgaa gaattactcc aaacaaatga atttatgatc     840
tcctgtggat ccctggctgt gcaataccga agcatctccg gcataattta tttgctccgg     900
gagcagcatt acatgcacca gacccgcacc agtttttcagt ttacccagga ccaatcgttc     960
ctggctcggg agaatcacaa ttgggggggt gcctctaatg actacctcct gcgcgagaag    1020
ctggatggga agccaatgag aggcatgatg ctgtcccaac acagcgtggc atgtggtttg    1080
cagggcaaac ccattgcaac caacctgttc aagccttcag tgaacttggc agaagagttg    1140
tctgtgaaat acactggagc tttcctgcgc tcagacgccc tgctacagct ggctcaggcc    1200
ggactgtggc cccagaagcc gtacctgatt tggagaatca gggtggaaaa gacccacgaa    1260
tggggcacgg gtgaactggc gctgagcatg gtcctgagct gcttagactg a             1311
```

<210> SEQ ID NO 64
<211> LENGTH: 306
<212> TYPE: DNA
<213> ORGANISM: Artificial
<220> FEATURE:
<223> OTHER INFORMATION: Alien to Mouse cDNA

<400> SEQUENCE: 64

```
atgtgctatc catcgcctga ctggagaatt gtgataataa cccagttact gaatacgaga      60
tggatcgcag tcagggcact cttcatggca agtggacgca agccttgttc aaaggtgatc     120
caagccgcca ttgcctcaat ggcacagctg ctctatgtgt caaaggccag cacattagta     180
gggtcagtga tggagggaag cgaggactgc agttgcgagt ttcctgatat gcctggtatt     240
atgggagatg tcccttcccc aatgttcact cttggcatga tcctgccatt aaccttgttt     300
caataa                                                                 306
```

<210> SEQ ID NO 65

<211> LENGTH: 264
<212> TYPE: DNA
<213> ORGANISM: Artificial
<220> FEATURE:
<223> OTHER INFORMATION: Alien to Mouse cDNA

<400> SEQUENCE: 65

```
atgctgacac tttgcatgat cctccaggcc ccgacaaaga gaatgatgga tggatctgaa    60
agtggagtgt tgcagttcct gcggagtcgc tactcagggt acctgggaga tcccatggca   120
tttctcgagg atgattccag aagtaagccg acggagagaa ccggccttcc tgtggagatc   180
cacatgatgt cgtttctgga ataccatggt gaactggtca acttcttctg gcgcagaagg   240
cagcttcagg acgaaggact ttaa                                          264
```

<210> SEQ ID NO 66
<211> LENGTH: 360
<212> TYPE: DNA
<213> ORGANISM: Artificial
<220> FEATURE:
<223> OTHER INFORMATION: Alien to Mouse cDNA

<400> SEQUENCE: 66

```
atgcacaggc cactggggac taacaaggga agtgccccag tggagggtta ctctcgtcgg    60
cccaggccaa aaaagagcc aaattccctc ggccgcatgt tctgcatccg ctcagcttcg   120
aacaccaatg agccttacac cttagatcct gaagactaca tgaaagcaga cgggagagta   180
actgtggtcc cggaagccc agcaggcctg acatccagaa gttacttaga gcgcccccca   240
ggggaacaaa cacgggagcg gcccttaggc attttggtcc cttatatgcg agccccgaag   300
aaatactctg actacctgat gacattctgc acgcgtaagc ccttccataa gtccccatga   360
```

<210> SEQ ID NO 67
<211> LENGTH: 285
<212> TYPE: DNA
<213> ORGANISM: Artificial
<220> FEATURE:
<223> OTHER INFORMATION: Alien to Mouse cDNA

<400> SEQUENCE: 67

```
atgcacttgc actacgatcg catgttattt atgcagcacg aaacgttggt tatatctatt    60
tcgcagatca atgacctctc ttgcaccacg tcaccagcca cgatgggcag gtgcataacc   120
tgggggccca cgaggacaac ttttctgctc tttcgggaga ctgatgtcag ccacctgtgt   180
ttgatcaaac agctgagctt cttcagtcag atcctgcagt acaagcagct catgtcgaac   240
atatcggagc gcacgggacg atacatcaga agctaccatc tctaa                   285
```

<210> SEQ ID NO 68
<211> LENGTH: 663
<212> TYPE: DNA
<213> ORGANISM: Artificial
<220> FEATURE:
<223> OTHER INFORMATION: Alien to Mouse cDNA

<400> SEQUENCE: 68

```
atgaggcact accctgcttg gcaagcctca gccatgctct ttgagtacac tggggatggt    60
ctccagcagt cccctagtct tctgagtctg ggctcaattg ccaatacggt gatcatacga   120
acggaccggg ccccacagga gcgaacgtcc tgccataatg gtgaccttat caagagtgcc   180
ggcacctccc tgctggatat gcgagatccg catgtgtcag cggagggagt gactccctcg   240
aacctgatga tctgcaagac tccaccctct ggtttctgcc tgtctcactc ggactgctct   300
```

```
ggagaaaagc agatggctct gagaatgtca gccagcaata tctttcaggg tcggaaaacc    360
ccggcctctc cttgccagtc gacagctacc tgcattctct ggtactccac ctcaacccgt    420
gctgactata ttcggcagtt ttacctgtgc acccgagcga atgggcgagc tccccgccag    480
aactgcattg gcatgggcat actgtcattg tattctccgg tccagatcga ctcccctccg    540
ccccagtgcc caacacccct gttgagcctg gtcggccggg tgacgaggga gtcacagcag    600
gttggggtgc aacgagccct aatgctgggt acgagcaccc ctctgctcaa ccgccgcaag    660
taa                                                                  663

<210> SEQ ID NO 69
<211> LENGTH: 120
<212> TYPE: DNA
<213> ORGANISM: Artificial
<220> FEATURE:
<223> OTHER INFORMATION: Alien to Mouse cDNA

<400> SEQUENCE: 69
atgcggattg atgaagggac ccaggaggag tgtgagctct gcgctctggg cacgaagagc     60
ccagccatca tttcgcctcg acagtacaga attcgaactg tgggtttcat gctcagctga    120

<210> SEQ ID NO 70
<211> LENGTH: 249
<212> TYPE: DNA
<213> ORGANISM: Artificial
<220> FEATURE:
<223> OTHER INFORMATION: Alien to Mouse cDNA

<400> SEQUENCE: 70
atgctatcgg aggcctcgag agatcgcgtg acggaaatgg ccatgatgac agattcttat     60
cacctgccaa ccatgcctct ggcccctgag tactctggca cgtttaggga agctcttgg    120 cgaacatctc cacatgcgat tgatccaggc tggcagagcc aggtgtgtga gcagcatgat    180
aaccgcttga cagggagtc aatcgctcag gtcgcttatc agagagggat ctggatgagc    240
aagaactga                                                             249

<210> SEQ ID NO 71
<211> LENGTH: 438
<212> TYPE: DNA
<213> ORGANISM: Artificial
<220> FEATURE:
<223> OTHER INFORMATION: Alien to Mouse cDNA

<400> SEQUENCE: 71
atgtacatgc cgatttacga gcccaagatg gagatgtccg gtcagcccag aatcgaaaag     60
gcccatcggg atggcaagtt agcgacccag ctctcttccg aatatttcac cgagaaggag    120
ctagacctgg ttgaccatgc tgagtcttac ccaatgatag tgggagattt tgggggcacg    180
cccaccaaga attcaataca gaccccaggc ggatcgatct acggcctggc tcagagggac    240
atcagcttta aattaatgtc catgtccagc agttggaaga atgtgggaag gtatgcagcc    300
cccttttgct taggtctctt tccgcactac gggaacatgg aactacggga acttctgttt    360
tcccacatga aagcgcgcga aaccagaacc acgtcaaccg agtctctgac atccatcaga    420
ctcaggtcag gctggtga                                                   438

<210> SEQ ID NO 72
<211> LENGTH: 489
<212> TYPE: DNA
```

<213> ORGANISM: Artificial
<220> FEATURE:
<223> OTHER INFORMATION: Alien to Mouse cDNA

<400> SEQUENCE: 72

```
atgctgagat acagccggat ggccatcaag caacagcttg accaggtggt ttacacacgg      60
tccctttcat tcacggacct ccacttgcag aacaagcagg caggccctga aaaacatggt     120
aacttcaacc tctggggccg catccgggat ctcaggatgc ggtgtatcct gaagttcagc     180
tggggaggag aggtttttgt tcttcaatca agttgttcct ctgactcttt ctcagttgag     240
attgagttgg cagaggtgag attcctatcc taccagaact cacggttgcc agcgccacgc     300
accgactatc tgagtgcgag ccgcacttct aaaacaagct gttctctgcg cgtgttcata     360
ttgggacacc agctaaactg ccctctgtgc actgctgctt cttttattga agggaaacta     420
tgtagcaacg atactggaga ctacagctgg ccgcaagcgg ccctgtaa ctggtccgct       480
tatctgtaa                                                             489
```

<210> SEQ ID NO 73
<211> LENGTH: 303
<212> TYPE: DNA
<213> ORGANISM: Artificial
<220> FEATURE:
<223> OTHER INFORMATION: Alien to Mouse cDNA

<400> SEQUENCE: 73

```
atgattggaa aagatgagat ctatatgctg tcaaagggac atcagccaag acgtaggact      60
ctgaaggcct caaccccaa cctggtcagg cccaagccgc cctgcaccat ctctgtgcgg     120
gccaccttaa tgctaatctg gtttcccttc cagtgcctga tagctaagat gcagttgacc     180
ctggagacct ggtctccctg gattatctgg ctcaatctta agggatggcc ctgccggatc     240
ctgccgctta tgtacccatc aagaaagtct gcagctgact acactgactc tgtggaaaac     300
tga                                                                   303
```

<210> SEQ ID NO 74
<211> LENGTH: 141
<212> TYPE: DNA
<213> ORGANISM: Artificial
<220> FEATURE:
<223> OTHER INFORMATION: Alien to Mouse cDNA

<400> SEQUENCE: 74

```
atggggctct ggcggaccct gagggccgat gtcaagaaca gcgatccatc ccctttacag      60
aaagggacga aagctaagca ggtggagagc cggaaaatca tggagtacgc gcagacagag     120
gggcacatca cgttggagta g                                               141
```

<210> SEQ ID NO 75
<211> LENGTH: 180
<212> TYPE: DNA
<213> ORGANISM: Artificial
<220> FEATURE:
<223> OTHER INFORMATION: Alien to Mouse cDNA

<400> SEQUENCE: 75

```
atggctcgga acctcctggg aacaggaccc ttttcgcacg aacgccggaa ccagcaaaac      60
gctgagttgg gaactgagag tattatcctt ctggatggag ataggagaag tgcgcgcaca     120
tctggcaaga ggttcaagaa ggtatcttat tacttccagt gtgactgcct gacgctgtag     180
```

<210> SEQ ID NO 76
<211> LENGTH: 141
<212> TYPE: DNA
<213> ORGANISM: Artificial
<220> FEATURE:
<223> OTHER INFORMATION: Alien to Mouse cDNA

<400> SEQUENCE: 76

```
atggagcttc cccgctccag taagcctatg accccgtatc ctgagcgcag cgggatgggg      60
cactggtgga ttatctatac caagcattcc tccagagggt cctctaatat gatctgctgt     120
ggtccagact ctagcaaatg a                                                141
```

<210> SEQ ID NO 77
<211> LENGTH: 123
<212> TYPE: DNA
<213> ORGANISM: Artificial
<220> FEATURE:
<223> OTHER INFORMATION: Alien to Mouse cDNA

<400> SEQUENCE: 77

```
atgctccagg accgctgctt cctcgcaaag tgcctcttat ccagcatgtt atgctattac      60
aaaaaaggct tgagcgaggc ttttggcgaa cccaatgaac agagctgcaa catgcggatg     120
tga                                                                    123
```

<210> SEQ ID NO 78
<211> LENGTH: 177
<212> TYPE: DNA
<213> ORGANISM: Artificial
<220> FEATURE:
<223> OTHER INFORMATION: Alien to Mouse cDNA

<400> SEQUENCE: 78

```
atggaacaag gacctgccct ggaggaggaa aagtcagctt gccagagcct gaccttcacg      60
tttctgagtc cctcgagagg caaccagatg cagtggaact cccaggttgg aagaaactgg     120
actgtactgg tgccaaagga ttgtgctagt gtgtttaaga gttccatgaa cggctga        177
```

<210> SEQ ID NO 79
<211> LENGTH: 174
<212> TYPE: DNA
<213> ORGANISM: Artificial
<220> FEATURE:
<223> OTHER INFORMATION: Alien to Mouse cDNA

<400> SEQUENCE: 79

```
atgcagcagc cgttcgccag ttactccacc agtttcaagt caagtgatct ggcgactaac      60
tccagcacgc agctggtctg ttctggccat ccctcgggac ttcccttcgc ttcaatgttc     120
attagggctt tgtcgccccc tgcgctgcgt ggccccccaa agctcggatc atag            174
```

<210> SEQ ID NO 80
<211> LENGTH: 363
<212> TYPE: DNA
<213> ORGANISM: Artificial
<220> FEATURE:
<223> OTHER INFORMATION: Alien to Mouse cDNA

<400> SEQUENCE: 80

```
atgctgagcc ggtttcttaa ggcctttctg tttcggtgct tcagtgttc tgagcgggaa       60 aaggtggtga agaagctctc aaccatccag attgagaagg aggagccgat cgccctgtct     120
tgtggtaagg ccccccattc tgacctgaac caagtgctcc ccatgtttaa tttcgagttt     180
```

```
tttcatgggc tcaacgtggc cgagaacctg gtgtctggaa ctgcttcgca ggagaaggga    240
caatgctgct atggtttcaa cagcaaaggc cgctctgtcc gggcactgga attcgtgtgt    300
atcagggcct tcagcaacat ccaatcggat gactccagtg acgccccttt tggcctggtt    360
tga                                                                  363
```

<210> SEQ ID NO 81
<211> LENGTH: 462
<212> TYPE: DNA
<213> ORGANISM: Artificial
<220> FEATURE:
<223> OTHER INFORMATION: Alien to Mouse cDNA

<400> SEQUENCE: 81

```
atgagcggga acctccgtat caacccatgg ctgactgcct gcatctgtgg ggaaaagtcg     60
actcagtgtg ggcctgctaa ggccgccaac aacaaacgct ttcccaggga tcaggccaga    120
aagcggctgt attcgccatc cccacccatc ctgaacacaa tgatcctctc ccctaaaagt    180
tgggtcacgc tgcatgttgc gaagaagcag gcccccacgt gttggctgct ctccaccgcc    240
aacttaaaat tccttccatc ccagttgcaa ccggaggcag atcgaaactt ttgtagctct    300
gattaccacc gcactctccc ttgtgcgcag gctatcatca caaatttgga gctgaaaatc    360
tggacctcca ccaaagcgaa cagtcccgaa cctgtggcga aagccctgga gttcaacacg    420
atagtgccat tgtgcaactc agaggaccgc tttattgggt ag                       462
```

<210> SEQ ID NO 82
<211> LENGTH: 168
<212> TYPE: DNA
<213> ORGANISM: Artificial
<220> FEATURE:
<223> OTHER INFORMATION: Alien to Mouse cDNA

<400> SEQUENCE: 82

```
atgtctccca acgacattca ggtgattaca ggcttgcacc aacgcttgcc agtgcttctc     60
aacacccttc gtatgtctga caaggcattc actctttgct gcaagaagac caaccctggc    120
agcctgaaaa tgcagatgcg gaaccgtcac ccggatcttc agaaatag                 168
```

<210> SEQ ID NO 83
<211> LENGTH: 207
<212> TYPE: DNA
<213> ORGANISM: Artificial
<220> FEATURE:
<223> OTHER INFORMATION: Alien to Mouse cDNA

<400> SEQUENCE: 83

```
atgatgaaga ggcgaactct ctctcggatc tgcgacatat ggacagtgta cggatgcagg     60
aaatgtaacc attacagaaa cactattctt cagtccctgt ttctcatctt ctggattgaa    120
atttgtgagg agcattccct tcattcatca ccgaggcaga ccgcctcctc ccagttctac    180
tcaccgagac tcaactccta cgagtaa                                        207
```

<210> SEQ ID NO 84
<211> LENGTH: 144
<212> TYPE: DNA
<213> ORGANISM: Artificial
<220> FEATURE:
<223> OTHER INFORMATION: Alien to Mouse cDNA

<400> SEQUENCE: 84

```
atggaccgcc cacacatcgt gtccatggcc tttttgaact gcgcttcctc agcggccatc     60
```
ttgaagggcc ataaaatccc cctgcccata aagatcctgc gcttcgatcc actctctcaa    120
agtactgaat tcctcgggg gtag                                            144

<210> SEQ ID NO 85
<211> LENGTH: 132
<212> TYPE: DNA
<213> ORGANISM: Artificial
<220> FEATURE:
<223> OTHER INFORMATION: Alien to Mouse cDNA

<400> SEQUENCE: 85
atgatttttc acctgctgtg ctttgctaca ctcgatgtga ccgtgacgca cacagtggcc    60
actgaagcct cgaatggaat gctgatcacg ccctctgaag aaatcaccag caccaggccc   120
gtgatattgt ga                                                       132

<210> SEQ ID NO 86
<211> LENGTH: 192
<212> TYPE: DNA
<213> ORGANISM: Artificial
<220> FEATURE:
<223> OTHER INFORMATION: Alien to Mouse cDNA

<400> SEQUENCE: 86
atgtgtggca caggggttag tttaccttct cagataaaac atgaaaacaa cttttttattt   60 cccgactgga caatgctaaa caagccggaa ctgtacattg cgggattga ggagaactac    120 tgccagtaca agggtcccat ctggatcttc agggtggacc gcagtcaga aggccagcgt    180 ctgaagttat ga                                                       192

<210> SEQ ID NO 87
<211> LENGTH: 492
<212> TYPE: DNA
<213> ORGANISM: Artificial
<220> FEATURE:
<223> OTHER INFORMATION: Alien to Mouse cDNA

<400> SEQUENCE: 87
atgatgtttg aggcctgctg cccactcgcg gattcgcagg ggaagagcaa gtccaagggt   60
ctgaggaagg gagaatctac cccgcttgga gggggcgga agttcctgat gctgtctacc   120
agcctcagca tctactcgtg tattaacatg gccccatct cccttaacgc acacattgat   180
gataacacac tccatcagac attcatgtcg cgctcagtgc ttgagcggct agttggaacc   240
tctcaaaagt tcgatacaca ccctcatatg tgtgctgcag atgctcagta cacaaagtct   300
agacggtgtg agcaggcctt tgggcaccc ttgtcgcctg cgcttgtttt ctccatcctc   360
tctcaagaaa tgggcgacac ccccaagaaa accggtgtc tgaagggtcc ccagtgcctc   420
aagcgctgtt gtcaagagtc ctgcctctct ggtggctttg taatctttga caatccagtc   480
tgctacttat ga                                                       492

<210> SEQ ID NO 88
<211> LENGTH: 222
<212> TYPE: DNA
<213> ORGANISM: Artificial
<220> FEATURE:
<223> OTHER INFORMATION: Alien to Mouse cDNA

<400> SEQUENCE: 88
atgaatgcag aggacatgct ggggaaacac tgcgcttatg cttttgcac agtccctatc    60

```
ccgaagggag ctgtgaactt gaaaaccgag tttgagagtg gctgtgcgaa gtctgccaac      120
ggcaactccc gcaaagacag tgtttcaggt ccatgccta agatgaggca gaagtgggac       180
tggggacccc gagaaggagt ggctcggaca ggagaattct ag                        222

<210> SEQ ID NO 89
<211> LENGTH: 150
<212> TYPE: DNA
<213> ORGANISM: Artificial
<220> FEATURE:
<223> OTHER INFORMATION: Alien to Mouse cDNA

<400> SEQUENCE: 89
atgagagtga gggcacggct gtcaatcccc ttcaccacga gatccatggc cctttgctac      60
cggaagtcgg gggacaccgg ttttgttgtg cagaaggagc cccaggatcg gtacacggga     120
aggaaatgtc aacccgtact gatgacctga                                      150

<210> SEQ ID NO 90
<211> LENGTH: 297
<212> TYPE: DNA
<213> ORGANISM: Artificial
<220> FEATURE:
<223> OTHER INFORMATION: Alien to Mouse cDNA

<400> SEQUENCE: 90
atggagaagc tgtcctggcg tgctggcctc ctccactctc aggatggaat aaccagggcc      60
gcctacccgg gaaaagagca gtcttcccgg ggccgcaatg cgaccttttg gacagctcag     120
cctgactccc gggcggcctc ttactcccag ctctctgtcc agaagtatcg aacaacagcg     180
atgtgcctgc ctgtgtccat gtctagtaat ctggtctcca tggagcagcg gttccggcac     240
aagctcatcc agtggcggtt gtgtctgaga atgtctagtc taaccattat gtcatag        297

<210> SEQ ID NO 91
<211> LENGTH: 129
<212> TYPE: DNA
<213> ORGANISM: Artificial
<220> FEATURE:
<223> OTHER INFORMATION: Alien to Mouse cDNA

<400> SEQUENCE: 91
atgtctttga cagattttct ttctttctgt gttctgagag taatggccaa acatctcaca      60
gactataggg cctcagctca gcttgggtgc tgtgaacagc aggcttctgc atcccgaccg     120
gaggaatga                                                            129

<210> SEQ ID NO 92
<211> LENGTH: 123
<212> TYPE: DNA
<213> ORGANISM: Artificial
<220> FEATURE:
<223> OTHER INFORMATION: Alien to Mouse cDNA

<400> SEQUENCE: 92
atgacggcct tgggggctgc aagttatagc cgttctgttg tctatgatgg ccatccgtct      60
gcgccagagg gtggggccaa gcgtggcaag caggtgaagc catggttcaa gcaattggaa     120
tga                                                                  123

<210> SEQ ID NO 93
<211> LENGTH: 435
<212> TYPE: DNA
<213> ORGANISM: Artificial
```

<220> FEATURE:
<223> OTHER INFORMATION: Alien to Mouse cDNA

<400> SEQUENCE: 93

```
atggtgtggc tcctacccccc cttaccattg agccactgta agaatccttt ccttcgtaag      60
tgcttcaagt ttgagcgctc gtgtgcagga atttcttgct ctgatacgcc gccctactcc     120
tgccgtcagg ccgagagctc cacttcatat ttttacccat tctcaatgac cagaagcacc     180
atgaccatcc cagaccaaac caaaacctgc caggcgtgtt ctgtgacccg gttccctcc      240
cgggaggaaa agaccaagaa cctgatgaca ttctgttaca agatgcatct gcagatggtc     300
ggctatccgg tcaaagacac gttcctcaaa gaggccaagg actctgattc ttcagggact     360
gagtttgagc tggtgaatgg gccaccttt tgtgggctcg ggattcagtt gaactgctgt      420
tcccccagtg cctga                                                     435
```

<210> SEQ ID NO 94
<211> LENGTH: 198
<212> TYPE: DNA
<213> ORGANISM: Artificial
<220> FEATURE:
<223> OTHER INFORMATION: Alien to Mouse cDNA

<400> SEQUENCE: 94

```
atgtccaagg agattcatct gcctgttctg agccgggccg gactccctcc gagttgtgag      60
aagcttcgag gctccccctc tgtgctctcc atgacatttg cctacccct gcccaagcgg     120
agccaccagg caatcgccac ggcgtcccgg gagctcatgc taaccttgga ccctcggcc      180
aaaggaccgg ggtattga                                                  198
```

<210> SEQ ID NO 95
<211> LENGTH: 726
<212> TYPE: DNA
<213> ORGANISM: Artificial
<220> FEATURE:
<223> OTHER INFORMATION: Alien to Mouse cDNA

<400> SEQUENCE: 95

```
atgcccgcga tggccactgg cgcggagtgg gcctctgcca cacggatatg cgaccgttat      60
gcgacttccc acgtgaggcg catgagatca ggggcaagac tgatcaaaca gggagtggag     120
ctgatcaagt accgccccac cacttgcccc tacatagcca tggatgctcg cgaccttttg     180
cgacacattc ggagcccga atgggaaccc tactgctact gtctgacagc tatctcaagc     240
tcaaagaact atcttctgct gtccgtcagg gcccctccat tctcgcaaaa gaaacgactt     300
cccgtggagt gggtccttca gtgtaccccc atctgcaagg cctttcaagg gtcaacttca     360
tacaagctga acatgttctc ctcttgcgcg cacactagcg ctttgacttc aagggattgc     420
aaaaagtcaa tcatgaggcg caaccattgc tactttatc ctttcctgga tggagcagga     480
ttcccggggg ccattacatg caaaatcaga ggatgcattc tgggcatgca gaactctccg     540
gtgggccgcc ttaatggggtg ctgcaagcag tctgtcaggg atgatgagac aaaggcattc     600
ctgcagcccc gtttggtcgg gacgtcaatg gtggattatg tgccgctgca actattctgg     660
gagcaagttc cgctcctcaa gtgttctctt aacccaataa gcttgaaagc cgcagggacg     720
cagtga                                                               726
```

<210> SEQ ID NO 96
<211> LENGTH: 158
<212> TYPE: DNA

```
<213> ORGANISM: Artificial
<220> FEATURE:
<223> OTHER INFORMATION: Alien to Mouse cDNA

<400> SEQUENCE: 96
atgtcttatg acttacggtg gcttcaccgt ggggccacaa tcacagccga aatcatctta      60
tcttgtaagc tcccaaaagt gagaatggat ttctgctggg tgaagcagtc catggaggcc     120
atggtggcca tgaaggacca gaaagacgcc ttttgctg                             158

<210> SEQ ID NO 97
<211> LENGTH: 318
<212> TYPE: DNA
<213> ORGANISM: Artificial
<220> FEATURE:
<223> OTHER INFORMATION: Alien to Mouse cDNA

<400> SEQUENCE: 97
atgaccagaa gctgggccct ggtgccaccc cacctgttgg ttggagccga acaaccccct      60
gtgacttcat atgggtacaa agcgaagagc aacatacgct ttgtgttctc tgaggctttt    120
gaggctcaac agaggcacga aagccgttca accaaccatg cctgggccca gccagcaggt    180
cgaccggtcc atctcattaa ggggcaggag aaatctaggg aaaatttaga tccgagctgt    240
cccaaaccaa agggagcgga ccggagtctc acaaaggatg aacaatgaa gcaacgatac     300
gacttctacc tgccgtaa                                                  318

<210> SEQ ID NO 98
<211> LENGTH: 732
<212> TYPE: DNA
<213> ORGANISM: Artificial
<220> FEATURE:
<223> OTHER INFORMATION: Alien to Mouse cDNA

<400> SEQUENCE: 98
atgaagtatg tttcccagga agcccacctg gtctatgttt atatgtatgc ggatcactac      60
ctcagcagtg tgctgtcttc ccaagatggg cgcccctcaa acttcatcac gcgcctgaca    120
aatgcgagtg acaagtggac taacaagacg aagtccatga aggacagcta tcagggtttg    180
tgggagttgc ctgggatcct ggagctgaga gcacctgaca tggagctgga acttctgacg    240
aatgggaaag ccctgatggc gatccgcatg atcaacatga agaattcccc gcaggatgcc    300
aaagaggcct cgtctgcgat catggccaaa gttcccagtt tagttgtgcc atgctccggc    360
tactttgcct ggcggcagaa gggcttggag cgcaactttg atctgaaagg ccaaagtgtc    420
aaatacagaa aaatacagg tcctggcctg tctccacctc aggtgaggac ctcctatcag    480
gaaaacctgg ggacacccct tctgccacca attcagatga tgagctacct agtgatttcg    540
gacctccccc ggaggtctaa acgtgattgc aggcgggccc gtggagtctt tgccccacgc    600
gagggactag ccaaagaaca gggcaaaagc aagctccgcg cagcttacat tcacaacaag    660
ggtttcgagg gcctgactcg tgaacaagtc caggggtatg ctgagagctg tgacgttctg    720
ccacagcagt ag                                                        732

<210> SEQ ID NO 99
<211> LENGTH: 132
<212> TYPE: DNA
<213> ORGANISM: Artificial
<220> FEATURE:
<223> OTHER INFORMATION: Alien to Mouse cDNA

<400> SEQUENCE: 99
```

```
atgggcacaa agcccttctc actcaaggga aagagctaca agcagcctaa cctgaaaatg      60 cacccccctcg tgcctccctt aaacagattc ttgtgtcagg gtgctgcagt tgcagagcgg    120
aaaatgcggt aa                                                         132
```

<210> SEQ ID NO 100
<211> LENGTH: 441
<212> TYPE: DNA
<213> ORGANISM: Artificial
<220> FEATURE:
<223> OTHER INFORMATION: Alien to Mouse cDNA

<400> SEQUENCE: 100

```
atgaatgggc tcctgcacac gacatataag gagaagacgt cgtatccgcg tgaggtgttt      60
gggcatagtg cagaaatttc ccgcctgtgt cctctgcctt ccagttccat ggcaaccccg    120
ccaaatgacg tgaatatggt gatcccctc aaaagacgtg cgctgacgaa cacctatggg    180
tctgcttcga ttcgtcagat gacgccgatt acaaccctca ccgtctctgc ctgggtttac    240
tcgagccaag aggcactcaa gtgtcgttac ctgggcttcc ggcggagaat tgaaatgccc    300
ttttgtttta gtggtgcggc caacagatcc tacaacttt ctgctaagga acgcttgggt    360
cacgcacctg cctgtatccg atggcacaga tatttatgga tgaacttgga catgaaaatg    420
ttgactgccc ttcgcatctg a                                              441
```

<210> SEQ ID NO 101
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 101

```
aaccaatccc atcccaggtg tgcggcgaat cggtcgatct agtcctaatt agccggatag      60
gaaaacctca                                                             70
```

<210> SEQ ID NO 102
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 102

```
aagaacccac gccgtctaca tatcgggcac gtgctataac gactcaggag tatttaacga      60
ccgcacggaa                                                             70
```

<210> SEQ ID NO 103
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 103

```
acaggtgtcc tcaaaccagc ctgaaacgtt actaggtgaa gaatcaccgc ggttgtcggt      60
```
agttaagcga 70

<210> SEQ ID NO 104
<211> LENGTH: 70
<212> TYPE: DNA
<213> ORGANISM: Artificial
<220> FEATURE:
<223> OTHER INFORMATION: Oligonucleotides identified according to the
    present invention as alien to mouse cDNA and useful for
    hybridization applications.

<400> SEQUENCE: 104
acccgcgtac acagtaggca ctctacggcg cgtttagcgt taatcaccaa ttttgcaata 60
gtcaccagag 70

<210> SEQ ID NO 105
<211> LENGTH: 70
<212> TYPE: DNA
<213> ORGANISM: Artificial
<220> FEATURE:
<223> OTHER INFORMATION: Oligonucleotides identified according to the
    present invention as alien to mouse cDNA and useful for
    hybridization applications.

<400> SEQUENCE: 105
acggactacc tcggccactt catttggcga cctgcggata ttgcttacga atctcgatct 60
tccggattat 70

<210> SEQ ID NO 106
<211> LENGTH: 70
<212> TYPE: DNA
<213> ORGANISM: Artificial
<220> FEATURE:
<223> OTHER INFORMATION: Oligonucleotides identified according to the
    present invention as alien to mouse cDNA and useful for
    hybridization applications.

<400> SEQUENCE: 106
agaagtcgtg tgatcgaggt agcactggga tttacgaaaa ttgccctacc ggtatacgct 60
aggccatacc 70

<210> SEQ ID NO 107
<211> LENGTH: 70
<212> TYPE: DNA
<213> ORGANISM: Artificial
<220> FEATURE:
<223> OTHER INFORMATION: Oligonucleotides identified according to the
    present invention as alien to mouse cDNA and useful for
    hybridization applications.

<400> SEQUENCE: 107
agcccacata tagcccacgc gggtgtcgac aacatatgtc gtatgcgagt aacgttttcg 60
tttgagatgg 70

<210> SEQ ID NO 108
<211> LENGTH: 70
<212> TYPE: DNA
<213> ORGANISM: Artificial
<220> FEATURE:
<223> OTHER INFORMATION: Oligonucleotides identified according to the
    present invention as alien to mouse cDNA and useful for
    hybridization applications.

<400> SEQUENCE: 108
atactacttt tgggtatgct agctacgtag tacccttcaa tagccgtcgc ttggtctctt 60

```
gcgcgtcacg                                                            70

<210> SEQ ID NO 109
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 109
catctatcta tgtaagttac cggcatgggt tatggattcg tggaccgcga tgtgacgtag    60
gggtttccac                                                            70

<210> SEQ ID NO 110
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 110
cattttaccg ttaccgggaa gcgtgtgtgt ctttatttgc gcgtacccag tgttgagaac    60
gacggaacag                                                            70

<210> SEQ ID NO 111
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 111
ccatccgggc cataagttta tagtagcgat tgttttgccc ctaccagcga atcgcgccca    60
gttagtaatc                                                            70

<210> SEQ ID NO 112
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 112
cccgagcttg cgctagtacg attatgtacc gctatgtcaa tttgacgccc tcgcactgcg    60
gcactttatt                                                            70

<210> SEQ ID NO 113
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 113
```

```
ccggctcggt gtcaccgcgg aagtaccttt gagtatcgca cttatcggct ttaacctgga    60
cgtaactaaa                                                           70
```

<210> SEQ ID NO 114
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 114

```
ccttggatgg gtaaattccc tcgtctacgc gtaacaactg aacgcgtagc gcgacggtct    60
caggaaatta                                                           70
```

<210> SEQ ID NO 115
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 115

```
cctttccgtg ttactcggcc ggcaaggacg cctcgtacca tctttgatag atgtatttgc    60
gtaaattcgg                                                           70
```

<210> SEQ ID NO 116
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 116

```
cgcgaccccg actggtagtt gcgcgctcgc attaccgagt tcacatcgca tgtactacat    60
tagagaaata                                                           70
```

<210> SEQ ID NO 117
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 117

```
cggccacaac tctcaggacg catataagac gcggaaaggc atacacgtct acttagagac    60
accgagactt                                                           70
```

<210> SEQ ID NO 118
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 118

```
ctgcttaacc gttccagagg ggcgttcgta tcaaaaaggg tgcgatttcg atcacgtcgc    60
agtgactcat                                                          70
```

<210> SEQ ID NO 119
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 119

```
gaatggcatc aacggcgctg tacatagtct tctcgcctac ataatagcgc tagttgatag    60
gaaccagggg                                                          70
```

<210> SEQ ID NO 120
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 120

```
gagctgcaca cccgcagaca tcatagtgag tgtaatcacg cacgtgacca gttaacccat    60
ttcgtggaga                                                          70
```

<210> SEQ ID NO 121
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 121

```
gatggattca cgaacgagca cttagtaacg cctggtactg acatcttatt gcacgtagtg    60
gagagcctgg                                                          70
```

<210> SEQ ID NO 122
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 122

```
gcaacgacca gctacctgtt aaccgtatat cagagtcgaa tgctcgcggt actgttcgaa    60
gtactcatcg                                                          70
```

<210> SEQ ID NO 123
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

```
<400> SEQUENCE: 123
gcagaattcc taaccatgca agcgtggcga ctcgtctctc gcaaagttct atacgaatca    60
gcgatgggta                                                           70

<210> SEQ ID NO 124
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 124
gccctctcgt cccacgttcg ctcgtcttgt tgacactact gacgggtatc cctctaaata    60
cttctctttt                                                           70

<210> SEQ ID NO 125
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 125
gcctcttcga tggggtccgt ctggtcagta ccgacgaaaa tgcgacggta gatgtcagaa    60
ttgattctgt                                                           70

<210> SEQ ID NO 126
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 126
gcgggctctt gtgcaaactt atggggctag tgactcgggt gtagcacgtt ttgcgaagac    60
taagacagta                                                           70

<210> SEQ ID NO 127
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 127
gcgtctatga caggtcgggc acttaggcgg cgacgcttga tgtttgagtc gcagatatta    60
gtttataagg                                                           70

<210> SEQ ID NO 128
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.
```

```
<400> SEQUENCE: 128
gctatctaac gcggtcttgc caatactacg aatggttgct acaggatatc gagtaccgca      60
aaatgggggc                                                             70

<210> SEQ ID NO 129
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 129
gggggcaact ctccaaccga gcgtgaatcc agcgattatt atcctactcc atactattag      60
cgggtatacg                                                             70

<210> SEQ ID NO 130
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 130
ggtacgaatc tcccattgca tggacaaata tagtccacgc attggacgca cccaccgatg      60
gctctccaat                                                             70

<210> SEQ ID NO 131
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 131
ggtcgtaccc aacctgacac gagatgtcgg cgctcgtttc gattggacga tcggatatat      60
gatcaagcaa                                                             70

<210> SEQ ID NO 132
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 132
ggttgttcca tgtactcgat actacctagg catcaggtgt atacgccggt ttggatgggc      60
gttcggcaaa                                                             70

<210> SEQ ID NO 133
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
``` hybridization applications.

<400> SEQUENCE: 133

```
gtgccacccc aattagtctt ttgtccgggc aagagtacg acaacggggt attttggtac    60
tatatcccac                                                          70
```

<210> SEQ ID NO 134
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 134

```
gttaagggtc tcgaaagatt tctactctcg acgtaccgtt ggcagcgcac taagaacggg    60
taatgtgctg                                                          70
```

<210> SEQ ID NO 135
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 135

```
gttaggcact tgcgcgtcaa gcgcgcaaac cctaattacg ttctgtccac gcgctaggga    60
tattcgtata                                                          70
```

<210> SEQ ID NO 136
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 136

```
taagatgcct gacgaaaaag tcccgtgtac ccacaacgga aagcgtgatc tagatagttc    60
ccttagcgcc                                                          70
```

<210> SEQ ID NO 137
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 137

```
taattttggg ttgtcgaggc ataaactggt atgctcgtct cgctcgacga gcggttgaac    60
gcctatcgct                                                          70
```

<210> SEQ ID NO 138
<211> LENGTH: 70
<212> TYPE: DNA
<213> ORGANISM: Artificial
<220> FEATURE:
<223> OTHER INFORMATION: Oligonucleotides identified according to the -continued present invention as alien to mouse cDNA and useful for
hybridization applications.

<400> SEQUENCE: 138
tattggccgc ggcgctaact tatatcgaga gatgtctagt ttccccaccc gttacatatt      60
ctacggggag                                                            70

<210> SEQ ID NO 139
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 139
tattttccgg tactgagtgg aacgacatga agttggcggt caggtcgtta tttcgcagcc      60
acgcaccact                                                            70

<210> SEQ ID NO 140
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 140
tcagatgtcg ttattaacgg gaaggtatcc ggttcactat cacggcgatt acttcgcgtt      60
gcgaaagggc                                                            70

<210> SEQ ID NO 141
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 141
tccggctccg cagacggttt aactcgaacc ttaaaagtcg tgtgaagcta cttcgagacc      60
atgcgctctt                                                            70

<210> SEQ ID NO 142
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 142
tctgttaccc acattgtcac cacttgacag gcgcacggtc gtttgtaaag cgactagcta      60
cgcaggtata                                                            70

<210> SEQ ID NO 143
<211> LENGTH: 70
<212> TYPE: DNA
<213> ORGANISM: Artificial
<220> FEATURE:

```
<223> OTHER INFORMATION: Oligonucleotides identified according to the
      present invention as alien to mouse cDNA and useful for
      hybridization applications.

<400> SEQUENCE: 143
tggagatgcg aacgttggga gtatcaatcc ccggtgcaac ccctaatcc gacatgccgc    60 aagtatatat                                                          70

<210> SEQ ID NO 144
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 144
tgggcgccta gagccagcat attacaggcg agctgttttc gcgtctctaa tgacgtgtac    60
gcgattctat                                                           70

<210> SEQ ID NO 145
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 145
tgtagacagg gcgcgattgt atgggacagt ttacgcacta accgactcta caatgtagtg    60
tttgtcgggc                                                           70

<210> SEQ ID NO 146
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 146
ttccgcatga gatcaacgcg tggtcaatac gtgttaagaa ccggtcgacg ccagctagac    60
ctaatgcgtt                                                           70

<210> SEQ ID NO 147
<211> LENGTH: 70
<212> TYPE: DNA
<213> ORGANISM: Artificial
<220> FEATURE:
<223> OTHER INFORMATION: Oligonucleotides identified according to the
      present invention as alien to mouse cDNA and useful for
      hybridization applications.

<400> SEQUENCE: 147
tttcgactgg gggtacaaag ctccctattt gccgttcacg aagctacata ctggtctagc    60
gcgtgcacaa                                                           70

<210> SEQ ID NO 148
<211> LENGTH: 23
<212> TYPE: DNA
<213> ORGANISM: Artificial
```

```
<220> FEATURE:
<223> OTHER INFORMATION: Anti-alien in spike control concept. Sequences
      of alien genes designed by linking four 70mer alien sequences
      together.

<400> SEQUENCE: 148
ttctaatacg actcactata ggg                                             23

<210> SEQ ID NO 149
<211> LENGTH: 68
<212> TYPE: DNA
<213> ORGANISM: Artificial
<220> FEATURE:
<223> OTHER INFORMATION: Anti-alien in spike control concept. Sequences
      of alien genes designed by linking four 70mer aliensequences
      together.

<400> SEQUENCE: 149
ccatccgggc catacgtttt agtagcgatt gtttgcccct accagcgaat cgcgcccagt     60
tagtaatc                                                              68

<210> SEQ ID NO 150
<211> LENGTH: 70
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 150
taattttggg ttgtcgaggc ataaactggt atgctcgtct cgctcgacga gcggttgcac     60
gcctatcgct                                                            70

<210> SEQ ID NO 151
<211> LENGTH: 70
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 151
gtgccacccc aatttgtctt ttgtccgggc caagagtacg acaacggggt attttggtac     60
tatatcccac                                                            70

<210> SEQ ID NO 152
<211> LENGTH: 70
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 152
gcgggctctt gtgcaaactt atggggctgg ttactcgggt gtagcacgtt ttgcgaagac     60
tacgacagta                                                            70
```

<210> SEQ ID NO 153
<211> LENGTH: 19
<212> TYPE: DNA
<213> ORGANISM: Artificial
<220> FEATURE:
<223> OTHER INFORMATION: Anti-alien in spike control concept. Sequences of alien genes designed by linking four 70mer alien sequences together.

<400> SEQUENCE: 153
aaaaaaaaaa aaaaaaaaa                                              19

<210> SEQ ID NO 154
<211> LENGTH: 70
<212> TYPE: DNA
<213> ORGANISM: Artificial
<220> FEATURE:
<223> OTHER INFORMATION: Anti-alien in spike control concept. Sequences of alien gene designed by linking four 70mer alien sequences together.

<400> SEQUENCE: 154
catctatcta tgtcagttac cggcatgggt tatggattcg tggaccgcga tgtgacgttg    60
gggtttccac                                                          70

<210> SEQ ID NO 155
<211> LENGTH: 70
<212> TYPE: DNA
<213> ORGANISM: Artificial
<220> FEATURE:
<223> OTHER INFORMATION: Anti-alien in spike control concept. Sequences of alien genes designed by linking four 70mer alien sequences together.

<400> SEQUENCE: 155
tcagatgtcg ttattatcgg gaaggtatcc ggttcactat cacggcgatt acttcgcgtt    60
gcgaaagggc                                                          70

<210> SEQ ID NO 156
<211> LENGTH: 70
<212> TYPE: DNA
<213> ORGANISM: Artificial
<220> FEATURE:
<223> OTHER INFORMATION: Anti-alien in spike control concept. Sequences of alien genes designed by linking four 70mer alien sequences together.

<400> SEQUENCE: 156
taattttggg ttgtcgaggc ataaactggt atgctcgtct cgctcgacga gcggttgcac    60
gcctatcgct                                                          70

<210> SEQ ID NO 157
<211> LENGTH: 69
<212> TYPE: DNA
<213> ORGANISM: Artificial
<220> FEATURE:
<223> OTHER INFORMATION: Anti-alien in spike control concept. Sequence of alien genes designed by linking four 70mer alien sequences together.

<400> SEQUENCE: 157
tccgcatgcg atcaacgcgt ggtcaatacg tgtttagaac cggtcgacgc cagcttgacc    60
tactgcgtt                                                           69

<210> SEQ ID NO 158

```
<211> LENGTH: 20
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 158
aaaaaaaaaa aaaaaaaaaa                                                20

<210> SEQ ID NO 159
<211> LENGTH: 69
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 159
ccctctcgtc ccacgttcgc tcgtcttgtt gacactactg acgggtatcc ctctaaatac    60
ttctctttt                                                            69

<210> SEQ ID NO 160
<211> LENGTH: 70
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 160
gttaagggtc tcgaaagatt tctactctcg acgtaccgtt ggcagcgcac taagaacggg    60
taatgtgctg                                                           70

<210> SEQ ID NO 161
<211> LENGTH: 70
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 161
tattttccgg tactgagtgg aacgacatga agttggcggt caggtcgtta tttcgcagcc    60
acgcaccact                                                           70

<210> SEQ ID NO 162
<211> LENGTH: 70
<212> TYPE: DNA
<213> ORGANISM: Artificial
<220> FEATURE:
<223> OTHER INFORMATION: Anti-alien in spike control concept. Sequences
      of alien genes designed by linking four 70mer alien sequences
      together.

<400> SEQUENCE: 162
cggccacaac tctcaggacg catataagac gcggaaaggc atacacgtct acttagagac    60
accgagactt                                                           70

<210> SEQ ID NO 163
<211> LENGTH: 20
```

```
-continued

<212> TYPE: DNA
<213> ORGANISM: Artificial
<220> FEATURE:
<223> OTHER INFORMATION: Anti-alien in spike control concept.  Sequences
      of alien genes designed by linking four 70mer alien sequences
      together.

<400> SEQUENCE: 163
aaaaaaaaaa aaaaaaaaaa                                                    20
```